(12) United States Patent
Kambe et al.

(10) Patent No.: US 8,962,868 B2
(45) Date of Patent: *Feb. 24, 2015

(54) BICYCLIC COMPOUND AND USE THEREOF FOR MEDICAL PURPOSES

(71) Applicant: Ono Pharmaceutical Co., Ltd., Osaka (JP)

(72) Inventors: Tohru Kambe, Osaka (JP); Toru Maruyama, Osaka (JP); Shinsaku Yamane, Osaka (JP); Satoshi Nakayama, Osaka (JP); Kousuke Tani, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/081,286

(22) Filed: Nov. 15, 2013

(65) Prior Publication Data

US 2014/0073676 A1    Mar. 13, 2014

Related U.S. Application Data

(63) Continuation of application No. 13/384,383, filed as application No. PCT/JP2010/062587 on Jul. 27, 2010, now Pat. No. 8,614,340.

(30) Foreign Application Priority Data

Jul. 28, 2009  (JP) ................. 2009-175246

(51) Int. Cl.
| | | |
|---|---|---|
| *C07D 313/00* | (2006.01) | |
| *C07D 407/12* | (2006.01) | |
| *A61K 31/4427* | (2006.01) | |
| *A61K 31/558* | (2006.01) | |
| *C07D 313/06* | (2006.01) | |
| *C07D 401/06* | (2006.01) | |
| *C07D 417/04* | (2006.01) | |

(52) U.S. Cl.
CPC .......... *C07D 407/12* (2013.01); *A61K 31/4427* (2013.01); *A61K 31/558* (2013.01); *C07D 313/06* (2013.01); *C07D 401/06* (2013.01); *C07D 417/04* (2013.01)
USPC ........................................ 549/355

(58) Field of Classification Search
CPC .................................... C07D 313/06
USPC .......................................... 549/355
See application file for complete search history.

(56) References Cited

U.S. PATENT DOCUMENTS

| | | | |
|---|---|---|---|
| 4,230,721 A | 10/1980 | Gandolfi et al. | |
| 4,367,237 A | 1/1983 | Wakatsuka et al. | |
| 4,490,537 A | 12/1984 | Johnson | |
| 6,583,174 B1 | 6/2003 | Ueno et al. | |
| 8,614,340 B2 * | 12/2013 | Kambe et al. | 549/355 |
| 2006/0035949 A1 | 2/2006 | Donde et al. | |

FOREIGN PATENT DOCUMENTS

| | | | |
|---|---|---|---|
| JP | 50-37780 | A | 4/1975 |
| JP | 53-84959 | A | 7/1978 |
| JP | 53-132573 | A | 11/1978 |
| JP | 55-73678 | A | 6/1980 |
| JP | 64-068367 | A | 3/1989 |
| WO | 2001/027099 | A2 | 4/2001 |
| WO | 2007/149829 | A2 | 12/2007 |
| WO | 2011/013651 | A1 | 2/2011 |
| WO | 2012/102355 | A1 | 8/2012 |
| WO | 2012/102357 | A1 | 8/2012 |

OTHER PUBLICATIONS

Wolff, Burger's medicinal Chemistry and Drug Discovery, vol. 1, Principles and Practice, John Wiley & sons, New York, 1997.*
West, Solid State Chemistry and Its Applications, John Wiley & Sons, 1984.*
International Search Report (PCT/ISA/210), issued by the International Searching Authority in corresponding International Application No. PCT/JP2010/062587 on Sep. 14, 2010.
Extended European Search Report issued on Dec. 3, 2012 in corresponding European patent application No. 10 804 397.
International Search Report, dated Mar. 13, 2012, issued in International Patent Application No. PCT/JP2012/051721.
International Search Report, dated Mar. 13, 2012, issued in International Patent Application No. PCT/JP2012/051718.

* cited by examiner

*Primary Examiner* — Nizal Chandrakumar
(74) *Attorney, Agent, or Firm* — Sughrue Mion, PLLC

(57) ABSTRACT

Since a compound represented by the general formula (I) (wherein definition of each group is as described in the specification), a salt thereof, a solvate thereof, or a prodrug thereof has strong and sustaining intraocular pressure lowering activity and, further, has no side effect on eyes such as ocular stimulating property (hyperemia, corneal clouding etc.), aqueous humor protein rise etc., it has high safety, and can be an excellent agent for preventing and/or treating glaucoma etc.

11 Claims, 6 Drawing Sheets

BICYCLIC COMPOUND AND USE THEREOF FOR MEDICAL PURPOSES

This application is a Rule 53(b) continuation of U.S. patent application Ser. No. 13/384,383 filed Jan. 17, 2012, which is a national stage of PCT/JP2010/062587 filed Jul. 27, 2010, and claims priority to Japanese Patent Application No. JP 2009-175246 filed Jul. 28, 2009. The entire disclosures of the prior applications are considered part of the disclosure of the accompanying continuation application, and are hereby incorporated by reference.

TECHNICAL FIELD

The present invention relates to a compound represented by the general formula (I)

[Chemical formula 1]

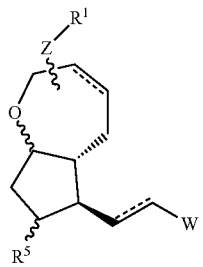

(I)

(wherein all symbols represent the same meanings as those described below), a salt thereof, or a solvate thereof, or a prodrug thereof (hereinafter, abbreviated as present invention compound in some cases).

BACKGROUND OF ART

Glaucoma is an ocular disease having the characteristic of a visual functional disorder which causes a transient or permanent visual field defect and decreased vision. This is derived from that since an aqueous humor is accumulated by a circulatory disorder of an aqueous humor, and an intraocular pressure is continuously increased, an optic nerve is compressed. Decrease in an intraocular pressure is effective for treatment of glaucoma and, in order to decrease an intraocular pressure, for example, drug treatment (eye drops, internal remedy, infusion treatment), laser treatment, or operation treatment is performed.

Previously, among prostaglandins (PGs) which are physiologically active substances, as those that decrease an intraocular pressure, PGFs and PGIs are known. Development of a drug for treating glaucoma or ocular hypertension is being progressed using derivatives of them, and there are some drugs which are actually sold (e.g. latanoprost etc.). However, the existing glaucoma treating drug alone is insufficient in intraocular pressure lowering action and sustainability of drug efficacy and, in at site of glaucoma treatment, since administration at a frequent time or a high concentration, or therapy of joint use of drugs having different mechanisms of action are being performed seeking stronger intraocular pressure lowering action, manifestation of side effects is feared. For this reason, drugs having stronger and sustaining intraocular pressure lowering action, and high safety are desired.

Meanwhile, as the prior art of the present invention compound, the following PG derivatives are exemplified.

As a PG derivative having a bicyclic skeleton, for example, a compound of the general formula (a):

[Chemical formula 2]

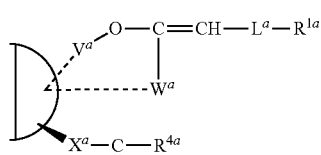

(a)

(wherein,

[Chemical formula 3]

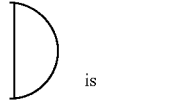

is

[Chemical formula 4]

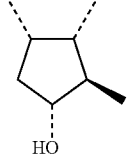

etc., $L^a$ is —$(CH_2)_{da}$—$C(R^{2a})_2$— (wherein da is 0 to 5, and $R^{2a}$s are hydrogen, methyl or fluoro, and are the same or different) etc., $Q^a$ is an oxygen atom etc., $R^{1a}$ is $COOR^{3a}$ (wherein $R^{3a}$ is hydrogen, alkyl of 1 to 12 carbon atoms etc.) etc., $R^{4a}$ is:

[Chemical formula 5]

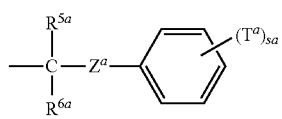

(wherein $R^{5a}$ and $R^{6a}$ are hydrogen, alkyl of 1 to 4 carbon atoms or fluoro, and are the same or different, $Z^a$ is an oxygen atom etc., $T^a$ is alkyl of 1 to 4 carbon atoms, fluoro, chloro etc., and sa is 0 to 3) etc., $V^a$ is a valence bond or —$CH_2$, $W^a$ is —$(CH_2)_h$, h is 1 or 2, $X^a$ is trans-CH=CH— etc. (a part of definitions of groups was extracted) is known (see Patent Literature 1).

In addition, a compound represented by the general formula (b):

[Chemical formula 6]

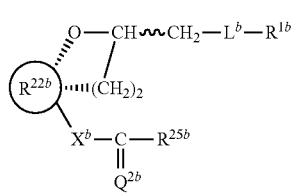

(b)

(wherein $L^b$ represents —$(CH_2)_{db}$— (wherein db represents 1 to 5) etc., $Q^{2b}$ represents O etc., $R^{1b}$ represents —$COOR^{19b}$ (wherein $R^{19b}$ represents a C1-C12 alkyl group or a hydrogen atom etc.) etc., a ring $R^{22b}$ represents:

[Chemical formula 7]

(wherein $R^{4b}$ represents a hydrogen atom etc.) etc., $R^{25b}$ represents:

[Chemical formula 8]

(wherein $R^{5b}$ and $R^{6b}$ represent a hydrogen atom etc., $Z^b$ represents —O— etc., $T^b$ represents a C1-4 alkyl group, fluorine, chlorine, trifluoromethyl or —$OR^{7b}$— (wherein $R^{7b}$ represents C1-4 alkyl), sb represents 0, 1, 2 or 3, and $X^b$ represents:

[Chemical formula 9]

cis or trans $-\underset{H}{C}=\underset{H}{C}-$, $-C\equiv C-$ or $-\underset{H_2}{C}-\underset{H_2}{C}-$ (a part of definitions of groups was extracted)) (see Patent Literature 2) is known.

Further, a process for producing a compound represented by the general formula (c):

[Chemical formula 10]

(c)

(wherein $A^c$ represents a C1-2 alkylene group, $B^c$ represents a C2-6 alkylene group, $X^c$ represents C(O) etc., and $Z^c$ represents a C1-4 alkylene group etc. (a part of definitions of groups was extracted)) is known (see Patent Literature 3).

Meanwhile, it has been reported that agonistic activity on an IP receptor among PG receptors causes hyperemia and rise in a aqueous humor protein, and inducement of stimulation on eyes has been feared (see Non-Patent Literatures 1 and 2). For this reason, since the compound described in Patent Literature 2 which is a PGI2 derivative has agonistic activity on an IP receptor, there is a probability that property of stimulating eyes etc. are induced.

Further, it has been also known that agonistic activity on an EP 1 receptor among PGE subtype receptors causes itching of eyes (see Non-Patent Literature 3).

The present invention compound is a compound which has low agonistic activity on an IP receptor and an EP 1 receptor, and has selective agonistic activity on a FP receptor, but there is neither the description nor the suggestion regarding such the characteristic (selectivity) in any prior arts.

PRIOR ART LITERATURES

Patent Literatures

Patent Literature 1: JP-A No. 52-95644 gazette
Patent Literature 2: U.S. Pat. No. 4,490,548
Patent Literature 3: JP-A No. 50-37780 gazette Non-Patent Literatures Non-Patent Literature 1: Investigative Ophthalmology & Visual Science, Vol. 28, p. 470-476, 1987
Non-Patent Literature 2: Investigative Ophthalmology & Visual Science, Vol. 23, p. 383-392, 1982
Non-Patent Literature 3: The Journal of Pharmacology and Experimental Therapeutics, Vol. 279, No. 1, p. 137-142, 1996

SUMMARY OF THE INVENTION

Problems to be Solved by the Invention

A compound which has strong and sustaining intraocular pressure lowering action and, further, has no fear of side effects on eyes is desired.

Means to Solve the Problems

In order to solve the aforementioned problems, the present inventors intensively studied to find out a compound which has improved selectivity on a PG receptor subtype, that is, a compound which has low agonistic activity on an IP receptor and an EP 1 receptor, and has selective agonistic activity on a FP receptor and, as a result, completed the present invention.

That is, the present invention relates to:

1. A compound represented by the general formula (I):

[Chemical formula 11]

(I)

(wherein $R^1$ represents (1) COOH, (2) $COOR^2$, (3) $CH_2OH$, or (4) $CONR^3R^4$, $R^2$ represents a C1-C6 alkyl group optionally substituted with a hydroxy group, $ONO_2$ or a C1-4 alkoxy group, $R^3$ and $R^4$ each represent independently a hydrogen atom, or a C1-4 alkyl group optionally substituted with $ONO_2$, $R^5$ represents a halogen atom, a hydroxy group, or a C1-4 alkoxy group, Z represents (1)—$(CH_2)_m$—, (2)—$(CH_2)_n$—CH=CH—, (3)—$(CH_2)_p$-A-$CH_2$—, or (4) ring 1, A represents an oxygen atom, or a sulfur atom, W represents a C1-6 alkyl group optionally substituted with 1 to 5 substituents selected from the group consisting of (1) a hydroxy group, (2) an oxo group, (3) a halogen atom, (4) a C1-4 alkyl group, (5) a C1-4 alkoxy group, (6) ring 2, (7) —O-ring 2, and (8) —S-ring 2, ring 1 and ring 2 each represent independently a C3-10 carbocycle or a 3- to 10-membered heterocycle, optionally substituted with 1 to 5 substituents selected from the group consisting of (1) a halogen atom, (2) $CF_3$, (3) $OCF_3$, (4) a C1-4 alkoxy group, (5) a C1-4 alkyl group, (6) a hydroxy group, and (7) a nitrile group, m represents an integer of 1 to 6, n represents an integer of 1 to 4, p represents an integer of 1 to 4, ⋯⋯ [Chemical Formula 12]

represents a single bond or a double bond,

⦁⦁⦁ [Chemical Formula 13]

represents α configuration,

╱ [Chemical Formula 14]

represents β configuration,

∿ [Chemical Formula 15]

represents α configuration, β configuration or an arbitrary mixture of them), or a salt thereof, a solvate thereof, or a prodrug thereof, 2. The compound according to 1, represented by the general formula (I-1):

[Chemical formula 16]

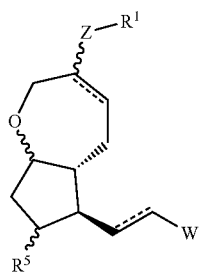

(I-1)

(wherein all symbols represent the same meanings as those described in 1), or a salt thereof, a solvate thereof, or a prodrug thereof, 3. The compound according to 2, represented by the general formula (I-2):

[Chemical formula 17]

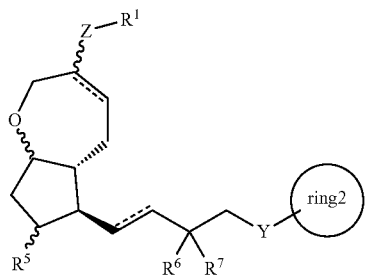

(I-2)

(wherein $R^6$ and $R^7$ each represent independently a hydrogen atom, a hydroxy group, a halogen atom, a C1-4 alkyl group or a C1-4 alkoxy group, $R^6$ and $R^7$ may be taken together to form an oxo group, Y represents —$CH_2$—, —O— or —S—, and other symbols represent the same meanings as those described in 1), or a salt thereof, a solvate thereof, or a prodrug thereof, 4. The compound according to 3, wherein the ring 2 is a C3-7 carbocycle, or a salt thereof, a solvate thereof, or a prodrug thereof, 5. The compound according to 3, wherein Z is (1)—$(CH_2)_m$—, or (2)—$(CH_2)_p$-A-$CH_2$— (all symbols represent the same meanings as those described 1), or a salt thereof, a solvate thereof, or a prodrug thereof, 6. The compound according to 3, wherein the compound represented by the general formula (I-2) is a compound selected from:

(1)  4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoic acid, (2) ethyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate, (3) 2-propanyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate, (4)  4-{(3S,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoic acid, (5) 2-propanyl 4-{(3S,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoate, (6) 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoic acid, and (7) 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate, a salt thereof, a solvate thereof, or a prodrug thereof, 7. A pharmaceutical composition comprising the compound represented by the general formula (I) according to 1, or a salt thereof, a solvate thereof, or a prodrug thereof, 8. The pharmaceutical composition according to 7, which is a FP agonist, 9. The pharmaceutical composition according to 7, which is an agent for preventing and/or treating an ocular disease, 10. The pharmaceutical composition according to 9, wherein the ocular disease is glaucoma, ocular hypertension, macular edema, macular degeneration, retina and optic nerve tensile force rise, myopia, hypermetropia, astigma, dry eye, amotio retinae, cataract, intraocular pressure rise due to trauma or inflammation, intraocular pressure rise due to a drug, or intraocular pressure rise after operation, 11. A method of preventing and treating an ocular disease, comprising administering an effective amount of the compound represented by the general formula (I) according to 1, or a salt thereof, a solvate thereof, or a prodrug thereof to a mammal, 12. The compound represented by the general formula (I) according to 1, or a salt thereof, a solvate thereof, or a prodrug thereof, for preventing and/or treating an ocular disease and, 13. The compound represented by the general formula (I) according to 1, or a salt thereof, a solvate thereof, or a prodrug thereof, for producing an agent for preventing and/or treating an ocular disease.

Effect of the Invention

The present invention compound has strong and sustained intraocular pressure lowering action, and is useful as a therapeutic agent for glaucoma having no side effect on eyes such as ocular stimulating property (hyperemia, cloudy cornea etc.), humor protein rise etc.

MODE FOR CARRYING OUT THE INVENTION

Figure 1:
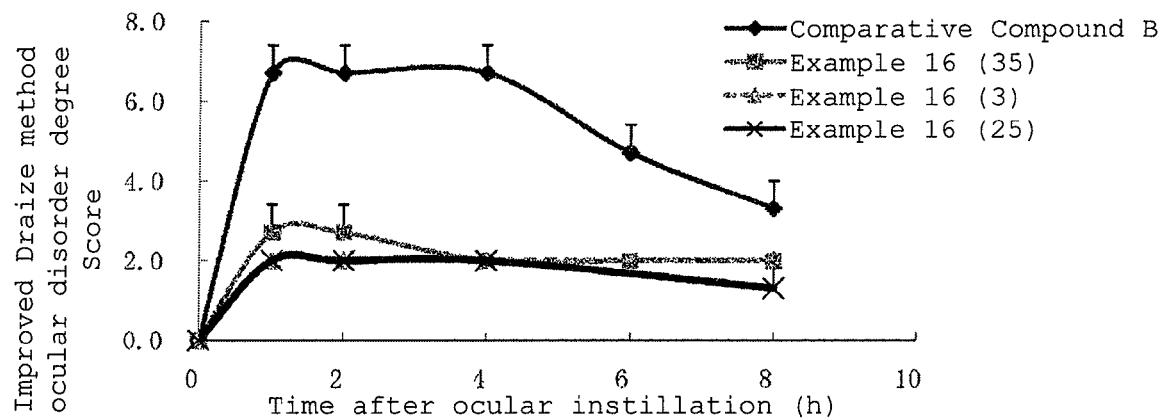
FIG. 1 A graph expressing transition of ocular stimulating property based on the Draize score after ocular instillation of the present invention compound and a comparative compound.

The present invention will be explained in detail below.

In the present invention, the C1-6 alkyl group means a straight or branched C1-6 alkyl group such as methyl, ethyl, propyl, isopropyl, butyl, sec-butyl, tert-butyl, pentyl, isopentyl, tert-pentyl, neopentyl, hexyl etc.

In the present invention, the C1-4 alkyl group means a straight or branched C1-4 alkyl group such as methyl, ethyl, propyl, isopropyl, butyl, sec-butyl, tert-butyl etc.

In the present invention, the C1-4 alkoxy group means a straight or branched C1-4 alkoxy group such as methoxy, ethoxy, propoxy, isopropoxy, butoxy, isobutyloxy, tert-butoxy etc.

In the present invention, the halogen atom means fluorine, chlorine, bromine, and iodine.

In the present invention, the C3-10 carbocycle means a C3-10 monocyclic or bicyclic carbocycle, a part or all of which may be saturated, and examples include cyclopropane, cyclobutane, cyclopentane, cyclohexane, cycloheptane, cyclooctane, cyclononane, cyclodecane, cyclopentene, cyclohexne, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, perhydroindane, naphthalene, dihydronaphthalene, tetrahydronaphthalene, perhydronaphthalene etc.

In the present invention, the C3-7 carbocycle means a C3-7 monocyclic carbocycle, a part or all of which may be saturated, and examples include cyclopropane, cyclobutane, cyclopentane, cyclohexane, cycloheptane, cyclopentene, cyclohexene, cycloheptene, cyclopentadiene, cyclohexadiene, cycloheptadiene, benzene, etc.

In the present invention, the 3- to 10-membered heterocycle means a 3- to 10-membered monocyclic or bicyclic heterocycle, a part or all of which may be saturated, comprising 1 to 5 hetero atoms selected from an oxygen atom, a nitrogen atom and a sulfur atom, and examples include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isooxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, pyrrolopyridine, benzoxazole, benzothiazole, benzimidazole, chromene, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, and perhydrobenzimidazole.

In the present invention, the sulfur atom in A includes an oxidized sulfur atom, that is, —SO— or —SO$_2$— in addition to —S—.

In the present invention, as $R^2$, methyl, ethyl, propyl, or isopropyl is preferable.

In the present invention, as $R^5$, a hydroxy group, or a halogen atom is preferable.

In the present invention, as Z, —$(CH_2)_m$—, —$(CH_2)_n$—CH=CH—, —$(CH_2)_p$-A-$CH_2$—, or ring 1 is preferable, and —$(CH_2)_m$—, or —$(CH_2)_p$-A-$CH_2$— is more preferable. Herein, as A, an oxygen atom is preferable.

In the present invention, as the "C1-6 alkyl group" represented by W, an ethyl group, or a propyl group is preferable. Herein, as a substituent of the "C1-6 alkyl group", a hydroxy group, an oxo group, a halogen atom, a C1-4 alkyl group, a C1-4 alkoxy group, —O-ring 2 or ring 2 is preferable.

In the present invention, as the ring 1, benzene or a thiazole ring is preferable.

In the present invention, as the ring 2, a C3- to C7-membered carbocycle is preferable, and benzene, or a cyclohexane ring is more preferable. Herein, as a substituent of the ring 2, a C1-4 alkyl group, a C1-4 alkoxy group, $CF_3$, $OCF_3$ or a halogen atom is preferable, and a C1-4 alkyl group, $CF_3$, $OCF_3$ or a halogen atom is more preferable.

In the present invention, as m, an integer of 2 to 4 is preferable.

In the present invention, as n, 1 is preferable.

In the present invention, the α chain means a side chain binding to a 7-membered ring, and the ω chain means a side chain binding to a 5-membered ring, in each general formula.

In the present invention, among the compound represented by the general formula (I), a compound represented by the general formula (I-1):

[Chemical formula 18]

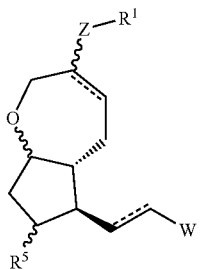

(I-1)

(wherein all symbols represent the same meanings as those described above), or a compound represented by the general formula (I-1-1):

[Chemical formula 19]

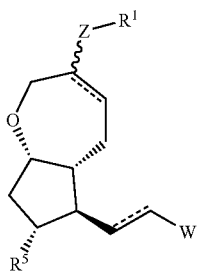

(I-1-1)

(wherein all symbols represent the same meanings as those described above) is preferable, a compound represented by the general formula (I-2):

[Chemical formula 20]

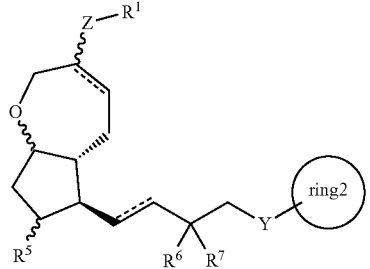

(I-2)

(wherein all symbols represent the same meanings as those described above), or a compound represented by the general formula (I-2-1)

[Chemical formula 21]

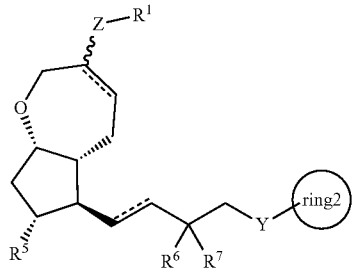

(I-2-1)

(wherein all symbols represent the same meanings as those described above) is more preferable. Herein, as $R^6$ and $R^7$, a hydrogen atom, a halogen atom or a hydroxy group is preferable and, as Y, —O— is preferable.

[Isomer]

In the present invention, an isomer includes all isomers unless otherwise is indicated. For example, the alkyl group includes a straight alkyl group and a branched alkyl group. Further, all of an isomer at a double bond, a ring, or a condensed ring (E isomer, Z isomer, cis isomer, trans isomer), an isomer due to the presence of an asymmetric carbon etc. (R, S isomer, α,β configuration, enantiomer, diastereomer), an optically active body having optical rotation (D, L, d, l isomer), a polar body derived from chromatographic separation (high polar compound, low polar compound), an equilibrated compound, a rotation isomer, a mixture of them at an arbitrary ratio, and a racemic mixture are included in the present invention. In addition, in the present invention, the isomer includes all isomers derived from tautomers.

In addition, the optically active compound in the present invention may include not only 100% pure compounds, but also other optical isomers or diastereomers which are less than 50% pure.

In the present invention, unless otherwise is indicated, as is apparent to a person skilled in the art, a symbol:

 [Chemical Formula 22]

represents that a group is bound to another side of a paper plane (i.e. α configuration),

 [Chemical Formula 23]

represents that a group is bound to a front side of a paper plane (i.e. β configuration),

 [Chemical Formula 24]

represents α configuration, β configuration or a mixture thereof, and

/ [Chemical Formula 25]

represents a mixture of α configuration and β configuration.

The compound represented by the general formula (I) is converted into a corresponding salt by the known method. As the salt, a water-soluble salt is preferable. Examples of a suitable salt include salts of an alkali metal (potassium, sodium etc.), salts of an alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.) etc.

The compound represented by the general formula (I) and a salt thereof can be also converted into a solvate. It is preferable that the solvate is low-toxic and water-soluble. Examples of a suitable solvate include solvates with, for example, water, or alcohol-based solvents (e.g. ethanol etc.).

In addition, a prodrug of the compound represented by the general formula (I) refers to a compound which is converted into the compound represented by the general formula (I) by a reaction with an enzyme or gastric acid in a living body. Examples of the prodrug of the compound represented by the general formula (I), when the compound represented by the general formula (I) has a hydroxy group, include compounds in which a hydroxy group is acylated, alkylated, phosphorylated, or boronized (e.g. compounds in which a hydroxy group of the present invention compound is acetylated, palmitoylated, propanoylated, pivaloylated, succinylated, fumarylated, alanylated, or dimethylaminomethylcarbonized etc.); compounds in which a carboxyl group of the compound represented by the general formula (I) is esterified, or amidated (e.g. compounds in which a carboxyl group of the compound represented by the general formula (I) is ethyl-esterified, isopropyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated) etc. These compounds can be produced by the known method. In addition, the prodrug of the compound represented by the general formula (I) may be any of a hydrate and a non-hydrate. In addition, the prodrug of the compound represented by the general formula (I) may be a prodrug which is changed to the compound represented by the general formula (I) under the physiological condition, as described in "Development of Medicaments" published in 1990 by Hirokawa-Shoten Ltd., Vol. 7, "Molecular Design", p. 163-198. Further, the compound represented by the general formula (I) may be labeled with an isotopic element (e.g. $^2$H, $^3$H, $^{11}$C, $^{13}$C, $^{14}$C, $^{13}$N, $^{15}$N, $^{17}$O, $^{18}$O, $^{35}$S, $^{18}$F, $^{36}$Cl, $^{123}$I, $^{125}$I etc.) etc.

Particularly, examples of a preferable prodrug of the compound represented by the general formula (I), upon ocular instillation administration of the compound represented by the general formula (I), include compounds in which a carboxyl group possessed by the compound represented by the general formula (I) is methyl-esterified, ethyl-esterified, propyl-esterified, isopropyl-esterified, butyl-esterified, isobutyl-esterified, sec-butyl-esterified, tert-butyl-esterified, pentyl-esterified, isopentyl-esterified, neopentyl-esterified, cyclopentyl-esterified, hexyl-esterified, cyclohexyl-esterified, trifluoroethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated etc.

[Process for Producing Present Invention Compound]

The present invention compound can be produced by the known method, for example, the method described in Comprehensive Organic Transformations: A Guide to Functional Group Preparations 2$^{nd}$ Edition (Richard C. Larock, John Wiley & Sons Inc, 1999), or can be produced by appropriately improving the methods shown in Examples, and using a combination of them.

Among the compound represented by the general formula (I), a compound in which

[Chemical Formula 26]

are as described below, respectively, an α chain represents β configuration, $R^1$ represents $COOR^2$, $R^5$ represents a hydroxy group, and one of $R^6$ and $R^7$ represents hydrogen, and the other represents a hydroxy group, in the compound represents by general formula (I-2), that is, a compound represented by the general formula (I-2-a):

[Chemical formula 27]

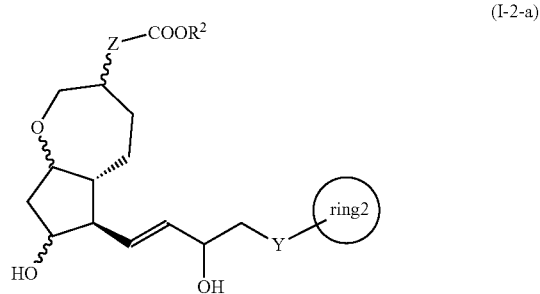

(I-2-a)

(wherein all symbols represent the same meanings as those described above) can be produced using a compound represented by the general formula (II):

[Chemical formula 28]

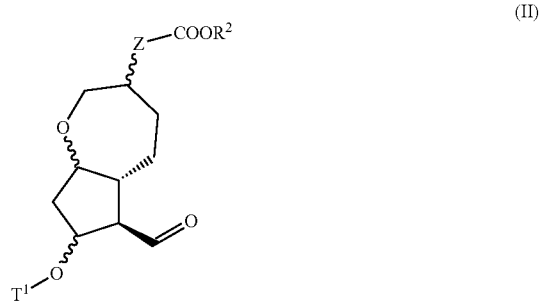

(II)

(wherein $T^1$ represents a protective group of a hydroxy group (e.g. 2-tetrahydropyranyl (THP) group, p-phenylbenzoyl group etc.), and other symbols represent the same meanings as those described above) as a starting substance, according to the following reaction step formula 1.

[Chemical formula 29]

Reaction step formula 1

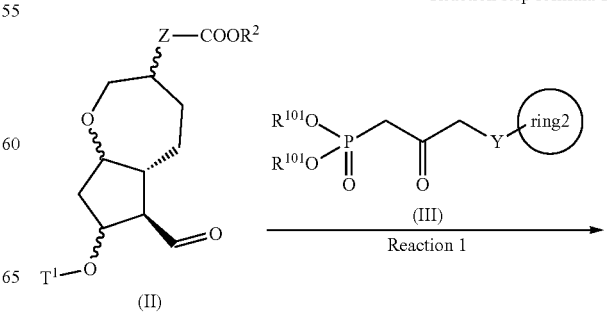

-continued

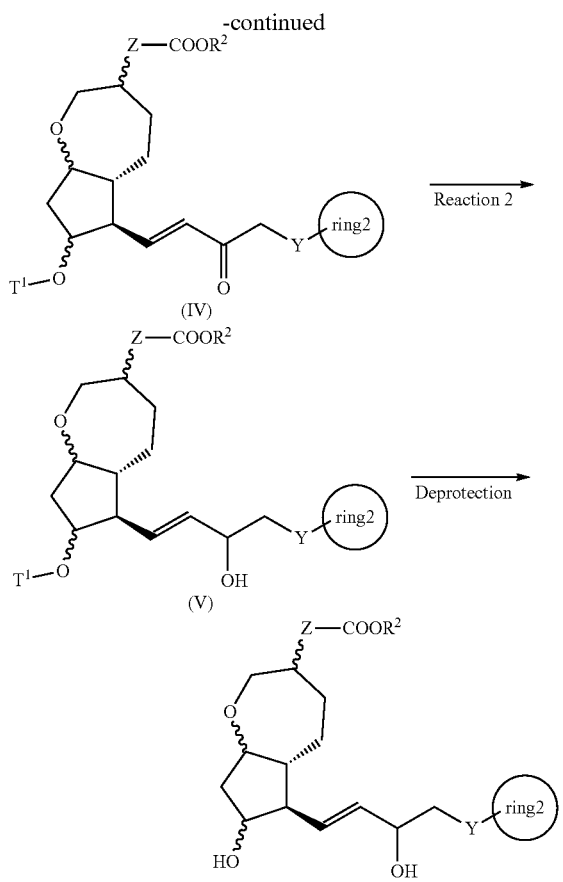

(wherein $R^{101}$ represents a C1-6 alkyl group, and other symbols represent the same meanings as those described above)

In the reaction step formula 1, the reaction 1 is known and, for example, is performed by reacting a compound represented by the general formula (II) and a compound represented by the general formula (III) at a temperature of −20 to 70° C. in an organic solvent (e.g. tetrahydrofuran (THF), dimethylformamide (DMF), dimethoxyethane (DME), dioxane, acetonitrile, ethanol, dichloromethane etc.) or in water, or in a mixed solution thereof, in the presence of a base (e.g. sodium hydride, sodium hydroxide, potassium hydroxide, potassium phosphate, potassium tert-butoxide, potassium carbonate, tertiary amine+lithium chloride etc.).

In the reaction step formula 1, the reaction 2 is known, and is performed by reacting the compound represented by the general formula (IV) obtained in the reaction 1 at −20 to 50° C. in an organic solvent (e.g. THF, DME, toluene, dichloromethane, diethyl ether, dioxane etc.), in the presence or the absence of cerium chloride using a reducing agent (e.g. sodium borohydride, zinc borohydride etc.). In addition, when only one of steric isomers is selectively produced, the reaction is performed at a temperature of −100 to 50° C. using an asymmetric reducing agent (e.g. chlorodiisopinocamphenylborane etc.), or a combination of an asymmetric aid and a reducing agent ((R)-2-methyl-CBS-oxazaborolidine and boron hydride• tetrahydrofuran complex or boranedimethyl sulfide complex, (S)-(−)-binaphthol and lithium aluminum hydride etc.).

In the reaction step formula 1, a reaction of deprotecting a protective group is known, and can be performed by the following step. Examples include (1) a deprotection reaction by alkali hydrolysis, (2) a deprotection reaction under the acidic condition, (3) a deprotection reaction by hydrogenation degradation, (4) a deprotection reaction of a silyl group, (5) a deprotection reaction using a metal, (6) a deprotection reaction using a metal complex etc.

To specifically explain these methods,

The (1) deprotection reaction by alkali hydrolysis is performed, for example, at 0 to 40° C. in an organic solvent (e.g. methanol, tetrahydrofuran, dioxane etc.), using a hydroxide of an alkali metal (e.g. sodium hydroxide, potassium hydroxide, lithium hydroxide etc.), a hydroxide of an alkaline earth metal (e.g. barium hydroxide, calcium hydroxide etc.), or carbonate (e.g. sodium carbonate, potassium carbonate etc.), or an aqueous solution thereof, or a mixture thereof.

The (2) deprotection reaction under the acidic condition is performed, for example, at 0 to 100° C. in an organic solvent (e.g. dichloromethane, chloroform, dioxane, ethyl acetate, methanol, isopropyl alcohol, tetrahydrofuran, anisole etc.), in an organic acid (e.g. acetic acid, trifluoroacetic acid, methanesulfonic acid, p-tosylate etc.), or an inorganic acid (e.g. hydrochloric acid, sulfuric acid etc.) or a mixture thereof (e.g. hydrogen bromide/acetic acid etc.), in the presence or the absence of 2,2,2-trifluoroethanol.

The (3) deprotection reaction by hydrogenation degradation is performed, for example, at 0 to 200° C. in a solvent (e.g. ether-based solvent (e.g. tetrahydrofuran, dioxane, dimethoxyethane, diethyl ether etc.), alcohol-based solvent (e.g. methanol, ethanol etc.), benzene-based solvent (e.g. benzene, toluene etc.), ketone-based solvent (e.g. acetone, methyl ethyl ketone etc.), nitrile-based solvent (e.g. acetonitrile etc.), amide-based solvent (e.g. N,N-dimethylformamide etc.), water, ethyl acetate, acetic acid, or a mixed solvent of two or more of them etc.), in the presence of a catalyst (e.g. palladium-carbon, palladium black, palladium hydroxide-carbon, platinum oxide, Raney nickel etc.) under the hydrogen atmosphere at a normal pressure or under pressure, or in the presence of ammonium formate.

The (4) deprotection reaction of a silyl group is performed, for example, at 0 to 40° C. in an organic solvent which is miscible with water (e.g. tetrahydrofuran, acetonitrile etc.) using tetrabutylammonium fluoride. Alternatively, the reaction is performed, for example, at −10 to 100° C. in an organic acid (e.g. acetic acid, trifluoroacetic acid, methanesulfonic acid, p-tosylate etc.), or an inorganic acid (e.g. hydrochloric acid, sulfuric acid etc.) or a mixture thereof (e.g. hydrogen bromide/acetic acid etc.).

The (5) deprotection reaction using a metal is performed, for example, at 0 to 40° C. in an acidic solvent (e.g. acetic acid, a buffer of pH 4.2 to 7.2, or a mixed solution of any of those solutions and an organic solvent such as tetrahydrofuran etc.) in the presence of a zinc powder, if necessary, while an ultrasound is applied.

The (6) deprotection reaction using a metal complex is performed, for example, at 0 to 40° C. in an organic solvent (e.g. dichloromethane, N,N-dimethylformamide, tetrahydrofuran, ethyl acetate, acetonitrile, dioxane, ethanol etc.), water or a mixed solvent thereof, in the presence of a trap reagent (e.g. tributyltin hydride, triethylsilane, dimedone, morpholine, diethylamine, pyrrolidine etc.), an organic acid (e.g. acetic acid, formic acid, 2-ethylhexanoic acid etc.) and/or an organic acid salt (e.g. sodium 2-ethylhexanoate, potassium 2-ethylhexanoate etc.), in the presence or the absence of a phosphine-based reagent (e.g. triphenylphosphine etc.), using a metal complex (e.g. tetrakistriphenylphosphine-palladium (0), bis(triphenylphosphine)palladium (II) dichloride, palladium (II) acetate, tris(triphenylphosphine)rhodium (I) chloride etc.).

Additionally, in addition to the above reactions, the deprotection reaction can be performed, for example, by the method described in T. W. Greene, Protective Groups in Organic Synthesis, Wiley, New York, 1999.

Examples of the protective group of a hydroxy group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a p-phenylbenzoyl group, a benzyl (Bn) group, a p-methoxybenzyl group, an allyloxycarbonyl (Alloc) group, a 2,2,2-trichloroethoxycarbonyl (Troc) group etc.

Examples of the protective group of an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl(SEM) group etc.

The protective group of a hydroxy group is not particularly limited, as far as it is a group which can be easily and selectively left, in addition to the aforementioned protective groups. Protective groups described in, for example, T. W. Greene, Protective Groups in Organic Synthesis, Wiley, New York, 1999 are used.

The compound represented by the general formula (II) can be produced by the following reaction step formula 2.

[Chemical formula 30]

Reaction step formula 2

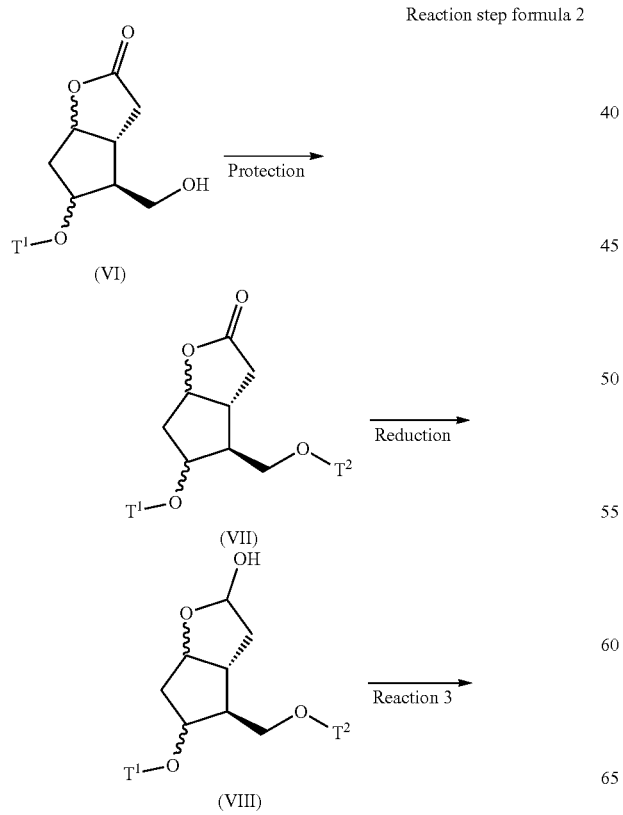

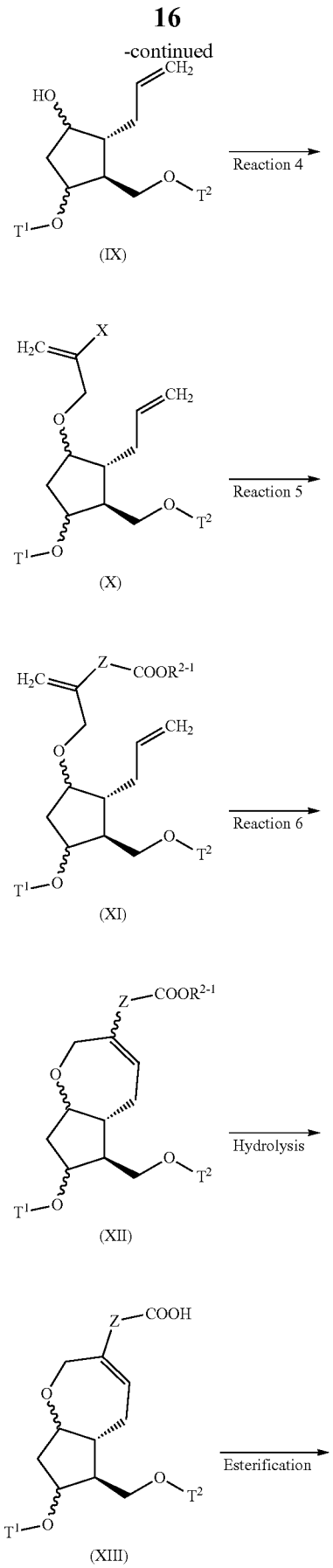

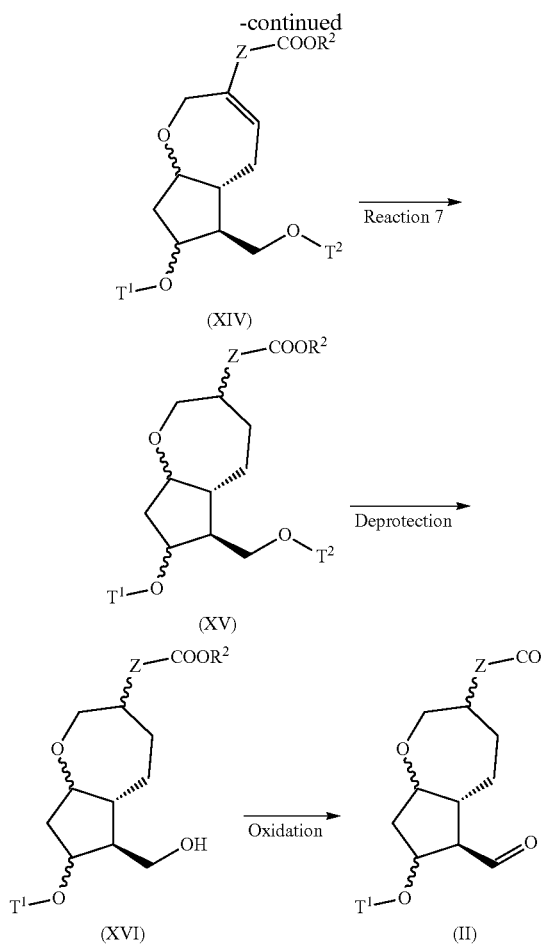

(wherein T² represents a protective group of a hydroxy group (e.g. tert-butyldimethylsilyl (TBDMS) group etc.), X represents a halogen atom or COOR²⁻¹, R²⁻¹ represents the same meaning as that of R², R² and R²⁻¹ may be the same or different, and other symbols represent the same meanings as those described above)

In the reaction step formula 2, the compound represented by the general formula (VII) can be produced by subjecting the compound represented by the general formula (VI) to a protection reaction. For example, the reaction is performed at a temperature of −100 to 50° C. in an organic solvent (e.g. DMF etc.) using a base (e.g. imidazole etc.) employing a silane compound (e.g. trimethylsilane chloride (TESCl), tert-butyldimethylsilane chloride (TBSCl), tert-butyldiphenylsilane chloride (TBDPSCl) etc.).

In the reaction step formula 2, the compound represented by the general formula (VIII) can be produced by subjecting the compound represented by the general formula (VII) to a reducing reaction. For example, the reaction is performed at −78 to 80° C. in an organic solvent (e.g. toluene, ethanol, tetrahydrofuran, hexane etc.) using a reducing agent (e.g. diisobutylaluminum hydride (DIBAL), lithium aluminum hydride etc.).

In the reaction step formula 2, the reaction 3 is known, and is performed, for example, at a temperature of −78 to 50° C. in an organic solvent (e.g. anhydrous toluene, dimethoxyethane, tetrahydrofuran etc.) in the presence of a base (e.g. lithiumhexamethyldisilazane (LHMDS), lithiumdiisopropylamide (LDA), butyllithium, potassium tert-butoxide, sodium hydride etc.) using a Wittig reagent (e.g. methyltriphenylphosphonium bromide etc.).

In the reaction step formula 2, the reaction 4 is known, and is performed, for example, at −50 to 120° C. in an organic solvent (e.g. tetrahydrofuran, DMF, DME, toluene etc.) using a base (e.g. sodium hydride, potassium tert-butoxide, butyllithium, sodium hydroxide etc.) employing alkyl halide (e.g. ethyl 2-(bromomethyl)acrylate, 2,3-dibromopropene etc.).

Herein, when X represents COOR²⁻¹ in the compound of the general formula (X), the objective compound can be produced by subjecting the compound of the general formula (X) as it is to the reaction 6, without via the following reaction 5.

In the reaction step formula 2, the reaction 5 is known, and is performed, for example, at a temperature of room temperature to 120° C. in an organic solvent (e.g. toluene, THF, DMF etc.) in the presence of a palladium catalyst (e.g. bis(tri-tert-butylphosphine)palladium (Pd(P(t-Bu)₃)₂), tetrakis(triphenylphosphine)palladium (Pd(PPh₃)₄), bis(triphenylphosphine)palladium dichloride (PdCl₂(PPh₃)₂) etc.), using an organozinc compound (e.g. a compound represented by the following general formula (X-1):

[Chemical formula 31]

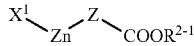

(X-1)

(wherein X¹ represents a halogen atom, and other symbols represent the same meanings as those described above) etc.).

In the reaction step formula 2, the reaction 6 is known, and is performed, for example, a temperature of 20 to 80° C. in an organic solvent (e.g. toluene, dichloromethane, dichloroethane etc.) using a metathesis catalyst (e.g. 2,6-diisopropylphenylimidoneophylidenemorbidenium (VI) bis(tert-butoxide), 2,6-diisopropylphenylimidoneophylidenemorbidenium (VI) bis(hexafluorotert-butoxide) etc.).

In the reaction step formula 2, the compound represented by the general formula (XIII) can be produced by subjecting the compound represented by the general formula (XII) to a hydrolysis reaction. For example, the reaction is performed at 0 to 80° C. in the presence of a hydroxide of an alkali metal (e.g. sodium hydride, potassium hydride, lithium hydride etc.) in a hydrous solvent (e.g. a mixed solvent of an alcohol-based solvent (e.g. methanol, ethanol, propanol, isopropyl alcohol etc.) and water).

In the reaction step formula 2, the compound represented by the general formula (XIV) can be produced by subjecting the compound represented by the general formula (XIII) to an esterification reaction. Examples of the esterification reaction include:

(1) A method using halogenated alkyl,
(2) A method using acid halide,
(3) A method using a mixed acid anhydride,
(4) A method using a condensing agent, etc.

To specifically explain a method using alkyl halide as one example, for example, the method is performed by reacting carboxylic acid with alkyl halide at 0 to 150° C. in an organic solvent (e.g. acetonitrile, acetone, N,N-dimethylformamide, dimethyl sulfoxide, chloroform, dichloromethane, diethyl ether, tetrahydrofuran etc.) in the presence of carbonate (e.g. cesium carbonate, sodium carbonate, potassium carbonate etc.), an organic base (e.g. dimethylformamide, triethylamine, diisopropylethylamine etc) or hydride of an alkyl metal (sodium hydride etc.).

In the reaction step formula 2, the reaction 7 is known, and is performed
(1) by a reaction at 0° C. to 80° C. under the atmospheric pressure or a high pressure using a metal catalyst (e.g. palladium carbon, platinum oxide, rhodium-alumina, Raney nickel, Wilkinson complex, ruthenium catalyst, iridium catalyst etc.) in an organic solvent (e.g. methanol, ethanol, ethyl acetate, dichloromethane, dichloroethane, etc.) using, for example, a hydrogen gas, or
(2) by a reaction at −40 to 80° C. using a reducing agent (e.g. sodium borohydride etc.) in an organic solvent (e.g. methanol, ethanol, etc.) in the presence or the absence of cerium chloride etc. as an additive.

Among products obtained by the reaction 7, after a desired optical isomer is fractionated by optical resolution by a conventional method (e.g. method using optical resolution column), if necessary, the aforementioned protection reaction is performed, thereby, the compound represented by the general formula (XV) can be produced.

Among the reaction step formula 2, the compound represented by the general formula (XVI) can be produced by subjecting the compound represented by the general formula (XV) to the aforementioned deprotection reaction.

In the reaction step formula 2, the compound represented by the general formula (II) can be produced by subjecting the compound represented by the general formula (XVI) to an oxidation reaction. Examples of the oxidation reaction include:
(1) A method using DMSO oxidation (e.g. Swern oxidation),
(2) A method using a Dess-Martin Reagent,
(3) A method using a TEMPO (2,2,6,6-tetramethylpiperidine 1-oxyl) reagent, etc.

To specifically explain the method using DMSO oxidation as one example, for example, the method is performed by reacting an alcohol compound in an organic solvent (e.g. chloroform, dichloromethane, ethyl acetate etc.) in the presence of an activating agent (e.g. oxalyl chloride, acetic acid anhydride, pyridine-sulfur trioxide complex etc.), and an oxidizing agent (e.g. dimethyl sulfoxide etc.) and, further, reacting tertiary amine (e.g. triethylamine, N,N-diisopropylethylamine, N-methylmorpholine, N-ethylpiperidine, diazabicyclo[5.4.0]undec-7-ene etc.) at −78 to 40° C.

In the reaction step formula 2, as the compound having a symbol:

$\sim$, [Chemical Formula 32]

a compound obtained by performing optical resolution by a conventional method (e.g. method using optical resolution column) in advance, and fractionating a desired optical isomer may be used.

In each reaction in the present specification, the compound used as a starting raw material, and the compound represented by the general formula (III) or the general formula (VI) are known, or can be easily produced by the known method.

In each reaction in the present specification, a reaction accompanying heating can be performed using a water bath, an oil bath, a sand bath or a microwave, as is apparent to a person skilled in the art.

In each reaction in the present specification, a solid phase-supported reagent supported on a high-molecular polymer (e.g. polystyrene, polyacrylamide, polypropylene, polyethylene glycol etc.) may be appropriately used.

In each reaction in the present specification, the reaction product can be purified by a normal purification means, for example, a method such as distillation under normal pressure or under reduced pressure, high performance liquid chromatography using silica gel or magnesium silicate, thin layer chromatography, an ion-exchange resin, a scavenger resin, or column chromatography or washing, recrystallization etc. Purification may be performed for every reaction, or may be performed after completion of some reactions.

[Toxicity]

The present invention compound has very low toxicity, has little, for example, eye stimulating property (hyperemia, corneal clouding etc.), aqueous humor protein rise etc., and can be safely used as a medicament.

[Application to Medicament]

Since the present invention compound has selective FP agonist activity, based on its intraocular pressure lowering action, it is useful as an agent for preventing and/or treating an ocular disease, for example, glaucoma (acute closed-angle glaucoma, chronic closed-angle glaucoma, secondary closed-angle glaucoma, primary open-angle glaucoma, secondary open-angle glaucoma, congenital glaucoma, normal pressure glaucoma, aqueous hyperproduction glaucoma, etc.), ocular hypertension, macular edema, macular degeneration, retina and optic nerve tensile force rise, myopia, hyperopia, astigma, dry eye, amotio retinae, cataract, ocular pressure rise due to trauma or inflammation, ocular pressure rise due to a drug such as a steroid or a hormone agent, intraocular pressure rise after operation etc.

In addition, since the present invention compound has FP agonist activity, it is also useful as a labor inducer, an ecbolic, an oxytocic, a therapeutic agent for dysmenorrhea, a therapeutic agent for osteoporosis, a sunburn revulsant, a white hair preventing agent, a hair growth promoter, an eyelash extender, a therapeutic agent for Meniere's disease, a therapeutic agent for a labyrinthian disease etc.

The present invention compound may be administered as a joint use drug, by combining with other drug for:
1) complementing and/or potentiating the preventing and/or treating effect of the compound,
2) improving dynamic state • absorption of the compound, decreasing a dose, and/or
3) alleviating side effect of the compound.

The joint use drug of the present invention compound and other drug may be administered in a form of a compounding agent in which both ingredients are incorporated into one preparation, or may take a form of administration of separate preparations. When administered by formulating into separate preparations, administration by simultaneous administration and time lag is included. In addition, in administration of time lag, the present invention compound may be administered earlier, and other drug may be administered later, or other drug may be administered earlier, and the present invention compound may be administered later. Respective administration methods may be the same or different.

By joint use drug, a disease on which the preventing and/or treating effect is exerted is not particularly limited, but the disease may be a disease on which the preventing and/or treating effect of the preset invention compound is complemented and/or potentiated.

Examples of other drug for complementing and/or potentiating the preventing and/or treating effect on glaucoma of the present invention compound include sympathetic nerve agonists ($\alpha_2$ agonists: e.g. apraclonidine hydrochloride etc., $\beta_2$ agonist: e.g. dipivefrine hydrochloride etc.), parasympathetic nerve agonists (e.g. pilocarpine hydrochloride, carbachol, demecarium, echothiophate or distigmine bromide etc.), sympathetic nerve suppressants ($\alpha_1$ blocker: e.g. bunazosin hydrochloride etc., β blocker e.g. timolol maleate, befunolol hydrochloride, carteolol hydrochloride, or betaxolol hydrochloride etc., $\alpha_1 \beta$ blocker, e.g. levobunolol hydrochloride, nipradilol etc.), prostaglandin drugs (e.g. isopropyl unoprostone, latanoprost, bimatoprost, travoprost, tafluprost, EP2 agonist, EP4 agonist or DP agonist etc.), carbonic anhydrase inhibitors (e.g. acetazolamide, diclofenamide, methazolamide, dorzolamide hydrochloride, or brinzolamide etc.), hyperosmotic agents (e.g. glycerin, preparation incorporating glycerin and fructose, isosorbide, or D-mannitol etc.), ROCK (Rho kinase) inhibitors (e.g. Y-27632 etc.), NMDA antagonists etc.

In addition, the therapeutic agent for glaucoma to be combined with the present invention compound includes not only therapeutic agents which have been found out until now, but also therapeutic agents which will be found out from now on.

The present invention compound is usually administered systemically or locally in an oral or parenteral form. Examples of the oral agent include liquid drugs for internal application (e.g. elixirs, syrups, pharmaceutically acceptable water agents, suspensions, emulsions), solid preparations for internal application (e.g. tablets (including sublingual tablets, orally disintegrating tablets), pills, capsules (including hard capsules, soft capsules, gelatin capsules, microcapsules), powders, granules, torches) etc. Examples of the parenteral agents include solutions (e.g. injectables (subcutaneous injectables, intravenous injectables, intramuscular injectables, intraperitoneal injectables, infusions etc.), eye drops (e.g. aqueous eye drops (aqueous eye drops, aqueous suspensions eye drops, viscous eye drops, solubilized eye drops etc.), nonaqueous eye drops (nonaqueous eye drops, nonaqueous suspension eye drops etc.)) etc.), external preparations (e.g. ointment (ocular ointment etc.)), ear drops etc. These preparations may be release-controlled agents such as rapid-releasing preparations and sustained-release preparations. These preparations can be produced by the known method, for example, the method described in Japanese Pharmacopoeia etc.

Solutions for internal application as the oral agent are produced by dissolving, suspending or emulsifying an active ingredient in a diluent which is generally used (e.g. purified water, ethanol or a mixed solution thereof etc.). Further, this solution may contain wetting agents, suspending agents, emulsifiers, sweeteners, flavors, aromatic agents, preservatives, buffers etc.

Solid preparations for internal application as the oral agent are formulated into preparations according to a conventional method by mixing an active ingredient with excipients (e.g. lactose, mannitol, glucose, microcrystalline cellulose, starch etc.), binders (e.g. hydroxypropylcellulose, polyvinylpyrrolidone, magnesium aluminometasilicate etc.), disintegrating agents (e.g. cellulose calcium glycolate etc.), lubricants (e.g. magnesium stearate etc.), stabilizers, solubilizers (glutamic acid, aspartic acid etc.) etc. In addition, if necessary, preparations may be covered with coating agents (e.g. white sugar, gelatin, hydroxypropylcellulose, hydroxypropylmethylcellulose phthalate etc.), or may be covered with two or more layers.

The external preparation as the parenteral agent is produced by the known method, or formulation which is usually used. For example, the ointment preparations are produced by kneading an active ingredient in a base or melting an active ingredient in a base. An ointment base is selected from bases which are known, or are usually used. For example, an ointment base selected from higher fatty acids or higher fatty acid esters (e.g. adipic acid, myristic acid, palmitic acid, stearic acid, oleic acid, adipic acid ester, myristic acid ester, palmitic acid ester, stearic acid ester, oleic acid ester, etc.), waxes (e.g. beewax, whale wax, ceresin etc.), surfactants (e.g. polyoxyethylene alkyl ether phosphoric acid ester etc.), higher alcohols (e.g. cetanol, stearyl alcohol, cetostearyl alcohol etc.), silicone oils (e.g. dimethylpolysiloxane etc.), hydrocarbons (e.g. hydrophilic vaseline, white vaseline, purified lanolin, liquid paraffin etc., glycols (e.g. ethylene glycol, diethylene glycol, propylene glycol, polyethylene glycol, macrogol etc.), vegetable oils (e.g. castor oil, olive oil, sesame oil, turpentine oil etc.), animal oils (e.g. mink oil, yolk oil, squalane, squalene etc.), water, absorption promoter, and rash preventing agents, alone, is used, or a mixture of two or more kinds is used. Further, the ointment base may contain humectants, preservatives, stabilizers, antioxidants, coloring agents etc.

The injectable as the parenteral agent includes solutions, suspensions, emulsions and solid injectables which are used by dissolving or suspending a solid in a solvent upon use. The injectable is used, for example, by dissolving, suspending or emulsifying an active ingredient in a solvent. As the solvent, for example, distilled water for injection, physiological saline, vegetable oil, alcohols such as propylene glycol, polyethylene glycol and ethanol etc., and a combination thereof are used. Further, this injectable may contain stabilizers, solubilizers (e.g. glutamic acid, aspartic acid, polysorbate 80 (registered trademark) etc.), suspending agents, emulsifiers, soothing agents, buffers, preservatives etc. These are produced by sterilization in a final step, or by a sterilization operation method. Alternatively, a sterile solid agent, for example, a lyophilized product is produced, and it can be also used by sterilization before use thereof, or can be also used by dissolving the product in sterile distilled water for injection or other solvent.

Examples of a preferable dosage form of the present invention compound include eye drops, ocular ointments, tablets etc., and more preferable is eye drops or ocular ointment. These can be formulated into preparations using the generally used technique. For example, in the case of eye drops, as additives, tonicity agents, buffers, pH adjusting agents, solubilizers, thickeners, stabilizers, preservatives etc. can be appropriately incorporated. Alternatively, stable eye drops can be also obtained by adding pH adjusting agents, thickeners, or dispersants, and suspending drugs.

Examples of the tonicity agent include glycerin, propylene glycol, sodium chloride, potassium chloride, sorbitol, mannitol, etc.

Examples of the buffer include phosphoric acid, phosphate, citric acid, acetic acid, s-aminocaproic acid etc.

Examples of the pH adjusting agent include hydrochloric acid, citric acid, phosphoric acid, acetic acid, sodium hydroxide, potassium hydroxide, boric acid, borax, sodium carbonate, sodium bicarbonate etc.

Examples of the solubilizer include polysorbate 80, polyoxyethylene hardened castor oil 60, macrogol 4000 etc.

Examples of the thickener and dispersant include cellulose-based polymers such as hydroxypropylmethylcellulose and hydroxypropylcellulose, polyvinyl alcohol, polyvinylpyrrolidone etc., and examples of the stabilizer include edetic acid and sodium edetate etc.

Examples of the preservative (antiseptic agent) include general-use sorbic acid, potassium sorbate, benzalkonium chloride, benzethonium chloride, methyl paraoxybenzoate, propyl paraoxybenzoate, chlorobutanol etc., and these preservatives can be also used by combining them.

In eye drops containing the active ingredient of the present invention, it is desirable that a pH is set at 4.0 to 8.5, and it is desirable that an osmotic pressure ratio is set at around 1.0.

A dose of the active ingredient of the present invention can be appropriately selected depending on a symptom, an age, a dosage form etc. and, in the case of the oral agent, preferably 1 to 1000 mg, more preferably 5 to 300 mg may be administered once to a few times (e.g. once to three times) per day. In the case of eye drops, one to a few drops having a concentration of preferably 0.000001 to 5% (w/v), more preferably 0.00001 to 0.05% (w/v) as a one time amount may be administered to eyes once to a few times (e.g. once to eight times) per day. In addition, in the case of the ocular ointment, an ocular ointment having a concentration of preferably 0.000001 to 5% (w/w), more preferably 0.00001 to 0.05% (w/w) may be coated once to a few times (e.g. once to four times) per day.

Of course, since a dose varies depending on a variety of conditions as described above, an amount smaller than the aforementioned dose is sufficient in some cases, or an amount exceeding the range is necessary in some cases.

EXAMPLES

The present invention will be described in detail below by way of Examples, but the present invention is not limited by them.

A solvent in a parenthesis shown in a place of separation by chromatography and TLC indicates an eluting solvent or a developing solvent used, and a ratio represents a volumetric ratio.

NMR data is data of $^1$H-NMR unless otherwise is indicated.

A solvent used in measurement is indicated in a parenthesis shown at a place of NMR.

A compound name used in the present specification was generally named by using a computer program, ACD/Name (registered trademark) of Advanced Chemistry Development, which performs naming according to a rule of IUPAC, or according to IUPAC nomenclature.

Example 1

(3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one To a dimethylformamide (hereinafter, abbreviated as DMF in some cases) (100 mL) solution of (3aR,4S,5R,6aS)-4-(hydroxymethyl)-5-(tetrahydro-2H-pyran-2-yloxy)hexahydro-2H-cyclopenta[b]furan-2-one (50 g) were sequentially added imidazole (29.22 g), and tert-butyldimethylchlorosilane (30.87 g) under ice-cooling, and the mixture was stirred at room temperature for 3.5 hours. After completion of the reaction, a small amount of ethanol was added, the reaction solution was poured into ice water, and this was extracted with ethyl acetate:hexane (2:3). The extract was washed with 1N hydrochloric acid, an aqueous saturated sodium bicarbonate solution, water and a saturated saline, dried with sodium sulfate, and concentrated under reduced pressure to obtain a titled compound (76.2 g) having the following physical property values.

TLC: Rf 0.42 (hexane:ethyl acetate=3:1).

Example 2

(3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-ol Under the argon atmosphere, an anhydrous toluene (390 mL) solution of the compound (76.2 g) produced in Example 1 was cooled to −70° C., a 1 mol/L toluene solution (212.4 mL) of diisobutylaluminum hydride was added dropwise over about 1 hour, and mixture was stirred for 30 minute as it was. After completion of the reaction, the reaction solution was diluted with tert-butyl methyl ether (hereinafter, abbreviated as MTBE in some cases) (400 mL), and an aqueous saturated sodium sulfate solution was added. The precipitated white precipitate was filtered with Celite (trade name), and the solvent was concentrated under reduced pressured to obtain a titled compound (80.7 g) having the following physical property values.

TLC: Rf 0.30 (hexane:ethyl acetate=3:1).

Example 3

(1S,2R,3S,4R)-2-allyl-3-({[dimethyl(2-methyl-2-propanyl)silyl]oxy}methyl)-4-(tetrahydro-2H-pyran-2-yloxy)cyclopentanol Under the argon atmosphere, a 1.6M tetrahydrofuran (hereinafter, abbreviated as THF in some cases) solution (500 mL) of lithiumhexamethyldisilazane was added dropwise to an anhydrous toluene (300 mL) suspension of methyltriphenylphosphonium bromide (326.6 g) under ice-cooling, and the mixture was stirred at room temperature for 1 hour. The mixture was cooled to −70° C. again, an anhydrous toluene (400 mL) solution of the compound (85.2 g) produced in Example 2 was added dropwise over about 1.5 hours, and the mixture was stirred at room temperature for 2 hours. After completion of the reaction, an aqueous ammonium chloride solution was added, followed by extraction with ethyl acetate. The organic layer was washed with water and a saturated saline, and dried with sodium sulfate, and the solvent was concentrated under reduced pressure. The resulting residue was purified with a column apparatus (Hiflash-SI, Size 5 L×4, hexane:ethyl acetate=100:0→85:15→75:25) manufactured by Yamazen Corporation to obtain a titled compound (41.87 g) having the following physical property values.

TLC: Rf 0.57 (hexane:ethyl acetate=3:1).

Example 4

{[(1S,2R,3S,5R)-2-allyl-3-[(2-bromo-2-propen-1-yl)oxy]-5-(tetrahydro-2H-pyran-2-yloxy)cyclopentyl]methoxy}(dimethyl)(2-methyl-2-propanyl)silane Under the argon atmosphere, 2,3-dibromopropene (8.4 mL, 81.0 mmol) was placed into a flask, and this was cooled to an inner temperature of 5° C. using ice water. Sodium hydride (2.16 g, 54.1 mmol) was placed therein, and the mixture was stirred for 5 minutes. The compound (10 g, 27 mmol) produced in Example 3 was added dropwise over 50 minutes, and the mixture was stirred at room temperature for 2 hours. The reaction solution was carefully poured into an aqueous saturated ammonium chloride solution, and this was extracted with MTBE, washed with an aqueous saturated ammonium chloride solution, dried with anhydrous sodium sulfate, and concentrated. Purification with silica gel column chromatography (hexane:ethyl acetate=95:5→80:20) afforded a titled compound (10.9 g) having the following physical property values.

TLC: Rf 0.72 hexane:ethyl acetate=9:1).

Example 5

Ethyl 5-({[(1S,2R,3S,4R)-2-allyl-3-({[dimethyl(2-methyl-2-propanyl)silyl]oxy}methyl)-4-(tetrahydro-2H-pyran-2-yloxy)cyclopentyl]oxy}methyl)-5-hexanoate Under the argon atmosphere, the compound (10.9 g, 22.2 mmol) produced in Example 4 was dissolved in toluene (100 mL), and 4-ethoxy-4-oxobutylzinc bromide (0.5 mol/L THF solution, 133 mL, 66.7 mmol) was added at room temperature. Bis(tri-tert-butylphosphine)palladium (567 mg, 1.11 mmol) was added, and the mixture was stirred at 80° C. for 2 hours. This was cooled to room temperature, an aqueous saturated ammonium chloride solution was added, and this was concentrated. The resulting residue was dissolved in MTBE, and this was filtered using Celite (trade name). The filtrate was washed with an aqueous ammonium chloride solution, an aqueous saturated sodium bicarbonate solution, and a saturated saline, dried with magnesium sulfate, and concentrated. Purification with silica gel column chromatography (hexane:ethyl acetate=90:10→50:50) to obtain a titled compound (9.73 g) having the following physical property values.

TLC: Rf 0.65 (hexane:ethyl acetate=9:1).

Example 6

Ethyl 4-[(5aR,6S,7R,8aS)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-yl]butanoate Under the argon-atmosphere, the compound (400 mg, 0.762 mmol) produced in Example 5 was dissolved in toluene (76 mL). A Schrock's catalyst (2,6-diisopropylphenylimidoneophylidenemorbidenium (VI) bis(hexafluorotert-butoxide)) (785 mg, 0.925 mmol) was added to perform a reaction at 85° C. for 18 hours. After allowing to cool, the reaction was concentrated, and purified by silica gel column chromatography (hexane:ethyl acetate=90:10→50:50) to obtain a titled compound (4.8 mg) having the following physical property values.

TLC: Rf 0.47 (hexane:ethyl acetate=4:1).

Example 7

4-[(5aR,6S,7R,8aS)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-yl]butanoic acid The compound (7.63 g, 15.4 mmol) produced in Example 6 was dissolved in ethanol (60 mL), a 2.0 mol/L aqueous sodium hydroxide solution (20 mL) was added, and the mixture was stirred at room temperature for 2 hours. The reaction was concentrated, and ethyl acetate and 2 mol/L hydrochloric acid were added, followed by extraction. The extract was washed with a saturated saline, dried with anhydrous sodium sulfate, and concentrated. The resulting titled compound was used in a next reaction without purification.

TLC: Rf 0.48 (chloroform:methanol=9.1)

Example 8

2-Propanyl 4-[(5aR,6S,7R,8aS)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-yl]butanoate Under the argon atmosphere, the compound (15.4 mmol) produced in Example 8 was dissolved in DMF, potassium carbonate (5.31 g, 38.5 mmol) and isopropyl iodide (2.31 mL, 23.1 mmol) were added, and the mixture was stirred at 60° C. for 3 hours. After cooling, MTBE and water were added, and this was extracted, washed with a saturated saline, dried with anhydrous sodium sulfate, and concentrated. Purification by silica gel column chromatography (hexane:ethyl acetate=90:10→50:50) afforded a titled compound (7.25 g) having the following physical property values.

TLC: Rf 0.90 (ethyl acetate).

Example 9

2-Propanyl 4-[(5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]butanoate Under the argon atmosphere, a dichloromethane solution (62 mL) of the compound (4.85 g, 9.45 mmol) produced in Example 8 was degassed using an ultrasound, and argon replacement was performed. A Crabtree's catalyst (tricyclohexylphosphine) (1,5-cyclooctadiene) (pyridine)iridium (I) hexafluorophosphate) (760 mg, 0.945 mmol) was added, and the mixture was stirred at room temperature for 3 hours and 50 minutes under the hydrogen atmosphere. The solution was concentrated under reduced pressure, and purified with a column apparatus (Hiflash-SI, Size 2 L, hexane→ethyl acetate:hexane=3:7) manufactured by Yamazen Corporation to obtain a titled compound (3.05 g) having the following physical property values.

TLC: Rf 0.72 (hexane:ethyl acetate=1:2).

Example 10 (1)

2-Propanyl 4-[(3S,5aR,6S,7R,8aS)-6-({[dimethyl(2-methyl-2-propanyl)silyl]oxy}methyl)-7-hydroxyoctahydro-2H-cyclopenta[b]oxepin-3-yl]butanoate Example 10 (2)

2-Propanyl 4-[(3R,5aR,6S,7R,8aS)-6-({[dimethyl(2-methyl-2-propanyl)silyl]oxy}methyl)-7-hydroxyoctahydro-2H-cyclopenta[b]oxepin-3-yl]butanoate Under the argon atmosphere, a dichloromethane solution (60 mL) of the compound (3.02 g, 5.89 mmol) produced in Example 9 was cooled to −20° C. A dimethylaluminum chloride solution (1.0M hexane solution) was added, and the mixture was stirred for 3 hours and 40 minutes while a temperature was raised to room temperature. The reaction solution was poured into an ice-cooled aqueous saturated sodium bicarbonate solution, a Rochelle salt was added, and the mixture was stirred for 40 minutes. The aqueous layer was extracted with ethyl acetate two times, and the collected organic layers were washed with a saturated saline, and dried with anhydrous sodium sulfate. The solution was concentrated under reduced pressure, and purified with a column apparatus (Hiflash-SI, Size 5 L, toluene:acetone=10:1) manufactured by Yamazen Corporation once, and with (Hiflash-SI, Size 2 L+YAMAZEN ULTRA PACK SI-C, Size 37×300, toluene:acetone=10:1) two times to obtain a compound (1.60 g) of Example 10 (1) and a compound (810 mg) of Example 10 (2) having the following physical property values.

TLC: Rf 0.30 (toluene:acetone=9:1) (compound of Example 10 (1));

TLC: Rf 0.31 (toluene:acetone=9:1) (compound of Example 10 (2)).

Example 11

2-Propanyl 4-[(3S,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]butanoate Under the argon atmosphere, 3,4-dihydro-2H-pyran (403 µL, 4.42 mmol) and tosic acid monohydrate (10 mg, 0.111 mmol) were added to a toluene solution (1.85 mL) of the compound (1.58 g, 3.69 mmol) produced in Example 10 (1), and the mixture was stirred at room temperature for 15 minutes. Tosic acid monohydrate (10 mg, 0,111 mmol) was added, the mixture was stirred for 45 minutes, triethylamine (100 µL) was added, and the reaction solution was concentrated under reduced pressure. Purification with a column apparatus (Hiflash-SI, Size 2 L, hexane→ethyl acetate:hexane=3:7) manufactured by Yamazen Corporation to obtain a titled compound (1.82 g) having the following physical property values.

TLC: Rf 0.46 (hexane:ethyl acetate=1:1).

Example 12

2-Propanyl 4-[(3S,5aR,6S,7R,8aS)-6-(hydroxymethyl)-7-(tetrahydro-2H-pyran-2-yloxy)octahydro-2H-cyclopenta[b]oxepin-3-yl]butanoate Under the argon atmosphere, tetrabutylammonium fluoride (7 mL, 1.0M THF solution) was added to a THF solution (3.6 mL) of the compound (1.81 g, 3.53 mmol) produced in Example 11, and the mixture was stirred at room temperature for 70 minutes. Tetrabutylammonium fluoride (3.5 mL, 1.0 mol/L THF solution) was added, and the mixture was further stirred at 45° C. for 100 minutes. The reaction solution was diluted with ethyl acetate (100 mL), washed with an aqueous saturated ammonium chloride solution once, and with an aqueous saturated sodium chloride solution once, and dried with anhydrous sodium sulfate. The solution was concentrated under reduced pressure, and purified with column apparatus (Hiflash-SI, Size L, ethyl acetate:hexane=2:8→ethyl acetate:hexane=8:2) manufactured by Yamazen Corporation to obtain a titled compound (1.21 g) having the following physical property values.

TLC: Rf 0.40 (hexane:ethyl acetate=1:2).

Example 13

2-Propanyl 4-[(3S,5aR,6R,7R,8aS)-6-formyl-7-(tetrahydro-2H-pyran-2-yloxy)octahydro-2H-cyclopenta[b]oxepin-3-yl]butanoate Under the argon-atmosphere, dimethyl sulfoxide (hereinafter, abbreviated as DMSO in some cases) (1.8 mL) and diisopropylethylamine (1.8 mL, 10.56 mmol) were added to an ethyl acetate solution (4 mL) of the compound (623 mg, 1.76 mmol) produced in Example 12, and the mixture was cooled to 0° C. A pyridine-sulfur trioxide complex (840 mg, 5.28 mmol) was added, and the mixture was stirred at 0° C. for 40 minutes. The reaction solution was diluted with ethyl acetate, and poured into ice-cooled hydrochloric acid (0.5 N). The aqueous layer was extracted with ethyl acetate once, and the collected organic layers were washed with an aqueous saturated sodium bicarbonate solution once, and with a saturated saline, and dried with anhydrous sodium sulfate. The solution was concentrated under reduced pressure to obtain a crude product (634 mg) of a titled compound having a following physical property values.

TLC: Rf 0.73 (hexane:ethyl acetate=2:1).

Example 14

2-Propanyl 4-[(3S,5aR,6R,7R,8aS)-6-[(1E)-3-oxo-4-phenoxy-1-buten-1-yl]-7-(tetrahydro-2H-pyran-2-yloxy)octahydro-2H-cyclopenta[b]oxepin-3-yl]butanoate Under the argon atmosphere, dimethyl-(3-phenoxy-2-oxopropyl)-phosphonate (826 mg, 3.20 mmol) and potassium phosphate (679 mg, 3.20 mmol) were added to a THF solution (16 mL) of the compound (634 mg, 1.60 mmol) produced in Example 13, and the mixture was stirred at room temperature for one day. The reaction solution was added to an aqueous saturated ammonium chloride solution, and the aqueous layer was extracted with ethyl acetate two times. The collected organic layers were washed with a saturated saline, and dried with anhydrous sodium sulfate. The solution was concentrated under reduced pressure, and purified with a column apparatus (Hiflash-SI, Size L, hexane→ethyl acetate:hexane=4:6) manufactured by Yamazen Corporation to obtain a titled compound (426 mg) having the following physical property values.

TLC: Rf 0.55 (hexane:ethyl acetate=1:1).

Example 15

2-Propanyl 4-[(3S,5aR,6R,7R,8aS)-6-[(1E,3R)-3-hydroxy-4-phenoxy-1-buten-1-yl]-7-(tetrahydro-2H-pyran-2-yloxy)octahydro-2H-cyclopenta[b]oxepin-3-yl]butanoate (R)-2-methyl-CBS-oxazaborolidine (65 µL, 1 mol/L toluene solution, 0.065 mmol) was added to a THF solution (16 mL) of the compound (137 mg, 0.259 mmol) produced in Example 14. A borane dimethyl sulfide complex (155 µL, 1 mol/L toluene solution, 0.155 mmol) was added dropwise. After stirred at room temperature for 45 minutes, the solution was diluted with ethyl acetate, and poured into an aqueous saturated ammonium chloride solution. The aqueous layer was extracted with ethyl acetate two times, and the collected organic layers were washed with a saturated saline, and dried with anhydrous sodium sulfate. The resulting solution was concentrated under reduced pressure to obtain a crude product (151 mg) of a titled compound having the following physical property values.

TLC: Rf 0.32 (hexane:ethyl acetate=2:1).

Example 16 (1)

2-Propanyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate

[Chemical formula 33]

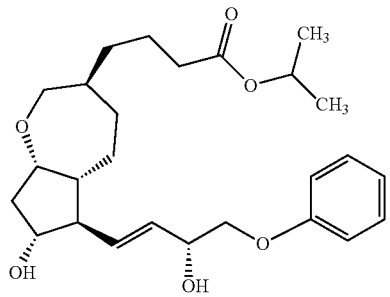

THF (400 µL) and water (400 µL) were added to an acetic acid solution (800 µL) of the compound (151 mg, 0.259 mmol) produced in Example 15, and the mixture was stirred at 60° C. for 3 hours and 30 minutes. The reaction solution was concentrated under reduced pressure, and purified with a column apparatus (Hiflash-SI, Size S, ethyl acetate:hexane=1:1→ethyl acetate) manufactured by Yamazen Corporation to obtain a titled compound (74 mg) having the following physical property values. TLC: Rf 0.28 (dichloromethane: methanol=20:1);
$^1$H-NMR (300 MHz, CDCl$_3$): δ 0.90-1.19, 1.22, 1.36-1.83, 1.84-1.96, 2.03-2.18, 2.23, 2.41-2.53, 2.57, 2.84-2.97, 3.64-3.80, 3.83-3.91, 3.92-4.09, 4.44-4.59, 4.88-5.09, 5.53-5.77, 6.83-7.04, 7.14-7.35.

Example 16 (2) to Example 16 (42)

Using (3aR,4S,5R,6aS)-4-({[dimethyl(2-methyl-2-propanyl)silyl]oxy}methyl)-5-(tetrahydro-2H-pyran-2-yloxy) hexahydro-2H-cyclopenta[b]furan-2-one, using 4-ethoxy-4-oxobutylzinc bromide or a corresponding organozinc reagent in place of it, and using dimethyl-(3-phenoxy-2-oxopropyl)-sulfonate or a corresponding phosphonic acid salt in place of it, those substances were subjected to the same objective operations as those of Example 1→Example 2→Example 3→Example 4→Example 5→Example 6→Example 7→Example 8→Example 9→Example 10 (1) or Example 10 (2)→Example 11→Example 12→Example 13→Example 14→Example 15→Example 16 (1) to obtain the following Example compounds.

Example 16 (2)

2-Propanyl 4-{(3S,5aR,6R,7R,8aS)-7-hydroxy-6-[(1E,3S)-3-hydroxy-5-phenyl-1-penten-1-yl]octahydro-2H-cyclopenta[b]oxepin-3-yl}butanoate TLC: Rf 0.41 (ethyl acetate);
$^1$H-NMR (300 MHz, CDCl$_3$): δ 0.87-1.19, 1.22, 1.34-1.98, 2.00-2.14, 2.23, 2.39-2.54, 2.59-2.80, 2.84-2.97, 3.59-3.78, 3.88-4.23, 4.90-5.09, 5.37-5.51, 5.53-5.65, 7.10-7.24, 7.23-7.38.

Example 16 (3)

2-Propanyl 4-{(3S,5aR,6R,7R,8aS)-6-[(1E,3R)-4-(3-chlorophenoxy)-3-hydroxy-1-buten-1-yl]-7-hydroxy-octahydro-2H-cyclopenta[b]oxepin-3-yl}butanoate

[Chemical formula 34]

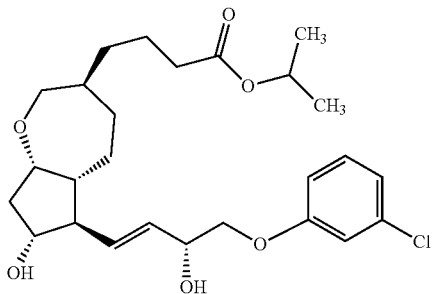

TLC: Rf 0.48 (ethyl acetate);
$^1$H-NMR (300 MHz, CDCl$_3$): δ 0.88-1.19, 1.22, 1.35-1.96, 2.02-2.16, 2.23, 2.41-2.55, 2.56-2.69, 2.82-3.00, 3.63-3.79, 3.81-4.12, 4.42-4.55, 4.89-5.08, 5.54-5.72, 6.77-6.84, 6.91-6.98, 7.20.

Example 16 (4)

2-Propanyl 4-{(3S,5aR,6R,7R,8aS)-7-hydroxy-6-[(1E,3R)-3-hydroxy-4-(3-methylphenoxy)-1-buten-1-yl]octahydro-2H-cyclopenta[b]oxepin-3-yl}butanoate TLC: Rf 0.45 (ethyl acetate);
$^1$H-NMR (300 MHz, CDCl$_3$): δ 0.89-1.29, 1.35-1.97, 2.01-2.17, 2.23, 2.28-2.40, 2.42-2.54, 2.66-2.83, 2.83-2.97, 3.62-3.78, 3.78-4.12, 4.40-4.56, 4.89-5.08, 5.54-5.73, 6.64-6.75, 6.78, 7.16.

Example 16 (5)

Ethyl 4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoate TLC: Rf 0.19 (hexane:ethyl acetate=1:2);
$^1$H-NMR (300 MHz, CDCl$_3$): δ 1.32-1.43, 1.50-1.81, 1.80-2.11, 2.11-2.28, 2.41-2.60, 2.99, 3.28, 3.71-3.85, 3.84-3.94, 4.01, 4.05-4.18, 4.35, 4.48-4.62, 5.60-5.80, 6.85-7.03, 7.16-7.36, 7.90-8.02.

Example 16 (6)

Ethyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoate TLC: Rf 0.22 (hexane:ethyl acetate=1:2);
$^1$H-NMR (300 MHz, CDCl$_3$): δ 1.33-1.43, 1.46-1.96, 1.96-2.10, 2.11-2.43, 2.43-2.58, 2.58-2.78, 2.93-3.13, 3.66-4.18, 4.25, 4.30-4.42, 4.49, 5.54-5.77, 6.83-7.02, 7.17-7.33, 7.41-7.50, 7.92-8.01.

Example 16 (7)

Ethyl 3-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoate TLC: Rf 0.56 (ethyl acetate);
$^1$H-NMR (300 MHz, CDCl$_3$): δ 1.39, 1.53-2.32, 2.43-2.66, 2.91-3.11, 3.30, 3.69-3.84, 3.85-3.95, 3.97-4.05, 4.05-4.18, 4.37, 4.48-4.60, 5.60-5.79, 6.84-7.04, 7.19-7.43, 7.80-7.93.

Example 16 (8)

Ethyl 3-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoate TLC: Rf 0.59 (ethyl acetate);
$^1$H-NMR (300 MHz, CDCl$_3$): δ 1.34-1.43, 1.47-1.95, 1.95-2.12, 2.15-2.33, 2.40-2.58, 2.66-3.19, 3.64-3.99, 4.02-4.14, 4.22, 4.30-4.42, 4.43-4.54, 5.53-5.72, 6.81-7.00, 7.19-7.30, 7.32-7.42, 7.60-7.69, 7.84-7.92, 7.94-8.01.

Example 16 (9)

2-Propanyl 4-{(3S,5aR,6R,7R,8aS)-6-[(1E,3R)-4-(4-chlorophenoxy)-3-hydroxy-1-buten-1-yl]-7-hydroxy-octahydro-2H-cyclopenta[b]oxepin-3-yl}butanoate TLC: Rf 0.44 (ethyl acetate);
$^1$H-NMR (300 MHz, CDCl$_3$): δ 0.87-1.19, 1.22, 1.32-1.97, 2.01-2.17, 2.23, 2.40-2.56, 2.70-2.99, 2.99-3.24, 3.59-3.77, 3.80-4.11, 4.38-4.56, 4.88-5.08, 5.52-5.70, 6.75-6.91, 7.18-7.25.

Example 16 (10)

2-Propanyl 4-{(3S,5aR,6R,7R,8aS)-7-hydroxy-6-[(1E,3R)-3-hydroxy-4-(4-methylphenoxy)-1-buten-1-yl]octahydro-2H-cyclopenta[b]oxepin-3-yl}butanoate TLC: Rf 0.49 (ethyl acetate);
$^1$H-NMR (300 MHz, CDCl$_3$): δ 0.90-1.18, 1.22, 1.37-1.83, 1.83-1.95, 2.01, 2.05-2.17, 2.23, 2.29, 2.40-2.56, 2.84-2.97, 3.66-3.79, 3.84, 3.90-4.09, 4.50, 4.91-5.07, 5.57-5.73, 6.76-6.85, 7.03-7.12.

Example 16 (11)

2-Propanyl 4-[(3S,5aR,6R,7R,8aS)-7-hydroxy-6-{(1E,3R)-3-hydroxy-4-[4-(trifluoromethyl)phenoxy]-1-buten-1-yl}octahydro-2H-cyclopenta[b]oxepin-3-yl]butanoate TLC: Rf 0.47 (ethyl acetate);
$^1$H-NMR (300 MHz, CDCl$_3$): δ 0.90-1.19, 1.21, 1.36-1.96, 2.06-2.29, 2.41-2.68, 2.91, 3.66-3.79, 3.88-4.10, 4.48-4.60, 4.90-5.08, 5.57-5.76, 6.97, 7.54.

Example 16 (12)

2-Propanyl 4-{(3S,5aR,6R,7R,8aS)-6-[(1E,3R)-4-(2-fluorophenoxy)-3-hydroxy-1-buten-1-yl]-7-hydroxyoctahydro-2H-cyclopenta[b]oxepin-3-yl}butanoate TLC: Rf 0.53 (ethyl acetate);
$^1$H-NMR (300 MHz, CDCl$_3$): δ 0.85-1.19, 1.22, 1.34-1.96, 2.03-2.18, 2.18-2.29, 2.39-2.57, 2.71-2.84, 2.84-2.99, 3.63-3.80, 3.85-4.13, 4.47-4.61, 4.88-5.09, 5.55-5.77, 6.84-7.15.

Example 16 (13)

2-Propanyl 4-{(3S,5aR,6R,7R,8aS)-6-[(1E,3R)-4-(3-fluorophenoxy)-3-hydroxy-1-buten-1-yl]-7-hydroxyoctahydro-2H-cyclopenta[b]oxepin-3-yl}butanoate TLC: Rf 0.55 (ethyl acetate);
$^1$H-NMR (300 MHz, CDCl$_3$): δ 0.91-1.19, 1.22, 1.34-1.97, 1.99-2.20, 2.23, 2.37-2.60, 2.91, 3.65-3.79, 3.81-4.12, 4.45-4.60, 4.91-5.10, 5.56-5.75, 6.59-6.74, 7.11-7.32.

Example 16 (14)

2-Propanyl 4-{(3S,5aR,6R,7R,8aS)-6-[(1E,3R)-4-(4-fluorophenoxy)-3-hydroxy-1-buten-1-yl]-7-hydroxyoctahydro-2H-cyclopenta[b]oxepin-3-yl}butanoate TLC: Rf 0.55 (ethyl acetate);
$^1$H-NMR (300 MHz, CDCl$_3$): δ 0.90-1.18, 1.22, 1.36-1.98, 1.99-2.18, 2.23, 2.40-2.68, 2.84-2.97, 3.64-3.79, 3.79-3.89, 3.89-4.14, 4.44-4.57, 4.89-5.11, 5.56-5.75, 6.80-6.91, 6.91-7.03.

Example 16 (15)

2-Propanyl 4-[(3S,5aR,6R,7R,8aS)-7-hydroxy-6-{(1E,3R)-3-hydroxy-4-[3-(trifluoromethyl)phenoxy]-1-buten-1-yl}octahydro-2H-cyclopenta[b]oxepin-3-yl]butanoate TLC: Rf 0.46 (ethyl acetate);
$^1$H-NMR (300 MHz, CDCl$_3$): δ 0.90-1.19, 1.19-1.25, 1.36-1.97, 2.00-2.19, 2.23, 2.41-2.56, 2.85-2.98, 3.67-3.80, 3.88-4.09, 4.48-4.60, 4.91-5.08, 5.59-5.76, 7.09, 7.12-7.17, 7.21-7.25, 7.40.

Example 16 (16)

2-Propanyl 4-{(3S,5aR,6R,7R,8aS)-7-hydroxy-6-[(1E,3R)-3-hydroxy-4-(3-methoxyphenoxy)-1-buten-1-yl]octahydro-2H-cyclopenta[b]oxepin-3-yl}butanoate TLC: Rf 0.43 (ethyl acetate);
$^1$H-NMR (300 MHz, CDCl$_3$): δ 0.89-1.18, 1.81-1.26, 1.35-1.97, 2.02-2.19, 2.23, 2.40-2.60, 2.83-2.98, 3.63-4.10, 4.45-4.58, 4.89-5.08, 5.56-5.74, 6.43-6.58, 7.17.

Example 16 (17)

2-Propanyl 4-{(3S,5aR,6R,7R,8aS)-7-hydroxy-6-[(1E,3R)-3-hydroxy-4-(4-methoxyphenoxy)-1-buten-1-yl]octahydro-2H-cyclopenta[b]oxepin-3-yl}butanoate TLC: Rf 0.44 (ethyl acetate);
$^1$H-NMR (300 MHz, CDCl$_3$): δ 0.89-1.18, 1.23, 1.35-1.96, 2.04-2.29, 2.40-2.55, 2.61, 2.84-2.97, 3.64-3.87, 3.89-4.09, 4.43-4.55, 4.91-5.06, 5.56-5.73, 6.75-6.92.

Example 16 (18)

2-Propanyl 4-{(3S,5aR,6R,7R,8aS)-7-hydroxy-6-[(1E,3R)-3-hydroxy-4-(2-methylphenoxy)-1-buten-1-yl]octahydro-2H-cyclopenta[b]oxepin-3-yl}butanoate TLC: Rf 0.50 (ethyl acetate);
$^1$H-NMR (300 MHz, CDCl$_3$): δ 0.85-1.19, 1.19-1.26, 1.33-1.97, 1.98-2.18, 2.18-2.30, 2.38-2.59, 2.82-3.00, 3.62-3.81, 3.83-4.14, 4.46-4.64, 4.88-5.09, 5.56-5.78, 6.77-6.84, 6.84-6.94, 7.05-7.21.

Example 16 (19)

2-Propanyl 4-{(3S,5aR,6R,7R,8aS)-6-[(1E,3R)-4-(2-chlorophenoxy)-3-hydroxy-1-buten-1-yl]-7-hydroxyoctahydro-2H-cyclopenta[b]oxepin-3-yl}butanoate TLC: Rf 0.48 (ethyl acetate);
$^1$H-NMR (300 MHz, CDCl$_3$): δ 0.87-1.18, 1.22, 1.35-1.95, 1.99-2.18, 2.23, 2.40-2.54, 2.62-2.74, 2.91, 3.65-3.80, 3.88-3.99, 3.99-4.11, 4.49-4.65, 4.89-5.08, 5.57-5.76, 6.86-6.98, 7.15-7.24, 7.30-7.40.

Example 16 (20)

2-Propanyl 6-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}hexanoate TLC: Rf 0.59 (ethyl acetate);
$^1$H-NMR (300 MHz, CDCl$_3$): δ 0.88-1.17, 1.18-1.37, 1.40-1.94, 1.98-2.19, 2.20-2.30, 2.36-2.56, 2.89, 3.66-4.10, 4.46-4.59, 4.91-5.07, 5.57-5.75, 6.87-7.01, 7.24-7.33.

Example 16 (21)

2-Propanyl 4-{(3S,5aR,6R,7R,8aS)-6-[(1E,3R)-4-(3,5-dichlorophenoxy)-3-hydroxy-1-buten-1-yl]-7-hydroxyoctahydro-2H-cyclopenta[b]oxepin-3-yl}butanoate TLC: Rf 0.57 (ethyl acetate);
$^1$H-NMR (300 MHz, CDCl$_3$): δ 0.87-1.19, 1.17-1.25, 1.33-1.83, 1.82-1.98, 2.00-2.19, 2.23, 2.38-2.59, 2.82-2.97, 3.63-3.79, 3.80-4.16, 4.40-4.61, 4.88-5.10, 5.52-5.75, 6.81, 6.97.

Example 16 (22)

2-Propanyl 4-[(3S,5aR,6R,7R,8aS)-6-[(1E,3R)-4-(3-chloro-5-fluorophenoxy)-3-hydroxy-1-buten-1-yl]-7-hydroxyoctahydro-2H-cyclopenta[b]oxepin-3-yl]butanoate TLC: Rf 0.56 (ethyl acetate);
$^1$H-NMR (300 MHz, CDCl$_3$): δ 0.87-1.17, 1.81-1.25, 1.34-1.83, 1.83-1.97, 2.04-2.18, 2.23, 2.40-2.55, 2.84-2.97, 3.64-3.79, 3.82-3.90, 3.91-3.99, 3.99-4.13, 4.41-4.59, 4.90-5.09, 5.53-5.74, 6.48-6.59, 6.65-6.79.

Example 16 (23)

2-Propanyl 4-{(3S,5aR,6R,7R,8aS)-6-[(1E,3R)-4-(2,3-difluorophenoxy)-3-hydroxy-1-buten-1-yl]-7-hydroxyoctahydro-2H-cyclopenta[b]oxepin-3-yl}butanoate TLC: Rf 0.51 (ethyl acetate);
$^1$H-NMR (300 MHz, CDCl$_3$): δ 0.88-1.18, 1.18-1.26, 1.34-1.81, 1.82-1.99, 2.04-2.16, 2.18-2.28, 2.37-2.56, 2.73, 2.91, 3.63-3.80, 3.87-4.15, 4.46-4.65, 4.86-5.07, 5.53-5.77, 6.67-6.85, 6.89-7.07.

Example 16 (24)

2-Propanyl 4-{(3S,5aR,6R,7R,8aS)-6-[(1E,3R)-4-(3,5-difluorophenoxy)-3-hydroxy-1-buten-1-yl]-7-hydroxyoctahydro-2H-cyclopenta[b]oxepin-3-yl}butanoate TLC: Rf 0.54 (ethyl acetate);
$^1$H-NMR (300 MHz, CDCl$_3$): δ 0.87-1.18, 1.18-1.25, 1.36-1.84, 1.82-1.97, 2.03-2.19, 2.23, 2.40-2.58, 2.83-2.99, 3.65-3.80, 3.81-3.90, 3.90-4.12, 4.41-4.59, 4.87-5.11, 5.52-5.79, 6.32-6.54.

Example 16 (25)

2-Propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate

[Chemical formula 35]

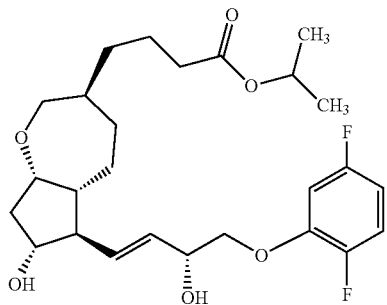

TLC: Rf 0.54 (ethyl acetate);
$^1$H-NMR (300 MHz, CDCl$_3$): δ 0.92-1.18, 1.21, 1.34-1.82, 1.82-1.96, 2.03-2.18, 2.23, 2.28, 2.41-2.54, 2.78, 2.84-2.98, 3.62-3.80, 3.86-4.11, 4.47-4.61, 4.89-5.07, 5.54-5.76, 6.54-6.66, 6.66-6.76, 6.93-7.05.

Example 16 (26)

2-Propanyl 4-{(3S,5aR,6R,7R,8aS)-6-[(1E,3R)-4-(5-chloro-2-fluorophenoxy)-3-hydroxy-1-buten-1-yl]-7-hydroxyoctahydro-2H-cyclopenta[b]oxepin-3-yl}butanoate TLC: Rf 0.69 (ethyl acetate);
$^1$H-NMR (300 MHz, CDCl$_3$): δ 0.90-1.19, 1.22, 1.37-1.96, 2.03-2.29, 2.41-2.54, 2.68, 2.91, 3.65-3.80, 3.86-4.11, 4.48-4.60, 4.91-5.08, 5.55-5.75, 6.86-6.94, 6.94-7.06.

Example 16 (27)

2-Propanyl 4-{(3S,5aR,6R,7R,8aS)-6-[(1E,3R)-4-(3-chloro-4-fluorophenoxy)-3-hydroxy-1-buten-1-yl]-7-hydroxyoctahydro-2H-cyclopenta[b]oxepin-3-yl}butanoate TLC: Rf 0.58 (ethyl acetate);
$^1$H-NMR (300 MHz, CDCl$_3$): δ 0.91-1.19, 1.21, 1.37-1.97, 2.02-2.19, 2.23, 2.41-2.54, 2.91, 3.66-3.80, 3.80-3.89, 3.89-4.10, 4.45-4.56, 4.99, 5.55-5.75, 6.73-6.81, 6.95, 7.00-7.10.

Example 16 (28)

2-Propanyl 4-{(3S,5aR,6R,7R,8aS)-6-[(1E,3R)-3-hydroxy-4-phenoxy-1-buten-1-yl]-7-methoxyoctahydro-2H-cyclopenta[b]oxepin-3-yl}butanoate TLC: Rf 0.72 (hexane:ethyl acetate=1:1);
$^1$H-NMR (300 MHz, CDCl$_3$): δ 0.88-1.19, 1.22, 1.36-1.81, 1.81-1.97, 2.15-2.29, 2.42, 2.46-2.59, 2.91, 3.25-3.47, 3.81-4.09, 4.46-4.59, 4.89-5.10, 5.56-5.67, 5.69-5.82, 6.87-7.02, 7.23-7.35.

Example 16 (29)

2-Propanyl 4-{(3S,5aR,6R,7R,8aS)-6-[(1E,3R)-4-(3-chloro-2-fluorophenoxy)-3-hydroxy-1-buten-1-yl]-7-hydroxyoctahydro-2H-cyclopenta[b]oxepin-3-yl}butanoate TLC: Rf 0.37 (ethyl acetate);
$^1$H-NMR (300 MHz, CDCl$_3$): δ 0.84-1.18, 1.19-1.27, 1.34-1.97, 2.02-2.19, 2.23, 2.39-2.54, 2.66, 2.81-2.99, 3.61-3.82, 3.86-4.12, 4.45-4.63, 4.88-5.09, 5.55-5.76, 6.82-6.91, 6.93-7.07.

Example 16 (30)

2-Propanyl {(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}acetate TLC: Rf 0.43 (ethyl acetate);
$^1$H-NMR (300 MHz, CDCl$_3$): δ 1.02-1.19, 1.22, 1.42-1.59, 1.63-1.96, 2.02-2.28, 2.41-2.55, 2.60, 2.92-3.04, 3.65-3.79, 3.82-3.92, 3.92-4.12, 4.44-4.58, 4.89-5.08, 5.55-5.75, 6.80, 6.91, 6.95, 7.19.

Example 16 (31)

2-Propanyl 4-{(3S,5aR,6R,7R,8aS)-6-[(1E,3R)-4-(2,4-difluorophenoxy)-3-hydroxy-1-buten-1-yl]-7-hydroxyoctahydro-2H-cyclopenta[b]oxepin-3-yl}butanoate TLC: Rf 0.63 (ethyl acetate);
$^1$H-NMR (300 MHz, CDCl$_3$): δ 0.89-1.18, 1.18-1.25, 1.35-1.82, 1.82-1.94, 2.03-2.16, 2.23, 2.40-2.56, 2.84-2.95, 2.97, 3.70, 3.85-4.08, 4.46-4.55, 4.92-5.06, 5.55-5.71, 6.73-6.98.

Example 16 (32)

2-Propanyl 4-{(3S,5aR,6R,7R,8aS)-6-[(1E,3R)-4-(3,4-difluorophenoxy)-3-hydroxy-1-buten-1-yl]-7-hydroxyoctahydro-2H-cyclopenta[b]oxepin-3-yl}butanoate TLC: Rf 0.62 (ethyl acetate);
¹H-NMR (300 MHz, CDCl₃): δ 0.91-1.18, 1.22, 1.36-1.83, 1.83-1.96, 2.05-2.18, 2.23, 2.48, 2.53-2.59, 2.85-2.96, 3.65-3.78, 3.79-3.87, 3.89-4.09, 4.44-4.55, 4.91-5.07, 5.56-5.73, 6.57-6.64, 6.73, 6.99-7.12.

Example 16 (33)

2-Propanyl 4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate TLC: Rf 0.28 (dichloromethane:methanol=20:1);
¹H-NMR (300 MHz, CDCl₃): δ 1.22, 1.34-1.98, 2.07-2.19, 2.21-2.33, 2.40, 2.77, 3.02, 3.40, 3.65-3.77, 3.78-4.03, 4.44-4.56, 4.92-5.08, 5.57-5.71, 6.87-7.01, 7.24-7.34.

Example 16 (34)

Ethyl 4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate TLC: Rf 0.25 (dichloromethane:methanol=20:1);
¹H-NMR (300 MHz, CDCl₃): δ 1.25, 1.35-1.88, 2.08-2.23, 2.22-2.49, 2.67, 3.41, 3.64-4.06, 4.12, 4.46-4.59, 5.58-5.78, 6.85-7.06, 7.22-7.37.

Example 16 (35)

Ethyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate

[Chemical formula 36]

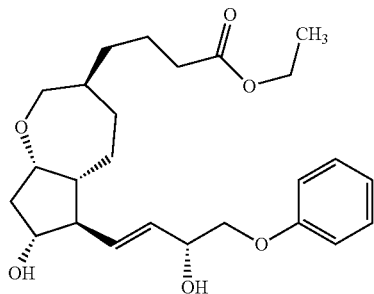

TLC: Rf 0.23 (dichloromethane:methanol=20:1);
¹H-NMR (300 MHz, CDCl₃): δ 0.89-1.20, 1.25, 1.35-1.99, 2.03-2.19, 2.26, 2.41-2.54, 2.58, 2.91, 3.65-3.81, 3.83-4.08, 4.12, 4.46-4.61, 5.58-5.75, 6.84-7.05, 7.22-7.37.

Example 16 (36)

2-Propanyl 4-{(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoate TLC: Rf 0.47 (ethyl acetate);
¹H-NMR (300 MHz, CDCl₃): δ 1.23, 1.34-1.89, 2.07-2.22, 2.27, 2.34-2.46, 2.47-2.67, 3.41, 3.67-4.06, 4.43-4.60, 4.91-5.10, 5.54-5.77, 6.78-6.84, 6.92, 6.93-6.99, 7.20.

Example 16 (37)

2-Propanyl 4-{(3R,5aR,6R,7R,8aS)-6-[(1E,3S)-4-(3-chlorophenoxy)-3-hydroxy-1-buten-1-yl]-7-hydroxyoctahydro-2H-cyclopenta[b]oxepin-3-yl}butanoate TLC: Rf 0.47 (ethyl acetate);
¹H-NMR (300 MHz, CDCl₃): δ 1.23, 1.33-1.87, 1.86-1.96, 2.10-2.23, 2.23-2.50, 3.42, 3.68-3.90, 3.93-4.07, 4.44-4.63, 4.91-5.10, 5.56-5.79, 6.77-6.85, 6.92, 6.93-7.00, 7.20.

Example 16 (38)

2-Propanyl 4-{(3S,5aR,6R,7R,8aS)-6-[(1E,3S)-4-(3-chlorophenoxy)-3-hydroxy-1-buten-1-yl]-7-hydroxyoctahydro-2H-cyclopenta[b]oxepin-3-yl}butanoate TLC: Rf 0.65 (ethyl acetate);
¹H-NMR (300 MHz, CDCl₃): δ 0.66-2.01, 2.04-2.18, 2.23, 2.29-2.57, 2.91, 3.73, 3.85, 3.90-4.13, 4.45-4.59, 4.90-5.07, 5.53-5.78, 6.75-6.84, 6.91, 6.92-6.98, 7.19.

Example 16 (39)

2-Propanyl 4-{(3S,5aR,6R,7R,8aS)-6-[(1E,3S)-4-(2,5-difluorophenoxy)-3-hydroxy-1-buten-1-yl]-7-hydroxyoctahydro-2H-cyclopenta[b]oxepin-3-yl}butanoate TLC: Rf 0.39 (isopropyl alcohol:hexane=1:5);
¹H-NMR (300 MHz, CDCl₃): δ 0.91-1.18, 1.18-1.26, 1.36-1.83, 1.83-1.97, 2.05-2.19, 2.23, 2.39-2.56, 2.91, 3.63-3.81, 3.82-4.11, 4.48-4.64, 4.88-5.08, 5.54-5.77, 6.53-6.65, 6.66-6.79, 6.93-7.09.

Example 16 (40)

2-Propanyl {(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}acetate TLC: Rf 0.59 (ethyl acetate);
¹H-NMR (300 MHz, CDCl₃): δ 1.02-1.18, 1.19-1.26, 2.10-2.39, 2.50, 2.76-2.89, 3.00, 3.67-3.80, 3.88-4.13, 4.50-4.61, 5.00, 5.58-5.75, 6.62, 6.72, 7.03.

Example 16 (41)

2-Propanyl 4-{(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate TLC: Rf 0.55 (ethyl acetate);
¹H-NMR (300 MHz, CDCl₃): δ 1.15-1.34, 1.35-1.87, 2.11-2.25, 2.29, 2.42, 2.69, 3.43, 3.70-4.09, 4.51-4.62, 4.95-5.09, 5.58-5.76, 6.62, 6.73, 7.03.

Example 16 (42)

2-Propanyl 4-{(3S,5aR,6R,7R,8aS)-6-[(1E,3R)-4-(cyclohexyloxy)-3-hydroxy-1-buten-1-yl]-7-hydroxyoctahydro-2H-cyclopenta[b]oxepin-3-yl}butanoate TLC: Rf 0.33 (ethyl acetate);
¹H-NMR (300 MHz, CDCl₃): δ 0.91-1.35, 1.42-1.76, 1.85-1.93, 2.04-2.12, 2.22-2.27, 2.42-2.51, 2.67, 2.87-2.95, 3.26-

3.32, 3.50-3.55, 3.66-3.75, 3.93-4.07, 4.24-4.29, 4.96-5.05, 5.50-5.64.

Example 17 (1)

4-{(3S,5aR,6R,7R,8aS)-6-[(1E,3R)-4-(2,3-difluorophenoxy)-3-hydroxy-1-buten-1-yl]-7-hydroxyoctahydro-2H-cyclopenta[b]oxepin-3-yl}butanoic acid

[Chemical formula 37]

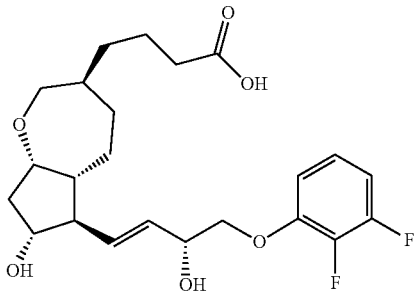

An aqueous sodium hydroxide solution (500 μL) was added to a methanol solution (1.5 mL) of the compound (49 mg, 0.102 mmol) produced in Example 16 (23), and the mixture was stirred at 40° C. for 2 hours. An ice was placed into the reaction solution, and 1N hydrochloric acid (1.2 mL) was added. This was extracted with ethyl acetate two times, and the collected organic layers were washed with a saturated saline, and dried with anhydrous sodium sulfate. The solution was concentrated under reduced pressure, and purified with a silica gel column (BW-235, dichloromethane:methanol=10:1) to obtain a titled compound (45 mg) having the following physical property values.

TLC: Rf 0.56 (ethyl acetate:methanol=8:1);
$^1$H-NMR (300 MHz, CD$_3$OD): δ 0.78-1.24, 1.24-2.08, 2.25, 2.36-2.49, 2.91-3.02, 3.59-3.73, 3.86-4.07, 4.38-4.49, 5.54-5.71, 6.75-6.86, 6.86-6.94, 6.98-7.10.

Example 17 (2) to Example 17 (33)

Compounds produced in Example 16 (1) to Example 16 (22) and Example 16 (24) to Example 16 (33) were subjected to the same objective operations as those of Example 17 (1) to obtain the following Example compounds.

Example 17 (2)

4-{(3S,5aR,6R,7R,8aS)-7-hydroxy-6-[(1E,3S)-3-hydroxy-5-phenyl-1-penten-1-yl]octahydro-2H-cyclopenta[b]oxepin-3-yl}butanoic acid TLC: Rf 0.38 (dichloromethane:methanol=9:1);
$^1$H-NMR (300 MHz, CDCl$_3$): δ 0.87-1.23, 1.32-1.97, 2.00-2.13, 2.32, 2.40-2.54, 2.57-2.78, 2.91, 3.61-3.75, 3.85-4.20, 5.36-5.48, 5.52-5.66, 7.11-7.33.

Example 17 (3)

4-{(3S,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoic acid

[Chemical formula 38]

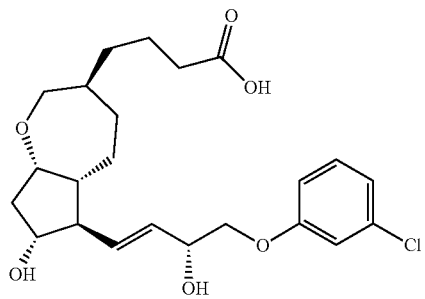

TLC: Rf 0.43 (dichloromethane:methanol=9:1);
$^1$H-NMR (300 MHz, CDCl$_3$): δ 0.83-1.27, 1.35-1.97, 2.02-2.20, 2.33, 2.41-2.55, 2.84-2.99, 3.67-3.78, 3.80-4.11, 4.45-4.58, 5.54-5.74, 6.76-6.84, 6.91-6.98, 7.20.

Example 17 (4)

4-{(3S,5aR,6R,7R,8aS)-7-hydroxy-6-[(1E,3R)-3-hydroxy-4-(3-methylphenoxy)-1-buten-1-yl]octahydro-2H-cyclopenta[b]oxepin-3-yl}butanoic acid TLC: Rf 0.46 (dichloromethane:methanol=6:1);
$^1$H-NMR (300 MHz, CDCl$_3$): δ 0.80-1.21, 1.35-1.97, 2.00-2.19, 2.24-2.38, 2.40-2.55, 2.91, 3.65-3.78, 3.82-3.90, 3.90-4.08, 4.45-4.57, 5.54-5.73, 6.65-6.75, 6.78, 7.16.

Example 17 (5)

4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoic acid TLC: Rf 0.36 (chloroform:methanol=9:1);
$^1$H-NMR (300 MHz, CD$_3$OD): δ 1.46-2.17, 2.40-2.56, 2.87-3.03, 3.33-3.45, 3.63-3.77, 3.83-4.23, 4.35-4.49, 5.58-5.76, 6.82-6.99, 7.16-7.37, 7.92.

Example 17 (6)

4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoic acid TLC: Rf 0.34 (chloroform:methanol=9:1);
$^1$H-NMR (300 MHz, CDCl$_3$): δ 1.47-1.96, 1.95-2.12, 2.16-2.36, 2.44-2.61, 2.97-3.15, 3.67-4.18, 4.28, 4.45-4.61, 5.56-5.75, 6.85-7.02, 7.22-7.34, 7.46-7.54, 7.99-8.07.

Example 17 (7)

3-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoic acid TLC: Rf 0.45 (chloroform:methanol:acetic acid=10:1:0.1);
$^1$H-NMR (300 MHz, CD$_3$OD): δ 1.49-2.20, 2.41-2.56, 2.86-3.03, 3.32-3.44, 3.63-3.78, 3.85-4.22, 4.37-4.49, 5.58-5.75, 6.84-6.98, 7.17-7.30, 7.33-7.48, 7.79-7.89.

Example 17 (8)

3-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoic acid TLC: Rf 0.45 (chloroform:methanol:acetic acid=10:1:0.1);
$^1$H-NMR (300 MHz, CDCl$_3$): δ 1.48-1.72, 1.73-1.94, 1.95-2.13, 2.21-2.37, 2.43-2.59, 3.00-3.15, 3.66-4.00, 4.03-4.14, 4.25, 4.44-4.56, 5.56-5.74, 6.82-6.99, 7.19-7.30, 7.39, 7.65, 7.94, 8.11

Example 17 (9)

4-{(3S,5aR,6R,7R,8aS)-6-[(1E,3R)-4-(4-chlorophenoxy)-3-hydroxy-1-buten-1-yl]-7-hydroxyoctahydro-2H-cyclopenta[b]oxepin-3-yl}butanoic acid TLC: Rf 0.40 (chloroform:methanol:acetic acid=10:1:0.1);
$^1$H-NMR (300 MHz, CD$_3$OD): δ 0.93-1.26, 1.26-1.82, 1.82-2.07, 2.25, 2.36-2.50, 2.90-3.03, 3.59-3.71, 3.83-4.05, 4.35-4.45, 5.55-5.70, 6.87-6.95, 7.19-7.28.

Example 17 (10)

4-{(3S,5aR,6R,7R,8aS)-7-hydroxy-6-[(1E,3R)-3-hydroxy-4-(4-methylphenoxy)-1-buten-1-yl]octahydro-2H-cyclopenta[b]oxepin-3-yl}butanoic acid TLC: Rf 0.40 (chloroform:methanol:acetic acid=10:1:0.1);
$^1$H-NMR (300 MHz, CD$_3$OD): δ 0.90-2.08, 2.18-2.33, 2.34-2.51, 2.97, 3.58-3.73, 3.79-4.07, 4.31-4.47, 5.54-5.71, 6.73-6.86, 7.04.

Example 17 (11)

4-[(3S,5aR,6R,7R,8aS)-7-hydroxy-6-{(1E,3R)-3-hydroxy-4-[4-(trifluoromethyl)phenoxy]-1-buten-1-yl}octahydro-2H-cyclopenta[b]oxepin-3-yl]butanoic acid TLC: Rf 0.40 (chloroform:methanol:acetic acid=10:1:0.1);
$^1$H-NMR (300 MHz, CD$_3$OD): δ 0.92-1.94, 1.94-2.08, 2.25, 2.36-2.50, 2.91-3.03, 3.59-3.73, 3.91-4.07, 4.40-4.49, 5.57-5.72, 7.01-7.13, 7.49-7.61.

Example 17 (12)

4-{(3S,5aR,6R,7R,8aS)-6-[(1E,3R)-4-(2-fluorophenoxy)-3-hydroxy-1-buten-1-yl]-7-hydroxyoctahydro-2H-cyclopenta[b]oxepin-3-yl}butanoic acid TLC: Rf 0.39 (dichloromethane:methanol=10:1);
$^1$H-NMR (300 MHz, CD$_3$OD): δ 0.78-2.10, 2.25, 2.35-2.49, 2.89-3.02, 3.58-3.74, 3.90-4.06, 4.34-4.51, 5.53-5.72, 6.83-6.96, 7.01-7.15.

Example 17 (13)

4-{(3S,5aR,6R,7R,8aS)-6-[(1E,3R)-4-(3-fluorophenoxy)-3-hydroxy-1-buten-1-yl]-7-hydroxyoctahydro-2H-cyclopenta[b]oxepin-3-yl}butanoic acid TLC: Rf 0.37 (dichloromethane:methanol=10:1);
$^1$H-NMR (300 MHz, CDCl$_3$): δ 0.80-1.22, 1.34-1.97, 2.05-2.18, 2.32, 2.40-5.56, 2.84-2.98, 3.66-3.78, 3.80-4.10, 4.46-4.57, 5.55-5.74, 6.55-6.75, 7.14-7.28.

Example 17 (14)

4-{(3S,5aR,6R,7R,8aS)-6-[(1E,3R)-4-(4-fluorophenoxy)-3-hydroxy-1-buten-1-yl]-7-hydroxyoctahydro-2H-cyclopenta[b]oxepin-3-yl}butanoic acid TLC: Rf 0.40 (dichloromethane:methanol=10:1);
$^1$H-NMR (300 MHz, CDCl$_3$): δ 0.83-1.21, 1.34-1.98, 2.05-2.18, 2.32, 2.39-2.57, 2.85-3.00, 3.66-3.79, 3.79-3.88, 3.89-4.09, 4.41-4.60, 5.54-5.76, 6.79-6.91, 6.90-7.03.

Example 17 (15)

4-[(3S,5aR,6R,7R,8aS)-7-hydroxy-6-{(1E,3R)-3-hydroxy-4-[3-(trifluoromethyl)phenoxy]-1-buten-1-yl}octahydro-2H-cyclopenta[b]oxepin-3-yl]butanoic acid TLC: Rf 0.37 (chloroform:methanol:acetic acid=10:1:0.1);
$^1$H-NMR (300 MHz, CD$_3$OD): δ 0.92-2.09, 2.25, 2.37-2.50, 2.88-3.04, 3.57-3.74, 3.89-4.07, 4.37-4.49, 5.54-5.74, 7.13-7.27, 7.38-7.51.

Example 17 (16)

4-{(3S,5aR,6R,7R,8aS)-7-hydroxy-6-[(1E,3R)-3-hydroxy-4-(3-methoxyphenoxy)-1-buten-1-yl]octahydro-2H-cyclopenta[b]oxepin-3-yl}butanoic acid TLC: Rf 0.37 (chloroform:methanol:acetic acid=10:1:0.1);
$^1$H-NMR (300 MHz, CD$_3$OD): δ 0.91-1.21, 1.27-1.83, 1.82-2.08, 2.25, 2.36-2.50, 2.90-3.03, 3.59-3.72, 3.75, 3.80-4.05, 4.34-4.45, 5.55-5.70, 6.44-6.55, 7.08-7.18.

Example 17 (17)

4-{(3S,5aR,6R,7R,8aS)-7-hydroxy-6-[(1E,3R)-3-hydroxy-4-(4-methoxyphenoxy)-1-buten-1-yl]octahydro-2H-cyclopenta[b]oxepin-3-yl}butanoic acid TLC: Rf 0.39 (chloroform:methanol:acetic acid=10:1:0.1);
$^1$H-NMR (300 MHz, CD$_3$OD): δ 0.93-1.24, 1.30-1.47, 1.47-1.82, 1.82-2.09, 2.25, 2.36-2.50, 2.90-3.03, 3.59-3.71, 3.73, 3.78-3.92, 3.93-4.05, 4.32-4.42, 5.54-5.70, 6.74-6.92.

Example 17 (18)

4-{(3S,5aR,6R,7R,8aS)-7-hydroxy-6-[(1E,3R)-3-hydroxy-4-(2-methylphenoxy)-1-buten-1-yl]octahydro-2H-cyclopenta[b]oxepin-3-yl}butanoic acid TLC: Rf 0.61 (ethyl acetate:methanol=8:1);
$^1$H-NMR (300 MHz, CD$_3$OD): δ 0.87-1.23, 1.24-1.93, 1.94-2.09, 2.15-2.32, 2.35-2.50, 2.89-3.03, 3.58-3.72, 3.85-4.07, 4.37-4.47, 5.56-5.71, 6.74-6.88, 7.03-7.15.

Example 17 (19)

4-{(3S,5aR,6R,7R,8aS)-6-[(1E,3R)-4-(2-chlorophenoxy)-3-hydroxy-1-buten-1-yl]-7-hydroxyoctahydro-2H-cyclopenta[b]oxepin-3-yl}butanoic acid TLC: Rf 0.50 (ethyl acetate:methanol=8:1);
$^1$H-NMR (300 MHz, CD$_3$OD): δ 0.84-1.21, 1.22-1.93, 1.93-2.10, 2.25, 2.35-2.49, 2.96, 3.57-3.72, 3.89-4.06, 4.39-4.49, 5.57-5.71, 6.90, 7.05, 7.19-7.27, 7.33.

Example 17 (20)

6-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}hexanoic acid TLC: Rf 0.24 (chloroform:methanol:acetic acid=10:1:0.1);
¹H-NMR (300 MHz, CD₃OD): δ 0.90-1.20, 1.22-1.47, 1.46-1.67, 1.66-1.93, 1.93-2.08, 2.21-2.32, 2.36-2.49, 2.95, 3.59-3.72, 3.83-4.07, 4.35-4.47, 5.55-5.71, 6.86-6.95, 7.19-7.30.

Example 17 (21)

4-{(3S,5aR,6R,7R,8aS)-6-[(1E,3R)-4-(3,5-dichlorophenoxy)-3-hydroxy-1-buten-1-yl]-7-hydroxyoctahydro-2H-cyclopenta[b]oxepin-3-yl}butanoic acid TLC: Rf 0.62 (ethyl acetate:methanol=8:1);
¹H-NMR (300 MHz, CD₃OD): δ 0.90-1.22, 1.25-2.09, 2.25, 2.35-2.51, 2.97, 3.58-3.72, 3.83-4.08, 4.31-4.48, 5.50-5.73, 6.93, 6.98.

Example 17 (22)

4-{(3S,5aR,6R,7R,8aS)-6-[(1E,3R)-4-(3-chloro-5-fluorophenoxy)-3-hydroxy-1-buten-1-yl]-7-hydroxy-octahydro-2H-cyclopenta[b]oxepin-3-yl}butanoic acid TLC: Rf 0.62 (ethyl acetate:methanol=8:1);
¹H-NMR (300 MHz, CD₃OD): δ 0.90-1.22, 1.27-2.10, 2.26, 2.37-2.51, 2.97, 3.58-3.73, 3.85-4.06, 4.35-4.47, 5.54-5.72, 6.69, 6.75, 6.79-6.85.

Example 17 (23)

4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoic acid

[Chemical formula 39]

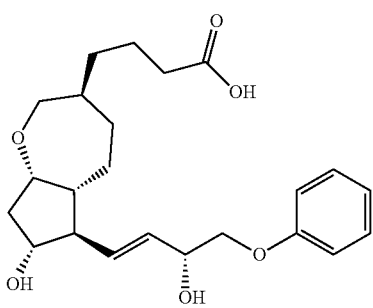

TLC: Rf 0.33 (chloroform:methanol=10:1);
¹H-NMR (300 MHz, CDCl₃): δ 0.90-1.30, 1.37-1.81, 1.82-1.96, 2.04-2.19, 2.32, 2.41-2.54, 2.85-2.98, 3.65-3.79, 3.84-4.10, 4.47-4.58, 5.57-5.74, 6.86-7.03, 7.23-7.35.

Example 17 (24)

4-{(3S,5aR,6R,7R,8aS)-6-[(1E,3R)-4-(3,5-difluorophenoxy)-3-hydroxy-1-buten-1-yl]-7-hydroxyoctahydro-2H-cyclopenta[b]oxepin-3-yl}butanoic acid TLC: Rf 0.59 (ethyl acetate:methanol=8:1);
¹H-NMR (300 MHz, CD₃OD): δ 0.91-1.24, 1.24-2.11, 2.25, 2.35-2.51, 2.97, 3.57-3.75, 3.80-4.11, 4.29-4.50, 5.50-5.77, 6.38-6.68.

Example 17 (25)

4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoic acid

[Chemical formula 40]

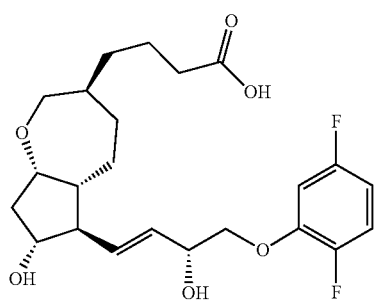

TLC: Rf 0.60 (ethyl acetate:methanol=8:1);
¹H-NMR (300 MHz, CD₃OD): δ 0.89-1.23, 1.25-1.94, 1.95-2.10, 2.25, 2.35-2.51, 2.92-3.03, 3.58-3.73, 3.87-4.09, 4.35-4.50, 5.55-5.75, 6.58-6.71, 6.84-6.97, 6.99-7.14.

Example 17 (26)

4-{(3S,5aR,6R,7R,8aS)-6-[(1E,3R)-4-(5-chloro-2-fluorophenoxy)-3-hydroxy-1-buten-1-yl]-7-hydroxy-octahydro-2H-cyclopenta[b]oxepin-3-yl}butanoic acid TLC: Rf 0.59 (chloroform:methanol:acetic acid=10:1:0.1);
¹H-NMR (300 MHz, CD₃OD): δ 0.92-1.20, 1.29-1.46, 1.46-2.08, 2.25, 2.36-2.49, 2.91-3.02, 3.59-3.71, 3.92-4.05, 4.38-4.47, 5.55-5.71, 6.88-6.94, 7.07, 7.13.

Example 17 (27)

4-{(3S,5aR,6R,7R,8aS)-6-[(1E,3R)-4-(3-chloro-4-fluorophenoxy)-3-hydroxy-1-buten-1-yl]-7-hydroxy-octahydro-2H-cyclopenta[b]oxepin-3-yl}butanoic acid TLC: Rf 0.58 (chloroform:methanol:acetic acid=10:1:0.1);
¹H-NMR (300 MHz, CD₃OD): δ 0.92-1.22, 1.30-1.47, 1.47-1.83, 1.82-2.07, 2.25, 2.36-2.49, 2.90-3.03, 3.59-3.72, 3.82-4.05, 4.35-4.44, 5.54-5.70, 6.84-6.92, 7.04, 7.13.

Example 17 (28)

4-{(3S,5aR,6R,7R,8aS)-6-[(1E,3R)-3-hydroxy-4-phenoxy-1-buten-1-yl]-7-methoxyoctahydro-2H-cyclopenta[b]oxepin-3-yl}butanoic acid TLC: Rf 0.43 (chloroform:methanol:water=10:1:0.1);
$^1$H-NMR (300 MHz, CDCl$_3$): δ 0.89-1.22, 1.35-1.81, 1.81-1.97, 2.15-2.28, 2.32, 2.46-2.59, 2.92, 3.26-3.46, 3.82-4.09, 4.48-4.58, 5.55-5.67, 5.69-5.82, 6.87-7.02, 7.24-7.34.

Example 17 (29)

4-{(3S,5aR,6R,7R,8aS)-6-[(1E,3R)-4-(3-chloro-2-fluorophenoxy)-3-hydroxy-1-buten-1-yl]-7-hydroxyoctahydro-2H-cyclopenta[b]oxepin-3-yl}butanoic acid TLC: Rf 0.26 (dichloromethane:methanol=5:1);
$^1$H-NMR (300 MHz, CD$_3$OD): δ 0.89-1.23, 1.25-2.06, 2.25, 2.31-2.51, 2.87-3.03, 3.57-3.75, 3.87-4.09, 4.35-4.50, 5.52-5.73, 6.89-7.15.

Example 17 (30)

{(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}acetic acid TLC: Rf 0.26 (chloroform:methanol:acetic acid=10:1:0.1);
$^1$H-NMR (300 MHz, CD$_3$OD): δ 1.04-1.20, 1.35-1.63, 1.65-2.19, 2.37-2.50, 2.97-3.09, 3.25-3.38, 3.59-3.72, 3.85-4.07, 4.35-4.46, 5.55-5.70, 6.86, 6.89-6.97, 7.22.

Example 17 (31)

4-{(3S,5aR,6R,7R,8aS)-6-[(1E,3R)-4-(2,4-difluorophenoxy)-3-hydroxy-1-buten-1-yl]-7-hydroxyoctahydro-2H-cyclopenta[b]oxepin-3-yl}butanoic acid TLC: Rf 0.22 (chloroform:methanol:water=10:1:0.1);
$^1$H-NMR (300 MHz, CD$_3$OD): δ 0.87-1.26, 1.26-1.82, 1.81-1.94, 1.94-2.07, 2.25, 2.43, 2.97, 3.65, 3.91-4.06, 4.36-4.47, 5.54-5.71, 6.79-6.89, 6.95, 7.09.

Example 17 (32)

4-{(3S,5aR,6R,7R,8aS)-6-[(1E,3R)-4-(3,4-difluorophenoxy)-3-hydroxy-1-buten-1-yl]-7-hydroxyoctahydro-2H-cyclopenta[b]oxepin-3-yl}butanoic acid TLC: Rf 0.22 (chloroform:methanol:water=10:1:0.1);
$^1$H-NMR (300 MHz, CD$_3$OD): δ 0.93-1.24, 1.27-1.83, 1.82-1.94, 1.94-2.07, 2.25, 2.43, 2.97, 3.65, 3.81-4.06, 4.35-4.44, 5.54-5.71, 6.67-6.76, 6.86, 7.13.

Example 17 (33)

4-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoic acid (low polar body)

TLC: Rf 0.40 (chloroform:methanol=10:1);
$^1$H-NMR (300 MHz, CDCl$_3$): δ 1.12-1.91, 2.07-2.91, 3.34-3.50, 3.65-4.06, 4.46-4.58, 5.56-5.73, 6.84-7.05, 7.22-7.35.

Example 17 (34)

4-{(3S,5aR,6R,7R,8aS)-7-hydroxy-6-[(1E,3S)-3-hydroxy-1-octen-1-yl]octahydro-2H-cyclopenta[b]oxepin-3-yl}butanoic acid Using (3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one, using 4-ethoxy-4-oxobutylzinc bromide, and using a corresponding phosphonic acid salt in place of dimethyl-(3-phenoxy-2-oxopropyl)-phosphonate, the substances were subjected to the same objective operations as those of Example 1→Example 2→Example 3→Example 4→Example 5→Example 6→Example 7→Example 8→Example 9→Example 10→Example 11→Example 12→Example 13→Example 14→Example 15→Example 16 (1)→Example 17 (1) to obtain a titled compound having the following physical property values.

TLC: Rf 0.53 (ethyl acetate:methanol=8:1);
$^1$H-NMR (300 MHz, CD$_3$OD): δ 0.77-1.21, 1.22-1.82, 1.82-2.05, 2.25, 2.35-2.48, 2.91-3.02, 3.56-3.69, 3.88-4.07, 5.34-5.56.

Example 17 (35) to Example 17 (41)

Using the compounds produced in Example 16 (36) to Example 16 (42), these compounds were subjected to the same objective operations as those of Example 17 (1) to obtain the following Example compounds.

Example 17 (35)

4-{(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoic acid TLC: Rf 0.64 (dichloromethane:methanol=5:1);
$^1$H-NMR (300 MHz, CD$_3$OD): δ 1.36-1.86, 1.97-2.12, 2.29, 2.33-2.45, 3.45, 3.61-3.73, 3.77-3.85, 3.85-4.05, 4.34-4.47, 5.55-5.71, 6.83-6.89, 6.89-6.94, 6.94-6.97, 7.22.

Example 17 (36)

4-{(3R,5aR,6R,7R,8aS)-6-[(1E,3S)-4-(3-chlorophenoxy)-3-hydroxy-1-buten-1-yl]-7-hydroxyoctahydro-2H-cyclopenta[b]oxepin-3-yl}butanoic acid TLC: Rf 0.63 (dichloromethane:methanol=5:1);
$^1$H-NMR (300 MHz, CDCl$_3$): δ 1.37-1.88, 1.94-2.13, 2.29, 2.33-2.46, 3.45, 3.60-3.74, 3.76-3.93, 3.94-4.06, 4.36-4.47, 5.57-5.72, 6.84-6.89, 6.89-6.94, 6.96, 7.22.

Example 17 (37)

4-{(3S,5aR,6R,7R,8aS)-6-[(1E,3S)-4-(3-chlorophenoxy)-3-hydroxy-1-buten-1-yl]-7-hydroxyoctahydro-2H-cyclopenta[b]oxepin-3-yl}butanoic acid TLC: Rf 0.58 (ethyl acetate);
$^1$H-NMR (300 MHz, CDCl$_3$): δ 0.76-2.13, 2.25, 2.35-2.50, 2.90-3.03, 3.60-3.73, 3.82-3.92, 3.92-4.06, 4.35-4.49, 5.55-5.73, 6.83-6.89, 6.86-6.94, 6.96, 7.22.

Example 17 (38)

4-{(3S,5aR,6R,7R,8aS)-6-[(1E,3S)-4-(2,5-difluorophenoxy)-3-hydroxy-1-buten-1-yl]-7-hydroxyoctahydro-2H-cyclopenta[b]oxepin-3-yl}butanoic acid TLC: Rf 0.44 (dichloromethane:methanol=10:1);
$^1$H-NMR (300 MHz, CD$_3$OD): δ 0.90-1.71, 1.71-1.86, 1.84-2.11, 2.25, 2.34-2.52, 2.90-3.03, 3.56-3.75, 3.85-4.14, 4.37-4.56, 5.51-5.78, 6.49-6.73, 6.82-7.00, 7.00-7.18.

Example 17 (39)

{(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}acetic acid TLC: Rf 0.50 (dichloromethane:methanol=5:1);
$^1$H-NMR (300 MHz, CD$_3$OD): δ 1.01-1.21, 1.33-1.62, 1.66-1.95, 1.95-2.18, 2.44, 2.94-3.12, 3.66, 3.94-4.08, 4.40-4.48, 5.57-5.72, 6.63, 6.92, 7.07.

Example 17 (40)

4-{(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoic acid TLC: Rf 0.49 (dichloromethane:methanol=7:1);
$^1$H-NMR (300 MHz, CD$_3$OD): δ 1.38-1.86, 1.98-2.13, 2.29, 2.38, 3.46, 3.68, 3.76-3.87, 3.95-4.06, 4.40-4.49, 5.57-5.72, 6.63, 6.93, 7.08.

Example 17 (41)

4-{(3S,5aR,6R,7R,8aS)-6-[(1E,3R)-4-(cyclohexyloxy)-3-hydroxy-1-buten-1-yl]-7-hydroxyoctahydro-2H-cyclopenta[b]oxepin-3-yl}butanoic acid TLC: Rf 0.81 (dichloromethane:methanol=4:1);
$^1$H-NMR (300 MHz, CDCl$_3$): δ 0.95-1.90, 2.05-2.15, 2.32-2.37, 2.43-2.52, 2.89-2.97, 3.27-3.33, 3.51-3.55, 3.66-3.75, 3.93-4.08, 4.25-4.31, 5.50-5.64.

Example 17 (42) to Example 17 (45)

Using (3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one, using 4-ethoxy-4-oxobutylzinc bromide or a corresponding organozinc reagent in place of it, and using dimethyl-(3-phenoxy-2-oxopropyl)-phosphonate or a corresponding phosphonic acid salt in place of it, the compounds produced using the methods described in items of Example 16 (2) to Example 16 (42) were subjected to the same objective operations as those of Example 17 (1) to obtain the following Example compounds.

Example 17 (42)

4-[(3S,5aR,6R,7R,8aS)-6-{(1E,3R)-4-[2-fluoro-5-(trifluoromethyl)phenoxy]-3-hydroxy-1-buten-1-yl}-7-hydroxyoctahydro-2H-cyclopenta[b]oxepin-3-yl]butanoic acid TLC: Rf 0.38 (ethyl acetate:methanol=9:1);
$^1$H-NMR (300 MHz, DMSO-d$_6$): δ 11.97, 7.52-7.39, 7.31, 5.55, 5.48, 5.16, 4.60, 4.30, 4.04-4.00, 3.90-3.81, 3.48, 2.83, 2.27, 2.15, 1.89-1.70, 1.66-1.18, 1.11-0.83.

Example 17 (43)

4-{(3S,5aR,6R,7R,8aS)-6-[(1E,3R)-4-(2,6-difluorophenoxy)-3-hydroxy-1-buten-1-yl]-7-hydroxyoctahydro-2H-cyclopenta[b]oxepin-3-yl}butanoic acid TLC: Rf 0.36 (ethyl acetate:methanol=9:1);
$^1$H-NMR (300 MHz, DMSO-d$_6$): δ 11.97, 7.12-7.07, 5.54, 5.47, 5.07, 4.60, 4.23, 3.97-3.82, 3.48, 2.83, 2.27, 2.15, 1.88-1.72, 1.65-1.20, 1.07-0.85.

Example 17 (44)

4-[(3S,5aR,6R,7R,8aS)-7-hydroxy-6-{(1E,3R)-3-hydroxy-4-[3-(trifluoromethoxy)phenoxy]-1-buten-1-yl}octahydro-2H-cyclopenta[b]oxepin-3-yl]butanoic acid TLC: Rf 0.36 (ethyl acetate:methanol=9:1);
$^1$H-NMR (300 MHz, DMSO-d$_6$): δ 11.96, 7.39, 6.99-6.88, 5.55, 5.48, 5.11, 4.60, 4.28, 3.90-3.83, 3.50, 2.83, 2.27, 2.15, 1.90-1.73, 1.67-1.20, 1.12-0.85.

Example 17 (45)

4-[(3S,5aR,6R,7R,8aS)-6-{(1E,3R)-4-[2-fluoro-3-(trifluoromethyl)phenoxy]-3-hydroxy-1-buten-1-yl}-7-hydroxyoctahydro-2H-cyclopenta[b]oxepin-3-yl]butanoic acid TLC: Rf 0.32 (ethyl acetate:methanol=9:1);
$^1$H-NMR (300 MHz, DMSO-d$_6$): δ 11.96, 7.53, 7.33-7.23, 5.55, 5.47, 5.18, 4.61, 4.31, 4.03-3.95, 3.89-3.81, 3.50, 2.83, 2.27, 2.15, 1.90-1.69, 1.65-1.17, 1.11-0.82.

Example 18 (1)

2-Propanyl 4-{(3S,5aR,6R,7R,8aS)-7-hydroxy-6-[(3R)-3-hydroxy-4-phenoxybutyl]octahydro-2H-cyclopenta[b]oxepin-3-yl}butanoate

[Chemical formula 41]

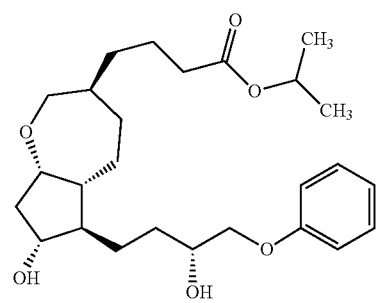

Under the hydrogen atmosphere, palladium-carbon (15 mg) was added to a 2-propanol solution (62 mL) of the compound (71 mg, 1.59 mmol) obtained in Example 16 (1), and the mixture was stirred at room temperature for 3 hours and 20 minutes. The reaction solution was filtered with Celite (trade name), concentrated under reduced pressure, and purified with a column apparatus (Hiflash-SI, Size S, ethyl acetate:hexane=1:1→ethyl acetate) manufactured by Yamazen Corporation to obtain a titled compound (63 mg) having the following physical property values.

TLC: Rf 0.55 (ethyl acetate);
$^1$H-NMR (300 MHz, CDCl$_3$): δ 0.92-1.19, 1.22, 1.35-1.99, 2.15-2.29, 2.33-2.59, 2.81-3.01, 3.58-4.18, 4.81-5.16, 6.78-7.11, 7.15-7.46.

Example 18 (2) to Example 18 (4)

Using the compounds produced in Example 16 (2), Example 16 (3) or Example 16 (25), and using dimethyl-(3-phenoxy-2-oxopropyl)-phosphonate or a corresponding phosphonic acid salt in place of it, these substances were subjected to the same objective operations as those of Example 18 (1) to obtain the following Example compounds.

Example 18 (2)

2-Propanyl 4-{(3S,5aR,6R,7R,8aS)-7-hydroxy-6-[(3R)-3-hydroxy-5-phenylpentyl]octahydro-2H-cyclopenta[b]oxepin-3-yl}butanoate TLC: Rf 0.82 (ethyl acetate:methanol=10:1);
$^1$H-NMR (300 MHz, CDCl$_3$): δ 0.94-1.18, 1.22, 1.31-1.97, 2.12-2.30, 2.59-2.73, 2.73-2.85, 2.85-2.95, 3.53-3.76, 3.86-4.08, 4.85-5.08, 7.05-7.37.

Example 18 (3)

2-Propanyl 4-{(3S,5aR,6R,7R,8aS)-6-[4-(3-chlorophenoxy)-3-hydroxybutyl]-7-hydroxyoctahydro-2H-cyclopenta[b]oxepin-3-yl}butanoate TLC: Rf 0.58 (dichloromethane:methanol=5:1);
$^1$H-NMR (300 MHz, CDCl$_3$): δ 0.70-1.99, 2.16-2.29, 2.30-2.64, 2.92, 3.66-3.78, 3.78-3.87, 3.90-4.10, 4.89-5.09, 6.80, 6.91, 6.95, 7.20.

Example 18 (4)

2-Propanyl 4-{(3S,5aR,6R,7R,8aS)-6-[4-(2,5-difluorophenoxy)-3-hydroxybutyl]-7-hydroxyoctahydro-2H-cyclopenta[b]oxepin-3-yl}butanoate TLC: Rf 0.42 (isopropyl alcohol:hexane=1:5);
$^1$H-NMR (300 MHz, CDCl$_3$): δ 0.94-1.19, 1.19-1.25, 1.33-1.97, 2.13-2.73, 2.91, 3.66-3.80, 3.81-4.16, 4.90-5.10, 6.52-6.65, 6.65-6.76, 6.93-7.09.

Example 19 (1) to Example 19 (4)

Using the compounds produced in Example 18 (1) to Example 18 (4), these compounds were subjected to the same objective operations as those of Example 17 (1) to obtain the following Example compounds.

Example 19 (1)

4-{(3S,5aR,6R,7R,8aS)-7-hydroxy-6-[(3R)-3-hydroxy-4-phenoxybutyl]octahydro-2H-cyclopenta[b]oxepin-3-yl}butanoic acid

[Chemical formula 42]

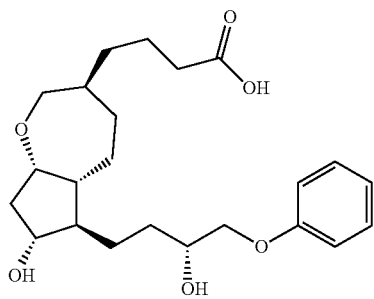

TLC: Rf 0.39 (dichloromethane:methanol=9:1);
$^1$H-NMR (300 MHz, CDCl$_3$): δ 0.92-1.23, 1.36-1.98, 2.15-2.29, 2.33, 2.84-2.99, 3.67-3.78, 3.79-3.87, 3.88-4.07, 6.81-7.04, 7.15-7.41.

Example 19 (2)

4-{(3S,5aR,6R,7R,8aS)-7-hydroxy-6-[(3R)-3-hydroxy-5-phenylpentyl]octahydro-2H-cyclopenta[b]oxepin-3-yl}butanoic acid TLC: Rf 0.65 (ethyl acetate:methanol=10:1);
$^1$H-NMR (300 MHz, CDCl$_3$): δ 0.94-1.18, 1.22, 1.31-1.97, 2.12-2.30, 2.59-2.73, 2.73-2.85, 2.85-2.95, 3.53-3.76, 3.86-4.08, 4.85-5.08, 7.05-7.37.

Example 19 (3)

4-{(3S,5aR,6R,7R,8aS)-6-[4-(3-chlorophenoxy)-3-hydroxybutyl]-7-hydroxyoctahydro-2H-cyclopenta[b]oxepin-3-yl}butanoic acid TLC: Rf 0.58 (dichloromethane:methanol=5:1);
$^1$H-NMR (300 MHz, CD$_3$OD): δ 0.80-1.85, 1.85-2.06, 2.17-2.43, 2.91-3.04, 3.53-3.68, 3.82-4.04, 6.83-6.89, 6.89-6.94, 6.95, 7.22.

Example 19 (4)

4-{(3S,5aR,6R,7R,8aS)-6-[4-(2,5-difluorophenoxy)-3-hydroxybutyl]-7-hydroxyoctahydro-2H-cyclopenta[b]oxepin-3-yl}butanoic acid TLC: Rf 0.41 (dichloromethane:methanol=10:1);
$^1$H-NMR (300 MHz, CD$_3$OD): δ 0.93-1.24, 1.37-1.84, 1.84-2.01, 2.16-2.38, 2.90-3.04, 3.50-3.70, 3.83-4.08, 6.53-6.71, 6.82-7.00, 6.99-7.15.

Example 20

Ethyl 2-({[(1R,2S,3R,4S)-2-allyl-3-({[dimethyl(2-methyl-2-propanyl)silyl]oxy}methyl)-4-(tetrahydro-2H-pyran-2-yloxy)cyclopentyl]oxy}methyl)acrylate Under the argon atmosphere, an anhydrous DMF (17 mL) solution of the compound (3.9 g) produced in Example 3 was added to an anhydrous DMF (20 mL) solution of sodium hydride (631 mg) under ice-cooling, and the mixture was stirred at room temperature for 1 hour. Subsequently, ethyl 2-(bromomethyl)acrylate (2.91 mL) was added, and the mixture was stirred at room temperature for 3 hours. An aqueous saturated ammonium chloride solution was added, and this was extracted with hexane:ethyl acetate (2:1). After the organic layer was washed with water and a saturated saline, and dried with sodium sulfate, the solvent was concentrated under reduced pressure. The resulting residue was purified with a column apparatus (Hiflash-SI, Size 3 L, hexane:ethyl acetate=100:0→93:7→86:14) manufactured Yamazen Corporation to obtain a titled compound (4.32 g) having the following physical property values.

TLC: Rf 0.53 (hexane:ethyl acetate=5:1).

Example 21

Ethyl(5aR,6S,7R,8aS)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-carboxylate Under the argon atmosphere, the compound (200 mg, 0.190 mmol) produced in Example 20 was dissolved in toluene (40 mL). A Schrock's catalyst (48 mg, 0.062 mmol) was added to react the compound at 60° C. for 18 hours. After allowing to stand, the reaction was concentrated, and purified by silica gel column chromatography (hexane:ethyl acetate=95:10→50:50) to obtain a titled compound (3.2 mg) having the following physical property values. TLC: Rf 0.53 (hexane:ethyl acetate=4:1).

Example 22 (1)

Ethyl(3S,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-carboxylate Example 22 (2)

Ethyl(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-carboxylate Under the argon atmosphere, a 5% rhodium-alumina powder (160 mg) and, subsequently, ethanol (40 mL) were added to the compound (1.6 g) produced in Example 21, and the mixture was stirred at room temperature for 4 hours under the hydrogen atmosphere. The reaction solution was filtered with Celite (trade name), and concentrated under reduced pressure, and the resulting residue was purified with a column apparatus (Hiflash-SI, Size 3 L, hexane:ethyl acetate=95:5→8:2) manufactured by Yamazen Corporation to obtain a compound (270 mg) of Example 22 (1) and its diastereomer (Example 22 (2)) (1.2 g) having the following physical property values.

The diastereomer (1.2 g) was dissolved in absolute ethanol (13 mL), a 20% ethanol solution of sodium ethoxide (895 mg) was added at room temperature under the argon atmosphere, and the mixture was stirred at room temperature overnight. After diluted with ethyl acetate, an aqueous saturated ammonium chloride solution was added, and this was extracted with ethyl acetate. After the organic layer was washed with water and a saturated saline, and dried with sodium sulfate, the solvent was concentrated under reduced pressure. The resulting residue was purified with a column apparatus (Hiflash-SI, Size 3 L, hexane:ethyl acetate=95:5→8:2) manufactured by Yamazen Corporation to obtain an Example compound 22 (1) (757 mg) having the following physical property values.

TLC: Rf 0.58 (hexane:ethyl acetate=4:1) (compound of Example 22 (1));
TLC: Rf 0.44 (hexane:ethyl acetate=5:1) (compound of Example 22 (2)).

Example 23

[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]methanol Under the argon atmosphere, a THF (6.4 mL) solution of the compound (945 mg) produced in Example 22 (1) was added to a THF (4 mL) solution of lithium aluminum hydride (87 mg) under ice-cooling, and the mixture was stirred at room temperature for 20 minutes. After diluted with MTBE, an aqueous saturated sodium sulfate solution was added, filtered with Celite (trade name), and concentrated under reduced pressure to obtain a titled compound (884 mg) having the following physical property values.
TLC: Rf 0.16 (hexane:ethyl acetate=2:1).

Example 24

2-methyl-2-propanyl {[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]methoxy}acetate A 50% aqueous sodium hydroxide solution (0.6 mL) which had been prepared separately was added to a benzene (1.8 mL) solution of the compound (300 mg) produced in Example 23 under ice-cooling. Subsequently, a tetrabutylammonium hydrogen sulfate salt (61 mg) and tert-butyl bromoacetate (282 mg) were added, and the mixture was stirred at room temperature overnight. After diluted with MTBE, water was added, and this was extracted with MTBE. The extract was washed with water and a saturated saline, and dried with sodium sulfate, and the solvent was concentrated under reduced pressure. The resulting residue was purified with a column apparatus (SMB Silica Column, 10 μm, Size 60, hexane:ethyl acetate=95:5→90:10→80:20→50:50) manufactured by Yamazen Corporation to obtain a titled compound (371 mg) having the following physical property values.
TLC: Rf 0.54 (hexane:ethyl acetate=4:1).

Example 25

{[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]methoxy}acetic acid A 2N aqueous sodium hydroxide solution (1.75 mL) was added to a methanol (5.25 mL) solution of the compound (371 mg) produced in Example 24 at room temperature, and the mixture was stirred at 50° C. for 3.5 hours. After methanol was distilled off by concentration under reduced pressure, the residue was diluted with MTBE, made acidic with ice-cooled 2N hydrochloric acid, and extracted with ethyl acetate. The extract was washed with water and a saturated saline, and dried with sodium sulfate, and the solvent was concentrated under reduced pressure to obtain a titled compound (371 mg) having the following physical property values. The resulting titled compound was used in a next reaction without purification.
TLC: Rf 0.24 (ethyl acetate).

Example 26

2-Propanyl {[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]methoxy}acetate Under the argon atmosphere, the compound produced in Example 25 was dissolved in DMF (2.8 mL), potassium carbonate (242 mg) and 2-iodopropane (0.105 mL) were sequentially added at room temperature, and the mixture was stirred at 50° C. overnight. The reaction solution was diluted with ethyl acetate, water was added, and this was extracted with ethyl acetate. The extract was washed with water and a saturated saline, and dried with sodium sulfate, and the solvent was concentrated under reduced pressure to obtain a titled compound (371 mg) having the following physical property values. The resulting titled compound was used in a next reaction without purification.

TLC: Rf 0.81 (hexane:ethyl acetate=1:1).

Example 27

2-Propanyl {[(3R,5aR,6S,7R,8aS)-6-(hydroxymethyl)-7-(tetrahydro-2H-pyran-2-yloxy)octahydro-2H-cyclopenta[b]oxepin-3-yl]methoxy}acetate Under the argon atmosphere, a 1M THF solution (1.4 mL) of tetrabutylammonium fluoride was added to the compound produced in Example 26 at room temperature, and the mixture was stirred for 6 hours. The reaction solution was diluted with ethyl acetate, an aqueous saturated ammonium chloride solution was added, and this was extracted with ethyl acetate. The extract was washed with water and a saturated saline, and dried with sodium sulfate, and the solvent was concentrated under reduced pressure. The resulting residue was purified with a column apparatus (Hiflash-SI, Size M, hexane:ethyl acetate=90:10→50:50→20:80) manufactured by Yamazen Corporation to obtain a titled compound (240 mg) having the following physical property values.

TLC: Rf 0.21 (hexane:ethyl acetate=1:1).

Example 28

2-Propanyl({(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}methoxy)acetate

[Chemical formula 43]

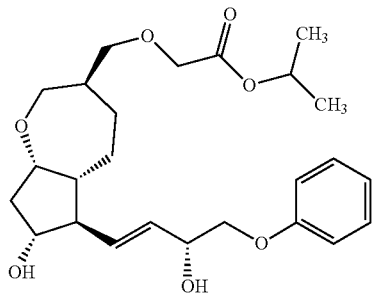

The compound (152 mg) produced in Example 27 was subjected to the same objective operations as those of Example 13→Example 14→Example 15→Example 16 (1) using dimethyl-(3-phenoxy-2-oxopropyl)-phosphonate, to obtain a titled compound (72 mg) having the following physical property values.

TLC: Rf 0.33 (ethyl acetate);
$^1$H-NMR (300 MHz, CDCl$_3$): δ 1.10-1.31, 1.40-1.57, 1.58-2.19, 2.19-2.29, 2.41-2.55, 2.61-2.73, 3.24-3.41, 3.63-3.81, 3.83-4.07, 4.14-4.25, 4.42-4.60, 4.98-5.16, 5.58-5.73, 6.86-7.03, 7.23-7.34.

Example 28 (1) to Example 28 (17)

Using (3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one, using ethyl 2-(bromomethyl)acrylate, and using dimethyl-(3-phenoxy-2-oxopropyl)-phosphonate or a corresponding phosphonic acid salt in place of it, these substances were subjected to the same objective operations as those of Example 20→Example 21→Example 22 (1) or Example 22 (2)→Example 23→Example 24→Example 25→Example 26→Example 27→Example 28 to obtain the following Example compounds.

Example 28 (1)

2-Propanyl({(3R,5aR,6R,7R,8aS)-6-[(1E,3R)-4-(3-chlorophenoxy)-3-hydroxy-1-buten-1-yl]-7-hydroxy-octahydro-2H-cyclopenta[b]oxepin-3-yl}methoxy)acetate TLC: Rf 0.65 (ethyl acetate);
$^1$H-NMR (300 MHz, CDCl$_3$): δ 1.10-1.32, 1.40-1.60, 1.61-2.21, 2.40-2.56, 3.05-3.18, 3.25-3.41, 3.67-3.82, 3.82-3.92, 3.92-4.06, 4.15-4.25, 4.45-4.58, 4.99-5.17, 5.56-5.76, 6.75-6.84, 6.87-6.99, 7.15-7.24.

Example 28 (2)

2-Propanyl({(3R,5aR,6R,7R,8aS)-6-[(1E,3R)-4-(2-fluorophenoxy)-3-hydroxy-1-buten-1-yl]-7-hydroxy-octahydro-2H-cyclopenta[b]oxepin-3-yl}methoxy)acetate TLC: Rf 0.49 (ethyl acetate);
$^1$H-NMR (300 MHz, CDCl$_3$): δ 1.09-1.35, 1.39-2.24, 2.40-2.57, 2.62-2.78, 3.10, 3.24-3.41, 3.64-3.80, 3.85-4.10, 4.14-4.26, 4.48-4.60, 4.98-5.15, 5.55-5.77, 6.82-7.14.

Example 28 (3)

2-Propanyl({(3R,5aR,6R,7R,8aS)-6-[(1E,3R)-4-(3-fluorophenoxy)-3-hydroxy-1-buten-1-yl]-7-hydroxy-octahydro-2H-cyclopenta[b]oxepin-3-yl}methoxy)acetate TLC: Rf 0.45 (ethyl acetate);
$^1$H-NMR (300 MHz, CDCl$_3$): δ 1.07-1.34, 1.39-2.22, 2.37-2.58, 3.04-3.17, 3.24-3.40, 3.64-3.80, 3.83-3.91, 3.91-4.07, 4.11-4.28, 4.45-4.59, 4.95-5.17, 5.54-5.77, 6.53-6.74, 7.10-7.32.

Example 28 (4)

2-Propanyl({(3R,5aR,6R,7R,8aS)-6-[(1E,3R)-4-(4-fluorophenoxy)-3-hydroxy-1-buten-1-yl]-7-hydroxy-octahydro-2H-cyclopenta[b]oxepin-3-yl}methoxy)acetate TLC: Rf 0.42 (ethyl acetate);
$^1$H-NMR (300 MHz, CDCl$_3$): δ 1.10-1.34, 1.38-2.22, 2.39-2.57, 3.05-3.17, 3.25-3.40, 3.65-3.79, 3.80-3.88, 3.88-4.09, 4.10-4.26, 4.43-4.58, 4.97-5.15, 5.54-5.74, 6.77-6.91, 6.90-7.04.

Example 28 (5)

2-Propanyl({(3R,5aR,6R,7R,8aS)-6-[(1E,3R)-4-(4-chlorophenoxy)-3-hydroxy-1-buten-1-yl]-7-hydroxy-octahydro-2H-cyclopenta[b]oxepin-3-yl}methoxy)acetate TLC: Rf 0.57 (ethyl acetate);
$^1$H-NMR (300 MHz, CDCl$_3$): δ 1.10-1.30, 1.40-1.58, 1.61-2.22, 2.40-2.56, 3.11, 3.25-3.41, 3.65-3.80, 3.80-3.90, 3.90-4.06, 4.13-4.25, 4.44-4.59, 4.98-5.16, 5.55-5.75, 6.76-6.91, 7.16-7.30.

Example 28 (6)

2-Propanyl({(3R,5aR,6R,7R,8aS)-7-hydroxy-6-[(1E,3R)-3-hydroxy-4-(3-methylphenoxy)-1-buten-1-yl]octahydro-2H-cyclopenta[b]oxepin-3-yl}methoxy)acetate TLC: Rf 0.60 (ethyl acetate);
$^1$H-NMR (300 MHz, CDCl$_3$): δ 1.09-1.31, 1.41-1.60, 1.61-2.22, 2.33, 2.41-2.57, 3.05-3.17, 3.25-3.41, 3.66-3.81, 3.81-3.91, 3.92-4.06, 4.14-4.26, 4.45-4.58, 4.99-5.16, 5.57-5.74, 6.66-6.83, 7.16.

Example 28 (7)

2-Propanyl({(3R,5aR,6R,7R,8aS)-7-hydroxy-6-[(1E,3R)-3-hydroxy-4-(4-methylphenoxy)-1-buten-1-yl]octahydro-2H-cyclopenta[b]oxepin-3-yl}methoxy)acetate TLC: Rf 0.57 (ethyl acetate);
$^1$H-NMR (300 MHz, CDCl$_3$): δ 1.09-1.35, 1.40-1.59, 1.61-2.20, 2.29, 2.39-2.60, 3.03-3.18, 3.25-3.41, 3.65-3.79, 3.79-3.89, 3.89-4.07, 4.13-4.26, 4.44-4.56, 4.98-5.16, 5.56-5.74, 6.74-6.86, 7.07.

Example 28 (8)

2-Propanyl({(3R,5aR,6R,7R,8aS)-6-[(1E,3R)-4-(2-chlorophenoxy)-3-hydroxy-1-buten-1-yl]-7-hydroxyoctahydro-2H-cyclopenta[b]oxepin-3-yl}methoxy)acetate TLC: Rf 0.33 (ethyl acetate);
$^1$H-NMR (300 MHz, CDCl$_3$): δ 1.09-1.30, 1.40-1.57, 1.61-2.21, 2.40-2.56, 2.71, 3.04-3.18, 3.25-3.41, 3.65-3.81, 3.88-4.04, 4.08, 4.15-4.24, 4.52-4.62, 5.00-5.16, 5.95-5.76, 6.88-6.98, 7.17-7.28, 7.33-7.41.

Example 28 (9)

2-Propanyl({(3R,5aR,6R,7R,8aS)-7-hydroxy-6-[(1E,3R)-3-hydroxy-4-(2-methylphenoxy)-1-buten-1-yl]octahydro-2H-cyclopenta[b]oxepin-3-yl}methoxy)acetate TLC: Rf 0.37 (ethyl acetate);
$^1$H-NMR (300 MHz, CDCl$_3$): δ 1.10-1.29, 1.41-1.57, 1.61-2.20, 2.24, 2.41-2.55, 3.11, 3.25-3.40, 3.66-3.81, 3.86-3.94, 3.94-4.05, 4.20, 4.48-4.60, 5.00-5.17, 5.60-5.76, 6.82, 6.85-6.93, 7.10-7.20.

Example 28 (10)

2-Propanyl({(3R,5aR,6R,7R,8aS)-6-[(1E,3R)-4-(3-chloro-2-fluorophenoxy)-3-hydroxy-1-buten-1-yl]-7-hydroxyoctahydro-2H-cyclopenta[b]oxepin-3-yl}methoxy)acetate TLC: Rf 0.37 (ethyl acetate);
$^1$H-NMR (300 MHz, CDCl$_3$): δ 1.05-1.33, 1.38-2.25, 2.38-2.56, 2.65-2.74, 2.96-3.19, 3.24-3.41, 3.73, 3.87-4.10, 4.14-4.26, 4.46-4.61, 4.98-5.15, 5.56-5.75, 6.83-6.92, 6.93-7.05.

Example 28 (11)

2-Propanyl({(3R,5aR,6R,7R,8aS)-6-[(1E,3R)-4-(3,5-dichlorophenoxy)-3-hydroxy-1-buten-1-yl]-7-hydroxyoctahydro-2H-cyclopenta[b]oxepin-3-yl}methoxy)acetate TLC: Rf 0.51 (ethyl acetate);
$^1$H-NMR (300 MHz, CDCl$_3$): δ 1.10-1.32, 1.38-2.24, 2.32-2.43, 2.43-2.57, 3.05-3.19, 3.25-3.42, 3.65-3.82, 3.82-3.91, 3.92-4.06, 4.14-4.27, 4.44-4.62, 4.99-5.18, 5.25-5.77, 6.82, 6.98.

Example 28 (12)

2-Propanyl({(3R,5aR,6R,7R,8aS)-6-[(1E,3R)-4-(3-chloro-5-fluorophenoxy)-3-hydroxy-1-buten-1-yl]-7-hydroxyoctahydro-2H-cyclopenta[b]oxepin-3-yl}methoxy)acetate TLC: Rf 0.73 (ethyl acetate:methanol=9:1);
$^1$H-NMR (300 MHz, CDCl$_3$): δ 1.10-1.37, 1.37-2.24, 2.39-2.59, 3.04-3.18, 3.24-3.41, 3.65-3.80, 3.81-3.91, 3.91-4.05, 4.13-4.27, 4.43-4.58, 4.99-5.16, 5.55-5.75, 6.48-6.59, 6.64-6.78.

Example 28 (13)

2-Propanyl({(3R,5aR,6R,7R,8aS)-6-[(1E,3R)-4-(3,5-difluorophenoxy)-3-hydroxy-1-buten-1-yl]-7-hydroxyoctahydro-2H-cyclopenta[b]oxepin-3-yl}methoxy)acetate TLC: Rf 0.79 (ethyl acetate:methanol=9:1);
$^1$H-NMR (300 MHz, CDCl$_3$): δ 1.07-1.32, 1.37-2.22, 2.39-2.58, 3.04-3.18, 3.24-3.41, 3.64-3.79, 3.81-3.90, 3.90-4.06, 4.12-4.27, 4.43-4.58, 4.97-5.15, 5.55-5.74, 6.35-6.54.

Example 28 (14)

2-Propanyl({(3R,5aR,6R,7R,8aS)-6-[(1E,3R)-4-(2,3-difluorophenoxy)-3-hydroxy-1-buten-1-yl]-7-hydroxyoctahydro-2H-cyclopenta[b]oxepin-3-yl}methoxy)acetate TLC: Rf 0.77 (ethyl acetate:methanol=9:1);
$^1$H-NMR (300 MHz, CDCl$_3$): δ 1.08-1.35, 1.36-2.32, 2.38-2.57, 2.63-2.84, 3.03-3.19, 3.22-3.44, 3.62-3.82, 3.87-4.10, 4.13-4.28, 4.46-4.63, 4.98-5.20, 5.54-5.77, 6.66-6.87, 6.90-7.05.

Example 28 (15)

2-Propanyl({(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}methoxy)acetate TLC: Rf 0.77 (ethyl acetate:methanol=9:1);
$^1$H-NMR (300 MHz, CDCl$_3$): δ 1.07-1.32, 1.36-2.21, 2.27, 2.40-2.56, 2.77, 3.04-3.20, 3.23-3.41, 3.64-3.80, 3.84-4.08, 4.13-4.27, 4.48-4.61, 4.98-5.16, 5.54-5.74, 6.53-6.65, 6.65-6.76, 6.94-7.08.

Example 28 (16)

2-Propanyl({(3R,5aR,6R,7R,8aS)-6-[(1E,3R)-4-(5-chloro-2-fluorophenoxy)-3-hydroxy-1-buten-1-yl]-7-hydroxyoctahydro-2H-cyclopenta[b]oxepin-3-yl}methoxy)acetate TLC: Rf 0.52 (ethyl acetate);
$^1$H-NMR (300 MHz, CDCl$_3$): δ 1.10-1.30, 1.40-1.57, 1.61-2.21, 2.42-2.55, 2.60, 3.05-3.17, 3.25-3.40, 3.66-3.82, 3.87-

4.08, 4.15-4.25, 4.49-4.61, 4.99-5.16, 5.55-5.75, 6.85-6.93, 6.93-7.06.

Example 28 (17)

2-Propanyl({(3R,5aR,6R,7R,8aS)-6-[(1E,3R)-4-(3-chloro-4-fluorophenoxy)-3-hydroxy-1-buten-1-yl]-7-hydroxyoctahydro-2H-cyclopenta[b]oxepin-3-yl}methoxy)acetate TLC: Rf 0.40 (ethyl acetate);
$^1$H-NMR (300 MHz, CDCl$_3$): δ 1.11-1.30, 1.40-1.60, 1.62-2.21, 2.41-2.55, 3.05-3.17, 3.26-3.40, 3.66-3.79, 3.79-3.89, 3.89-4.06, 4.15-4.25, 4.45-4.56, 4.99-5.15, 5.56-5.73, 6.73-6.80, 6.94, 7.00-7.09.

Example 29

({(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}methoxy)acetic acid

[Chemical formula 44]

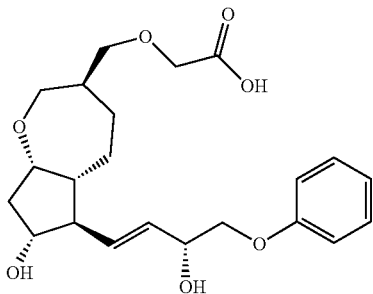

The compound (7.3 mg) produced in Example 28 was subjected to the same objective operations as those of Example 17 (1) to obtain a titled compound (7.1 mg) having the following physical property values.
TLC: Rf 0.13 (chloroform:methanol:water=10:1:0.1)
$^1$H-NMR (300 MHz, CDCl$_3$): δ 1.08-1.23, 1.39-1.57, 1.59-1.95, 1.95-2.20, 2.42-2.55, 3.03-3.16, 3.27-3.42, 3.66-3.78, 3.84-4.03, 4.05, 4.15-4.25, 4.46-4.57, 5.56-5.74, 6.86-7.02, 7.23-7.33.

Example 29 (1) to Example 29 (17)

The compounds produced in Example 28 (1) to Example 28 (17) were subjected to the same objective operations as those of Example 29, respectively, to obtain the following Example compounds.

Example 29 (1)

({(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}methoxy)acetic acid TLC: Rf 0.21 (chloroform:methanol:acetic acid=20:1:0.1);
$^1$H-NMR (300 MHz, CDCl$_3$): δ 1.09-1.31, 1.40-2.26, 2.42-2.57, 3.03-3.17, 3.29-3.46, 3.68-3.81, 3.82-3.91, 3.93-4.09, 4.14-4.23, 4.46-4.58, 5.57-5.75, 6.75-6.84, 6.87-6.99, 7.14-7.24.

Example 29 (2)

({(3R,5aR,6R,7R,8aS)-6-[(1E,3R)-4-(2-fluorophenoxy)-3-hydroxy-1-buten-1-yl]-7-hydroxyoctahydro-2H-cyclopenta[b]oxepin-3-yl}methoxy)acetic acid TLC: Rf 0.23 (chloroform:methanol=5:1);
$^1$H-NMR (300 MHz, CD$_3$OD): δ 1.07-1.24, 1.32-1.48, 1.49-1.63, 1.67-2.13, 2.35-2.51, 3.06-3.18, 3.20-3.42, 3.59-3.74, 3.90-4.08, 4.11-4.23, 4.38-4.49, 5.57-5.70, 6.83-6.95, 6.99-7.16.

Example 29 (3)

({(3R,5aR,6R,7R,8aS)-6-[(1E,3R)-4-(3-fluorophenoxy)-3-hydroxy-1-buten-1-yl]-7-hydroxyoctahydro-2H-cyclopenta[b]oxepin-3-yl}methoxy)acetic acid TLC: Rf 0.26 (chloroform:methanol=5:1);
$^1$H-NMR (300 MHz, CD$_3$OD): δ 1.09-1.24, 1.35-1.49, 1.49-1.61, 1.67-2.12, 2.37-2.50, 3.07-3.18, 3.21-3.40, 3.60-3.72, 3.83-4.05, 4.13-4.23, 4.34-4.47, 5.56-5.73, 6.56-6.83, 7.16-7.32.

Example 29 (4)

({(3R,5aR,6R,7R,8aS)-6-[(1E,3R)-4-(4-fluorophenoxy)-3-hydroxy-1-buten-1-yl]-7-hydroxyoctahydro-2H-cyclopenta[b]oxepin-3-yl}methoxy)acetic acid TLC: Rf 0.24 (chloroform:methanol=5:1);
$^1$H-NMR (300 MHz, CD$_3$OD): δ 1.09-1.24, 1.34-1.49, 1.49-1.61, 1.68-2.11, 2.35-2.51, 3.08-3.19, 3.20-3.42, 3.60-3.73, 3.80-4.07, 4.12-4.24, 4.34-4.46, 5.56-5.71, 6.83-7.06.

Example 29 (5)

({(3R,5aR,6R,7R,8aS)-6-[(1E,3R)-4-(4-chlorophenoxy)-3-hydroxy-1-buten-1-yl]-7-hydroxyoctahydro-2H-cyclopenta[b]oxepin-3-yl}methoxy)acetic acid TLC: Rf 0.42 (chloroform:methanol:acetic acid=10:1:0.1);
$^1$H-NMR (300 MHz, CD$_3$OD): δ 1.06-1.28, 1.32-1.63, 1.64-2.12, 2.35-2.51, 3.06-3.19, 3.20-3.43, 3.57-3.74, 3.81-4.10, 4.10-4.24, 4.33-4.47, 5.52-5.73, 6.84-6.97, 7.16-7.29.

Example 29 (6)

({(3R,5aR,6R,7R,8aS)-7-hydroxy-6-[(1E,3R)-3-hydroxy-4-(3-methylphenoxy)-1-buten-1-yl]octahydro-2H-cyclopenta[b]oxepin-3-yl}methoxy)acetic acid TLC: Rf 0.43 (chloroform:methanol:acetic acid=10:1:0.1);
$^1$H-NMR (300 MHz, CD$_3$OD): δ 1.07-1.26, 1.33-1.64, 1.66-2.13, 2.29, 2.37-2.51, 3.05-3.19, 3.20-3.44, 3.57-3.75, 3.82-4.08, 4.10-4.24, 4.32-4.47, 5.54-5.72, 6.62-6.80, 7.04-7.17.

Example 29 (7)

({(3R,5aR,6R,7R,8aS)-7-hydroxy-6-[(1E,3R)-3-hydroxy-4-(4-methylphenoxy)-1-buten-1-yl]octahydro-2H-cyclopenta[b]oxepin-3-yl}methoxy)acetic acid TLC: Rf 0.45 (chloroform:methanol:acetic acid=10:1:0.1);
$^1$H-NMR (300 MHz, CD$_3$OD): δ 1.06-1.27, 1.31-1.64, 1.65-2.11, 2.25, 2.35-2.52, 3.04-3.20, 3.19-3.43, 3.58-3.74, 3.77-4.10, 4.10-4.24, 4.31-4.46, 5.52-5.72, 6.79, 7.04.

Example 29 (8)

({(3R,5aR,6R,7R,8aS)-6-[(1E,3R)-4-(2-chlorophenoxy)-3-hydroxy-1-buten-1-yl]-7-hydroxyoctahydro-2H-cyclopenta[b]oxepin-3-yl}methoxy)acetic acid TLC: Rf 0.18 (chloroform:methanol:water=10:1:0.1);
$^1$H-NMR (300 MHz, CD$_3$OD): δ 1.09-1.23, 1.32-1.46, 1.48-1.62, 1.68-2.11, 2.36-2.51, 3.11, 3.22-3.40, 3.60-3.73, 3.86-4.06, 4.12-4.22, 4.40-4.50, 5.58-5.73, 6.90, 7.05, 7.23, 7.33.

Example 29 (9)

{(3R,5aR,6R,7R,8aS)-7-hydroxy-6-[(1E,3R)-3-hydroxy-4-(2-methylphenoxy)-1-buten-1-yl]octahydro-2H-cyclopenta[b]oxepin-3-yl}methoxy)acetic acid TLC: Rf 0.18 (chloroform:methanol:water=10:1:0.1
$^1$H-NMR (300 MHz, CD$_3$OD): δ 1.08-1.22, 1.34-1.49, 1.55, 1.68-2.10, 2.20, 2.43, 3.07-3.17, 3.25-3.39, 3.66, 3.86-4.07, 4.17, 4.38-4.47, 5.57-5.73, 6.76-6.89, 7.04-7.14.

Example 29 (10)

({(3R,5aR,6R,7R,8aS)-6-[(1E,3R)-4-(3-chloro-2-fluorophenoxy)-3-hydroxy-1-buten-1-yl]-7-hydroxyoctahydro-2H-cyclopenta[b]oxepin-3-yl}methoxy) acetic acid TLC: Rf 0.29 (dichloromethane:methanol=5:1);
$^1$H-NMR (300 MHz, CD$_3$OD): δ 1.05-1.62, 1.63-2.09, 2.35-2.52, 3.06-3.19, 3.19-3.42, 3.58-3.73, 3.93-4.06, 4.12-4.22, 4.37-4.52, 5.52-5.74, 6.89-7.18.

Example 29 (11)

({(3R,5aR,6R,7R,8aS)-6-[(1E,3R)-4-(3,5-dichlorophenoxy)-3-hydroxy-1-buten-1-yl]-7-hydroxyoctahydro-2H-cyclopenta[b]oxepin-3-yl}methoxy) acetic acid TLC: Rf 0.24 (dichloromethane:methanol=5:1);
$^1$H-NMR (300 MHz, CD$_3$OD): δ 1.06-1.62, 1.65-2.13, 2.37-2.52, 3.07-3.18, 3.20-3.45, 3.60-3.74, 3.82-4.07, 4.12-4.23, 4.33-4.47, 5.53-5.73, 6.93, 6.98.

Example 29 (12)

({(3R,5aR,6R,7R,8aS)-6-[(1E,3R)-4-(3-chloro-5-fluorophenoxy)-3-hydroxy-1-buten-1-yl]-7-hydroxyoctahydro-2H-cyclopenta[b]oxepin-3-yl}methoxy) acetic acid TLC: Rf 0.46 (dichloromethane:methanol:acetic acid=3:1:0.2);
$^1$H-NMR (300 MHz, CD$_3$OD): δ 1.07-1.33, 1.32-1.63, 1.63-2.13, 2.36-2.50, 3.06-3.18, 3.20-3.41, 3.60-3.73, 3.84-4.07, 4.12-4.23, 4.35-4.46, 5.53-5.72, 6.68, 6.75, 6.79-6.85.

Example 29 (13)

({(3R,5aR,6R,7R,8aS)-6-[(1E,3R)-4-(3,5-difluorophenoxy)-3-hydroxy-1-buten-1-yl]-7-hydroxyoctahydro-2H-cyclopenta[b]oxepin-3-yl}methoxy) acetic acid TLC: Rf 0.47 (dichloromethane:methanol:acetic acid=3:1:0.2);
$^1$H-NMR (300 MHz, CD$_3$OD): δ 1.08-1.30, 1.32-1.63, 1.68-2.12, 2.36-2.51, 3.06-3.18, 3.21-3.41, 3.59-3.74, 3.82-4.06, 4.12-4.24, 4.35-4.48, 5.54-5.73, 6.39-6.64.

Example 29 (14)

({(3R,5aR,6R,7R,8aS)-6-[(1E,3R)-4-(2,3-difluorophenoxy)-3-hydroxy-1-buten-1-yl]-7-hydroxyoctahydro-2H-cyclopenta[b]oxepin-3-yl}methoxy) acetic acid TLC: Rf 0.48 (dichloromethane:methanol:acetic acid=3:1:0.2);
$^1$H-NMR (300 MHz, CD$_3$OD): δ 1.08-1.28, 1.33-1.61, 1.65-2.12, 2.36-2.52, 3.12, 3.20-3.42, 3.58-3.73, 3.90-4.07, 4.11-4.22, 4.38-4.49, 5.53-5.73, 6.75-6.86, 6.86-6.95, 6.97-7.11.

Example 29 (15)

({(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}methoxy) acetic acid TLC: Rf 0.48 (dichloromethane:methanol:acetic acid=3:1:0.2);
$^1$H-NMR (300 MHz, CD$_3$OD): δ 1.06-1.24, 1.32-1.65, 1.66-2.13, 2.35-2.52, 3.05-3.18, 3.22-3.42, 3.58-3.73, 3.88-4.07, 4.11-4.24, 4.37-4.51, 5.53-5.74, 6.54-6.69, 6.84-6.96, 6.99-7.14.

Example 29 (16)

({(3R,5aR,6R,7R,8aS)-6-[(1E,3R)-4-(5-chloro-2-fluorophenoxy)-3-hydroxy-1-buten-1-yl]-7-hydroxyoctahydro-2H-cyclopenta[b]oxepin-3-yl}methoxy) acetic acid TLC: Rf 0.12 (chloroform:methanol:acetic acid=10:1:0.1);
$^1$H-NMR (300 MHz, CD$_3$OD): δ 1.07-1.24, 1.33-1.49, 1.49-1.62, 1.67-2.10, 2.36-2.51, 3.07-3.19, 3.19-3.42, 3.60-3.72, 3.93-4.07, 4.11-4.23, 4.38-4.48, 5.55-5.72, 6.90, 7.07, 7.13.

Example 29 (17)

({(3R,5aR,6R,7R,8aS)-6-[(1E,3R)-4-(3-chloro-4-fluorophenoxy)-3-hydroxy-1-buten-1-yl]-7-hydroxyoctahydro-2H-cyclopenta[b]oxepin-3-yl}methoxy) acetic acid TLC: Rf 0.11 (chloroform:methanol:acetic acid=10:1:0.1);
$^1$H-NMR (300 MHz, CD$_3$OD): δ 1.08-1.25, 1.34-1.63, 1.67-2.09, 2.37-2.51, 3.07-3.18, 3.20-3.42, 3.59-3.73, 3.82-4.07, 4.12-4.23, 4.35-4.44, 5.54-5.72, 6.87, 7.04, 7.12.

Example 30

2-Propanyl 4-[(3S,5aR,6R,7R,8aS)-6-[(1E)-3,3-difluoro-4-phenoxy-1-buten-1-yl]-7-(tetrahydro-2H-pyran-2-yloxy)octahydro-2H-cyclopenta[b]oxepin-3-yl]butanoate Under the argon atmosphere, the compound (280 mg, 0.53 mmol) produced in Example 14 was dissolved in (2-methoxyethyl)aminosulfur trifluoride (977 μL, 5.30 mmol), and the mixture was stirred at room temperature for 4 days and 7 hours. The reaction solution was slowly poured into an ice-cooled aqueous saturated sodium bicarbonate solution, and the aqueous layer was extracted with ethyl acetate two times. The organic layer was washed with a saturated saline, and dried with anhydrous sodium sulfate. Purification with a column apparatus (Hiflash-SI, Size M, hexane→ethyl acetate: hexane=3:7) manufactured by Yamazen Corporation afforded a titled compound (171 mg) having the following physical property values.

TLC: Rf 0.54 (hexane:ethyl acetate=3:7).

Example 31

2-Propanyl 4-{(3S,5aR,6R,7R,8aS)-6-[(1E)-3,3-difluoro-4-phenoxy-1-buten-1-yl]-7-hydroxyoctahydro-2H-cyclopenta[b]oxepin-3-yl}butanoate

[Chemical formula 45]

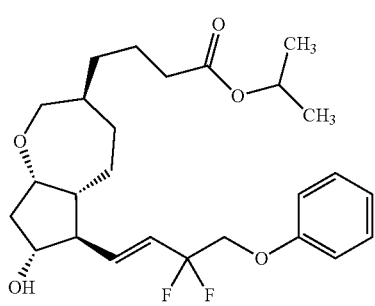

The compound produced in Example 30 was subjected to the same objective operations as those of Example 16 (1) to obtain a titled compound having the following physical property values.

TLC: Rf 0.42 (ethyl acetate:hexane=1:1);
$^1$H-NMR (300 MHz, CDCl$_3$): δ 0.87-1.19, 1.18-1.26, 1.35-1.96, 2.11-2.30, 2.35-2.56, 2.84-2.97, 3.67-3.84, 3.90-4.11, 4.19, 4.89-5.08, 5.68-5.87, 5.95-6.11, 6.85-6.95, 6.95-7.05, 7.21-7.35.

Example 32

4-{(3S,5aR,6R,7R,8aS)-6-[(1E)-3,3-difluoro-4-phenoxy-1-buten-1-yl]-7-hydroxyoctahydro-2H-cyclopenta[b]oxepin-3-yl}butanoic acid

[Chemical formula 46]

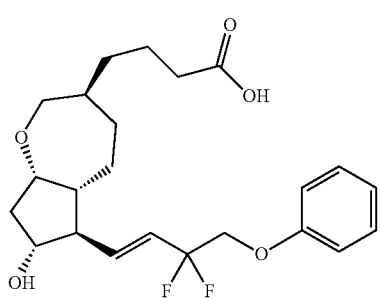

The compound produced in Example 31 was subjected to the same objective operations as those of Example 17 (1) to obtain a titled compound having the following physical property values.

TLC: Rf 0.34 (dichloromethane:methanol=9:1);
$^1$H-NMR (300 MHz, CDCl$_3$): δ 0.90-1.23, 1.36-1.96, 2.12-2.27, 2.33, 2.40-2.53, 2.84-2.98, 3.71-3.83, 3.90-4.10, 4.19, 5.69-5.88, 5.95-6.10, 6.86-6.94, 6.95-7.05, 7.21-7.35.

Example 32 (1) to Example 32 (5)

Using the compound produced in Example 13, and using a corresponding phosphonic acid salt in place of dimethyl-(3-phenoxy-2-oxopropyl)-phosphonate, these substances were subjected to the same objective operations as those of Example 14→Example 30→Example 31→Example 32 to obtain the following Example compounds.

Example 32 (1)

4-{(3S,5aR,6R,7R,8aS)-6-[(1E)-3,3-difluoro-4-(2-fluorophenoxy)-1-buten-1-yl]-7-hydroxyoctahydro-2H-cyclopenta[b]oxepin-3-yl}butanoic acid TLC: Rf 0.52 (ethyl acetate);
$^1$H-NMR (300 MHz, DMSO-d$_6$): δ 11.98, 7.28-7.19, 7.13, 6.99, 6.06, 5.75, 4.79, 4.43, 3.90-3.84, 3.57, 2.84, 2.30, 2.15, 1.97, 1.80-1.64, 1.61-1.21, 1.11-0.86.

Example 32 (2)

4-{(3S,5aR,6R,7R,8aS)-6-[(1E)-3,3-difluoro-4-(3-fluorophenoxy)-1-buten-1-yl]-7-hydroxyoctahydro-2H-cyclopenta[b]oxepin-3-yl}butanoic acid TLC: Rf 0.55 (ethyl acetate);
$^1$H-NMR (300 MHz, DMSO-d$_6$): δ 11.98, 7.33, 6.94-6.78, 6.05, 5.75, 4.81, 4.39, 3.91-3.85, 3.58, 2.85, 2.31, 2.16, 1.98, 1.81-1.67, 1.60-1.22, 1.12-0.87.

Example 32 (3)

4-{(3S,5aR,6R,7R,8aS)-6-[(1E)-4-(3-chlorophenoxy)-3,3-difluoro-1-buten-1-yl]-7-hydroxyoctahydro-2H-cyclopenta[b]oxepin-3-yl}butanoic acid TLC: Rf 0.55 (ethyl acetate);
$^1$H-NMR (300 MHz, DMSO-d$_6$): δ 11.98, 7.32, 7.11, 7.04, 6.98, 6.05, 5.74, 4.80, 4.40, 3.91-3.84, 3.58, 2.84, 2.31, 2.16, 1.97, 1.81-1.64, 1.59-1.21, 1.10-0.86.

Example 32 (4)

4-[(3S,5aR,6R,7R,8aS)-6-{(1E)-3,3-difluoro-4-[3-(trifluoromethyl)phenoxy]-1-buten-1-yl}-7-hydroxy-octahydro-2H-cyclopenta[b]oxepin-3-yl]butanoic acid TLC: Rf 0.68 (ethyl acetate);
$^1$H-NMR (300 MHz, DMSO-d$_6$): δ 11.98, 7.55, 7.35-7.32, 6.06, 5.76, 4.80, 4.48, 3.91-3.84, 3.58, 2.84, 2.31, 2.16, 1.98, 1.81-1.64, 1.59-1.21, 1.10-0.86.

Example 32 (5)

4-{(3S,5aR,6R,7R,8aS)-6-[(1E)-4-(2,5-difluorophenoxy)-3,3-difluoro-1-buten-1-yl]-7-hydroxyoctahydro-2H-cyclopenta[b]oxepin-3-yl}butanoic acid TLC: Rf 0.65 (ethyl acetate);
$^1$H-NMR (300 MHz, DMSO-d$_6$): δ 11.98, 7.33-7.23, 6.82, 6.07, 5.74, 4.80, 4.48, 3.91-3.84, 3.58, 2.85, 2.31, 2.16, 1.97, 1.81-1.64, 1.60-1.21, 1.10-0.86.

Example 33

[(3S,5aR,6S,7R,8aS)-6-(hydroxymethyl)-7-(tetrahydro-2H-pyran-2-yloxy)octahydro-2H-cyclopenta[b]oxepin-3-yl]methyl acetate Pyridine (0.335 mL), acetic acid anhydride (0.294 mL) and N-dimethylaminopyridine (small amount) were sequentially added to a dichloromethane (5 mL) solution of the compound (884 mg) produced in Example 23 at room temperature, and the mixture was stirred for 3 hours. This was diluted with ethyl acetate, and water was added, followed by extraction with ethyl acetate. The organic layer was sequentially washed with 1N hydrochloric acid, an aqueous saturated sodium bicarbonate solution, and a saturated saline, and dried with sodium sulfate, and the solvent was concentrated under reduced pressure. To the resulting residue was added THF (0.5 mL), a 1M THF solution (5 mL) of N-tetrabutylammonium fluoride was added under the argon atmosphere and ice-cooling, and the mixture was stirred for 5 hours. The reaction solution was poured into an ice-cooled aqueous saturated ammonium chloride solution, and this was extracted with ethyl acetate. The organic layer was washed with water, and a saturated saline, and dried with sodium sulfate, and the solvent was concentrated under reduced pressure. The resulting residue was purified by preparative chromatograph (Hi-flash-SI, Size L, hexane:ethyl acetate=8:2→1:1→0:1) manufactured Yamazen Corporation to obtain a titled compound (616 mg) having the following physical property values.

TLC: Rf 0.19 (hexane:ethyl acetate=1:1).

Example 34

[(3S,5aR,6R,7R,8aS)-6-[(1E)-3-oxo-4-phenoxy-1-buten-1-yl]-7-(tetrahydro-2H-pyran-2-yloxy)octahydro-2H-cyclopenta[b]oxepin-3-yl]methyl acetate The compound (616 mg) produced in Example 33 was subjected to the same objective operations as those of Example 13→Example 14 to obtain a titled compound (568 mg) having the following physical property values.

TLC: Rf 0.53 (hexane:ethyl acetate=1:1).

Example 35

[(3R,5aR,6R,7R,8aS)-6-[(1E,3R)-4-phenoxy-3-(tetrahydro-2H-pyran-2-yloxy)-1-buten-1-yl]-7-(tetrahydro-2H-pyran-2-yloxy)octahydro-2H-cyclopenta[b]oxepin-3-yl]methanol The compound produced in Example 34 was subjected to the same objective operations as those of Example 15→Example 11 to obtain a titled compound (568 mg) having the following physical property values.

TLC: Rf 0.26 (hexane:ethyl acetate=1:1).

Example 36

Ethyl 2-[(3S,5aR,6R,7R,8aS)-6-[(1E,3S)-4-phenoxy-3-(tetrahydro-2H-pyran-2-yloxy)-1-buten-1-yl]-7-(tetrahydro-2H-pyran-2-yloxy)octahydro-2H-cyclopenta[b]oxepin-3-yl]-1,3-thiazole-4-carboxylate Under the argon atmosphere, diisopropylethylamine (0.3 mL) was added to a DMSO (0.5 mL)-ethyl acetate (1.0 mL) solution of the compound (150 mg) synthesized in Example 35 under ice-cooling, subsequently, pyridine-sulfur trioxide (139 mg) were added, and the mixture was stirred for about 30 minutes. After dilution with ethyl acetate, an aqueous saturated ammonium chloride solution was added, and this was extracted with ethyl acetate. The organic layer was washed with an aqueous saturated ammonium chloride solution, an aqueous saturated sodium bicarbonate solution, water and a saturated saline, dried with sodium sulfate, and concentrated under reduced pressure. The resulting residue was dissolved in toluene (1.5 mL), triethylamine (0.061 mL) and L-cysteine ethyl ester hydrochloride (81 mg) were sequentially added under ice-cooling, and the mixture was stirred at room temperature overnight. After dilution with ethyl acetate, water was added, and this was extracted with ethyl acetate. The extract was sequentially washed with an aqueous citric acid solution, an aqueous saturated sodium bicarbonate solution, water and a saturated saline, dried with sodium sulfate, and concentrated under reduced pressure. The resulting residue was dissolved in toluene (5.8 mL), manganese dioxide (756 mg) was added, and the mixture was stirred at 60° C. overnight. This was filtered with Celite (trade name), and washed with ethyl acetate plural times, and the filtrate was concentrated under reduced pressure. The resulting residue was purified with preparative chromatograph (SMB Silica Column 10 μm, Size 20, hexane:ethyl acetate=9:1→75:25→6:4→3:7) manufactured by Yamazen Corporation to obtain a title compound (65 mg) having the following physical property values.

TLC: Rf 0.42, 0.38 (hexane:ethyl acetate=3:2).

Example 37

Ethyl 2-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}-1,3-thiazole-4-carboxylate

[Chemical formula 47]

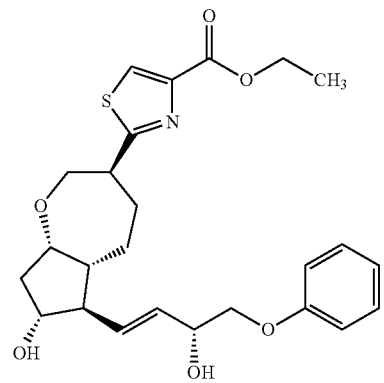

To an ethanol (1.0 mL) solution of the compound (65 mg) produced in Example 36 was added p-toluenesulfonic acid monohydrate (2.0 mg) at room temperature, and the mixture was stirred overnight. An aqueous saturated sodium bicarbonate solution was added, and this was extracted with ethyl acetate. The extract was washed with water and a saturated saline, dried with sodium sulfate, and concentrated under reduced pressure. The resulting residue was purified with preparative chromatograph (SMB silica column, 10 μm, Size 20, hexane:ethyl acetate=1:1→0:1) manufactured by Yamazen Corporation to obtain a titled compound (47 mg) having the following physical property values.

TLC: Rf 0.65 (ethyl acetate:methanol=9:1);

$^1$H-NMR (300 MHz, CDCl$_3$): δ 1.39, 1.59-1.97, 2.04, 2.10-2.35, 2.45-2.60, 3.39-3.56, 3.69-3.83, 3.89, 3.97-4.05, 4.10, 4.31-4.47, 4.49-4.60, 5.61-5.76, 6.86-7.01, 7.24-7.34, 8.04.

Example 38

2-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}-1,3-thiazole-4-carboxylic acid

[Chemical formula 48]

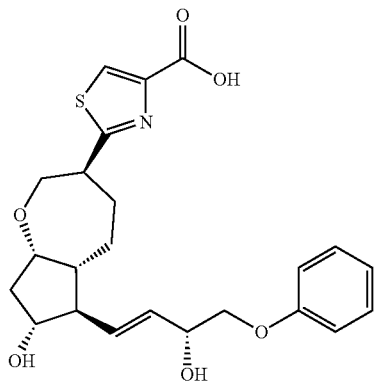

The compound produced in Example 37 was subjected to the same objective operations as those of Example 17 (1) to obtain a titled compound having the following physical property values.

TLC: Rf 0.19 (chloroform:methanol:water=10:1:0.1);

$^1$H-NMR (300 MHz, CDCl$_3$): δ 1.56-2.01, 2.10-2.39, 2.47-2.61, 3.35-3.55, 3.78, 3.85-3.94, 3.97-4.06, 4.11, 4.38, 4.51-4.60, 5.63-5.77, 6.87-7.02, 7.23-7.35, 8.15.

Example 39

Ethyl({[(3S,5aR,6R,7R,8aS)-6-[(1E,3R)-4-phenoxy-3-(tetrahydro-2H-pyran-2-yloxy)-1-buten-1-yl]-7-(tetrahydro-2H-pyran-2-yloxy)octahydro-2H-cyclopenta[b]oxepin-3-yl]methyl}thio)acetate Triethylamine (0.039 mL) and methanesulfonic acid chloride (0.020 mL) were sequentially added to an anhydrous THF (1.7 mL) solution of the compound (90 mg) produced in Example 35 under ice-cooling, and the mixture was stirred for 1 hour. This was diluted with ethyl acetate, and water was added, followed by extraction. The extract was sequentially washed with an aqueous saturated sodium bicarbonate solution, water and a saturated saline, and dried with sodium sulfate. The solvent was concentrated under reduced pressure to obtain the residue (109 mg). The resulting residue was dissolved in an anhydrous THF (1.7 mL) solution, and ethyl thioglycolate (0.029 mL) was added. Subsequently, 60% sodium hydride (11 mg) was added at room temperature, and the mixture was stirred at 50° C. overnight. This was diluted with ethyl acetate, and water was added, followed by extraction. The extract was sequentially washed with an aqueous saturated sodium bicarbonate solution, water and a saturated saline, and dried with sodium sulfate. The solvent was concentrated under reduced pressure, and the resulting residue was purified by preparative chromatograph (Hiflash-SI, Size S, hexane:ethyl acetate=75:25→0:100) manufactured by Yamazen Corporation to obtain a titled compound (61 mg) having the following physical property values.

TLC: Rf 0.81 (hexane:ethyl acetate=1:2).

Example 40

Ethyl[({(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}methyl)thio]acetate

[Chemical formula 49]

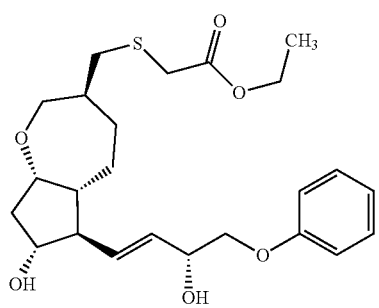

The compound produced in Example 39 was subjected to the same objective operations as those of Example 37 to obtain a titled compound having the following physical property values.

TLC: Rf 0.16 (hexane:ethyl acetate=1:2);

$^1$H-NMR (300 MHz, CDCl$_3$): δ 1.00-1.18, 1.24-1.33, 1.38-1.56, 1.56-1.85, 1.84-2.19, 2.25, 2.39-2.55, 2.68, 2.98, 3.13-3.22, 3.64-3.79, 3.83-3.92, 3.92-4.03, 4.09-4.26, 4.45-4.58, 5.57-5.72, 6.85-7.02, 7.22-7.34.

Example 41

[({(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}methyl)thio]acetic acid

[Chemical formula 50]

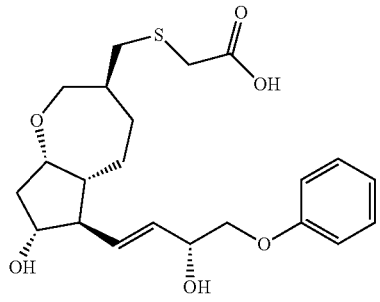

The compound produced in Example 40 was subjected to the same objective operations as those of Example 17 (1) to obtain a titled compound having the following physical property values.

TLC: Rf 0.35 (chloroform:methanol:acetic acid=10:1:0.1);

$^1$H-NMR (300 MHz, CDCl$_3$): δ 1.01-1.17, 1.38-1.55, 1.60-1.86, 1.86-2.20, 2.41-2.55, 2.93-3.05, 3.22, 3.67-3.79, 3.84-3.93, 3.93-4.04, 4.14-4.24, 4.48-4.57, 5.59-5.74, 6.87-7.03, 7.24-7.34.

Example 42 (1) to Example 42 (2)

Using the compound produced in Example 4, and using a corresponding organozinc reagent in place of 4-ethyoxy-4-oxobutylzinc bromide, these substances were subjected to the same objective operations as those of Example 5→Example 6→Example 12→Example 13→Example 14→Example 15→Example 16 (1) to obtain the following compounds.

Example 42 (1)

Ethyl 3-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}benzoate (Low Polar Body)

[Chemical formula 51]

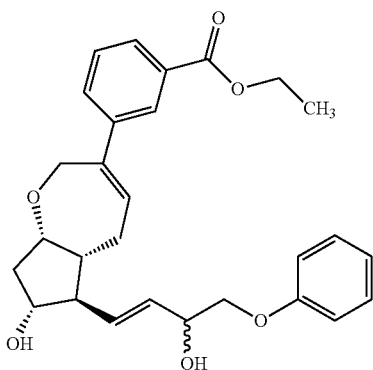

TLC: Rf 0.43 (hexane:ethyl acetate=1:2);
$^1$H-NMR (300 MHz, CDCl$_3$): δ 1.35-1.44, 1.71-1.86, 2.04, 2.11-2.32, 2.43-2.64, 2.64-2.86, 3.73-3.94, 4.02, 4.07-4.21, 4.31-4.50, 4.50-4.61, 4.81-4.95, 5.61-5.81, 5.96-6.10, 6.86-7.03, 7.21-7.46, 7.84-7.98.

Example 42 (2)

Ethyl 3-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}benzoate (High Polar Body)

TLC: Rf 0.33 (hexane:ethyl acetate=1:2);
$^1$H-NMR (300 MHz, CDCl$_3$): δ 1.40, 1.72-1.86, 2.08-2.32, 2.44-2.58, 2.61, 2.75, 3.74-3.86, 3.85-3.96, 3.98-4.07, 4.15, 4.33-4.51, 4.55, 4.83-4.95, 5.62-5.80, 5.97-6.08, 6.88-7.03, 7.23-7.46, 7.88-7.96.

Example 43 (1) to Example 43 (5)

Using the compound produced in Example 4, using 4-ethoxy-4-oxobutylzinc bromide or a corresponding organozinc reagent in place of it, and using dimethyl-(3-phenox-2-oxopropyl)-phosphonate or a corresponding phosphonic acid salt in place of it, these substances were subjected to the same objective preparations as those of Example 5→Example 6→Example 12→Example 13→Example 14→Example 15→Example 16 (1)→Example 17 (1) to obtain the following Example compounds.

Example 43 (1)

3-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}benzoic acid (low polar body)

[Chemical formula 52]

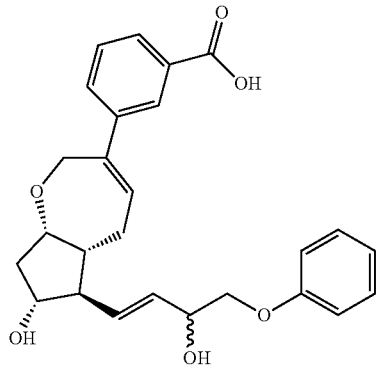

TLC: Rf 0.19 (chloroform:methanol:acetic acid=10:1:0.1);
$^1$H-NMR (300 MHz, CD$_3$OD): δ 1.58-1.74, 2.07-2.32, 2.40-2.55, 2.60-2.78, 3.66-3.80, 3.84-3.95, 3.95-4.04, 4.10-4.22, 4.38-4.56, 4.77-4.99, 5.62-5.79, 6.04, 6.85-6.99, 7.19-7.29, 7.39, 7.45-7.54, 7.83-7.94.

Example 43 (2)

3-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}benzoic acid (high polar body)

TLC: Rf 0.20 (chloroform:methanol:acetic acid=10:1:0.1);
$^1$H-NMR (300 MHz, CD$_3$OD): δ 1.58-1.74, 2.04-2.31, 2.40-2.55, 2.66, 3.66-3.81, 3.86-4.02, 4.15, 4.37-4.54, 4.73-5.00, 5.59-5.76, 6.01, 6.85-6.98, 7.19-7.30, 7.39, 7.45-7.53, 7.84-7.94.

Example 43 (3)

3-{(5aR,6R,7R,8aS)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}propanoic acid TLC: Rf 0.56 (dichloromethane:methanol=5:1);
$^1$H-NMR (300 MHz, CDCl$_3$): δ 1.61-1.79, 1.84-2.29, 2.36-2.60, 3.67-3.83, 3.86-4.16, 4.38, 4.48-4.67, 5.41-5.57, 5.57-5.87, 6.78-7.08, 7.19-7.36.

Example 43 (4)

4-{(5aR,6R,7R,8aS)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}butanoic acid TLC: Rf 0.38 (dichloromethane:methanol=9:1);
$^1$H-NMR (300 MHz, CDCl$_3$): δ 1.62-1.79, 1.81-2.26, 2.26-2.64, 3.69-3.81, 3.82-3.91, 3.92-4.07, 4.39, 4.49-4.59, 5.42-5.53, 5.55-5.79, 6.75-7.12, 7.19-7.41.

Example 43 (5)

4-{(5aR,6R,7R,8aS)-7-hydroxy-6-[(1E,3S)-3-hydroxy-1-octen-1-yl]-5,5a,6,7,8,8a-hexahydro-2H-cyclopenta[b]oxepin-3-yl}butanoic acid TLC: Rf 0.33 (dichloromethane:methanol=9:1);
$^1$H-NMR (300 MHz, CDCl$_3$): δ 0.68-1.01, 1.06-2.93, 3.58-3.87, 3.88-4.24, 4.38, 5.25-5.81.

Example 44 (1) to Example 44 (4)

Using the compound produced in Example 4, and using 4-ethoxy-4-oxobutylzinc bromide or a corresponding organozinc reagent in place of it, these substances were subjected to the same objective operations as those of Example 5→Example 6→Example 7→Example 8→Example 12→Example 13→Example 14→Example 15→Example 16 (1) to obtain the following Example compounds.

Example 44 (1)

2-propanyl 5-{(5aR,6R,7R,8aS)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}pentanoate

[Chemical formula 53]

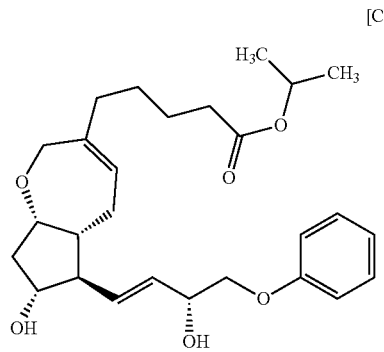

TLC: Rf 0.21 (hexane:ethyl acetate=1:2);
$^1$H-NMR (300 MHz, CDCl$_3$): δ 1.22, 1.31-1.44, 1.51-1.78, 1.77-1.98, 2.01-2.31, 2.37-2.61, 3.49, 3.68-3.82, 3.83-3.93, 3.93-4.06, 4.39, 4.47-4.59, 4.92-5.06, 5.37-5.49, 5.57-5.75, 6.86-7.02, 7.22-7.35.

Example 44 (2)

2-propanyl 5-{(5aR,6R,7R,8aS)-6-[(1E,3R)-4-(3-chlorophenoxy)-3-hydroxy-1-buten-1-yl]-7-hydroxy-5,5a,6,7,8,8a-hexahydro-2H-cyclopenta[b]oxepin-3-yl}pentanoate TLC: Rf 0.26 (hexane:ethyl acetate=2:3);
$^1$H-NMR (300 MHz, CDCl$_3$): δ 1.22, 1.31-1.46, 1.52-1.65, 1.65-1.77, 1.77-1.97, 2.01-2.32, 2.37-2.65, 3.68-3.82, 3.82-3.92, 3.92-4.05, 4.39, 4.51, 4.91-5.08, 5.39-5.50, 5.57-5.75, 6.77-6.84, 6.89-6.99, 7.20.

Example 44 (3)

2-propanyl 5-{(5aR,6R,7R,8aS)-7-hydroxy-6-[(1E,3R)-3-hydroxy-4-(3-methylphenoxy)-1-buten-1-yl]-5,5a,6,7,8,8a-hexahydro-2H-cyclopenta[b]oxepin-3-yl}pentanoate TLC: Rf 0.29 (hexane:ethyl acetate=1:2);
$^1$H-NMR (300 MHz, CDCl$_3$): δ 1.20-1.25, 1.31-1.45, 1.51-1.65, 1.65-1.77, 1.77-1.98, 2.00-2.21, 2.21-2.30, 2.30-2.36, 2.38-2.61, 3.68-3.80, 3.81-3.91, 3.91-4.06, 4.32-4.45, 4.51, 4.92-5.07, 5.38-5.49, 5.57-5.74, 6.66-6.83, 7.16.

Example 44 (4)

2-propanyl 6-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}hexanoate TLC: Rf 0.15 (hexane:ethyl acetate=1:1);
$^1$H-NMR (300 MHz, CDCl$_3$): δ 1.18-1.46, 1.52-1.99, 2.00-2.30, 2.30-2.62, 2.77, 3.65-3.81, 3.81-4.08, 4.39, 4.46-4.59, 4.90-5.09, 5.42, 5.55-5.75, 6.85-7.03, 7.22-7.35.

Example 45 (1) to Example 45 (4)

The compounds produced in Example 44 (1) to Example 44 (4) were subjected to the same objective operations as those of Example 17 (1) to obtain the following Example compounds.

Example 45 (1)

5-{(5aR,6R,7R,8aS)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}pentanoic acid

[Chemical formula 54]

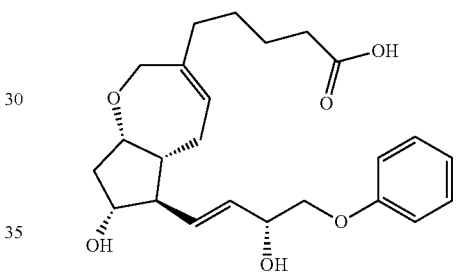

TLC: Rf 0.53 (ethyl acetate:methanol=9:1);
$^1$H-NMR (300 MHz, CDCl$_3$): δ 1.31-1.48, 1.52-1.77, 1.77-1.98, 2.00-2.25, 2.34, 2.38-2.59, 3.67-3.81, 3.84-4.06, 4.38, 4.46-4.58, 5.43, 5.57-5.73, 6.85-7.02, 7.21-7.35.

Example 45 (2)

5-{(5aR,6R,7R,8aS)-6-[(1E,3R)-4-(3-chlorophenoxy)-3-hydroxy-1-buten-1-yl]-7-hydroxy-5,5a,6,7,8,8a-hexahydro-2H-cyclopenta[b]oxepin-3-yl}pentanoic acid TLC: Rf 0.36 (chloroform:methanol:acetic acid=10:1:0.1);
$^1$H-NMR (300 MHz, CDCl$_3$): δ 1.22-1.49, 1.53-1.76, 1.78-1.98, 1.98-2.28, 2.34, 2.38-2.57, 3.67-3.80, 3.84-3.93, 3.93-4.05, 4.32-4.44, 4.45-4.55, 5.44, 5.56-5.73, 6.77-6.84, 6.89-6.98, 7.20.

Example 45 (3)

5-{(5aR,6R,7R,8aS)-7-hydroxy-6-[(1E,3R)-3-hydroxy-4-(3-methylphenoxy)-1-buten-1-yl]-5,5a,6,7,8,8a-hexahydro-2H-cyclopenta[b]oxepin-3-yl}pentanoic acid TLC: Rf 0.43 (chloroform:methanol:acetic acid=10:1:0.1);
$^1$H-NMR (300 MHz, CD$_3$OD): δ 1.32-1.47, 1.49-1.65, 1.79-1.94, 2.01-2.13, 2.21-2.34, 2.34-2.54, 3.62-3.75, 3.83-4.08, 4.32-4.45, 5.44, 5.54-5.72, 6.66-6.78, 7.06-7.17.

Example 45 (4)

6-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}hexanoic acid TLC: Rf 0.57 (chloroform:methanol:acetic acid=10:1:0.1);
$^1$H-NMR (300 MHz, CD$_3$OD): δ 1.22-1.46, 1.50-1.67, 1.77-1.94, 1.98-2.13, 2.27, 2.36-2.55, 3.60-3.76, 3.85-4.08, 4.31-4.47, 5.38-5.48, 5.56-5.72, 6.86-6.97, 7.20-7.30.

Example 46

Ethyl 4-{(5aR,6R,7R,8aS)-7-hydroxy-6-[(1E)-3-hydroxy-4-phenoxy-1-buten-1-yl]octahydro-2H-cyclopenta[b]oxepin-3-yl}butanoate (diastereomer mixture)

Using the compound produced in Example 6, this compound was subjected to the same objective preparations as those of Example 9→Example 12→Example 13→Example 14→Example 15→Example 16 (1) to obtain a titled compound having the following physical property values.
TLC: Rf 0.33 (dichloromethane:methanol=20:1);
$^1$H-NMR (300 MHz, CDCl$_3$): δ 1.21-1.34, 1.37-1.89, 2.09-2.53, 2.57-2.67, 3.41, 3.66-4.06, 4.07-4.23, 4.45-4.56, 5.57-5.73, 6.87-7.05, 7.20-7.36.

Example 47

4-{(5aR,6R,7R,8aS)-7-hydroxy-6-[(1E)-3-hydroxy-4-phenoxy-1-buten-1-yl]octahydro-2H-cyclopenta[b]oxepin-3-yl}butanoic acid (diastereomer mixture)

Using the compound produced in Example 46, this compound was subjected to the same objective operations as those of Example 17 (1) to obtain a titled compound having the following physical property values.
TLC: Rf 0.36 (dichloromethane:methanol=10:1);
$^1$H-NMR (300 MHz, CDCl$_3$): δ 1.09-1.88, 2.08-2.23, 2.26-2.59, 2.85-3.55, 3.60-4.17, 4.45-4.60, 5.52-5.84, 6.84-7.03, 7.13-7.43.

Example 48 (1) to Example 48 (2)

Using the compound produced in Example 3, and using a corresponding alkyl halide in place of 2,3-dibromopropene, these substances were subjected to the same objective preparations as those of Example 4→Example 5→Example 6→Example 7→Example 8→Example 9→Example 12→Example 13→Example 14→Example 15→Example 16 (1) to obtain the following Example compounds.

Example 48 (1)

2-propanyl 3-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}propanoate (diastereomer mixture)

TLC: Rf 0.47 (ethyl acetate);
$^1$H-NMR (300 MHz, CDCl$_3$): δ 1.23, 1.33-1.94, 2.01-2.60, 2.86-3.46, 3.66-4.09, 4.47-4.59, 4.92-5.07, 5.58-5.75, 6.86-7.02, 7.24-7.35.

Example 48 (2)

2-propanyl 5-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}pentanoate (diastereomer mixture)

TLC: Rf 0.19 (hexane:ethyl acetate=1:2);
$^1$H-NMR (300 MHz, CDCl$_3$): δ 0.87-2.03, 2.03-2.33, 2.33-2.57, 2.89, 3.65-4.10, 4.46-4.59, 4.91-5.07, 5.57-5.74, 6.86-7.02, 7.19-7.34.

Example 49 (1) to Example 49 (2)

The compounds produced in Example 48 (1) to Example 48 (2) were subjected to the same objective operations as those of Example 17 (1) to obtain the following Example compounds.

Example 49 (1)

3-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}propanoic acid (diastereomer mixture)

TLC: Rf 0.51 (chloroform:methanol:water=10:1:0.1);
$^1$H-NMR (300 MHz, CDCl$_3$): δ 1.30-1.96, 2.06-2.55, 2.85-3.47, 3.57-4.10, 4.41-4.61, 5.55-5.74, 6.86-7.02, 7.22-7.37.

Example 49 (2)

5-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}pentanoic acid (diastereomer mixture)

TLC: Rf 0.53 (ethyl acetate:methanol=9:1);
$^1$H-NMR (300 MHz, CDCl$_3$): δ 0.88-1.19, 1.20-1.52, 1.52-1.93, 2.05-2.19, 2.27-2.39, 2.40-2.54, 2.89, 3.64-3.77, 3.77-4.08, 4.44-4.57, 5.55-5.72, 6.85-7.03, 7.21-7.36.

Example 50

(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentanol Under the argon atmosphere, carbonylchlorohydridotris(triphenylphosphine)ruthenium (9.5 mg) was added to a toluene solution (1 mL) of the compound (74.1 mg) produced in Example 3, and the reaction mixture was stirred at 80° C. for 3 hours and 30 minutes. Thereafter, a small amount of the reaction mixture was taken, and concentrated to obtain a titled compound having the following physical property values.
TLC: Rf 0.45 (hexane:ethyl acetate=75:25).

Example 51

2-methyl-2-propanyl {[(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentyl]oxy}acetate Under the argon atmosphere, the compound (3.70 g) produced in Example 50 was dissolved in DMF (20 mL). After t-butyl bromoacetate (7.4 mL) was added, sodium hydride (400 mg, 60% in oil) was added four times for every 30 minutes to 60 minutes (total 1600 mg). After stirring at room temperature overnight, water was added to the reaction mixture, the extract obtained by extraction with ethyl acetate was washed with water and a saturated saline, dried with anhydrous magnesium sulfate, and concentrated under reduced pressure. The residue was purified by silica gel column chromatography (hexane:ethyl acetate=95:5→75:25) to obtain a titled compound (3.5 g) having the following physical property values.

TLC: Rf 0.50 (hexane:ethyl acetate=80:20).

Example 52

Allyl {[(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentyl]oxy}acetate The compound (3.37 g) produced in Example 51 was dissolved in THF (10 mL), a 5N aqueous sodium hydroxide solution (5 mL) and methanol (20 mL) were added, and the mixture was stirred at room temperature for 2 hours. To the reaction mixture was added 2N hydrochloric acid, and the extract obtained by extraction with ethyl acetate was washed with water and a saturated saline, dried with anhydrous magnesium sulfate, and concentrated under reduced pressure to obtain carboxylic acid (3.02 g). The carboxylic acid (3.02 g) was dissolved in DMF (15 mL), potassium carbonate (1.60 g) and allyl bromide (1.0 mL) were added, and the mixture was stirred at room temperature overnight. To the reaction mixture was added water, and the extract obtained by extraction with hexane/ethyl acetate (1/1) was washed with water and a saturated saline, dried with anhydrous magnesium sulfate, and concentrated under reduced pressure. The residue was purified by silica gel column chromatography (hexane:ethyl acetate=97:3→80:20) to obtain a titled compound (2.93 g) having the following physical properties.

TLC: Rf 0.50 (hexane:ethyl acetate=80:20).

Example 53 (1)

Methyl(2R)-2-{[(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentyl]oxy}-4-pentenoate

Example 53 (2)

Methyl(2S)-2-{[(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentyl]oxy}-4-pentenoate Under the argon atmosphere, diisopropylamine (2.0 mL) was dissolved in THF (16 mL), and the solution was cooled to 0° C. After a 1.66M n-butyllithiumhexane solution (8.0 mL) was added dropwise, the mixture was stirred at the same temperature for 30 minutes. After this was cooled to −78° C., and trimethylchlorosilane (2.0 mL) was added dropwise, a THF (7 mL) solution of the compound (3.28 g) produced in Example 52 was added dropwise. After stirring at −78° C. for 30 minutes, a temperature was raised to room temperature, and the mixture was stirred for 1 hour. After water was added to the reaction mixture, and this was stirred for 1 hour, 1N hydrochloric acid was added, and the extract obtained by extraction with ethyl acetate was washed with water and a saturated saline, dried with anhydrous magnesium sulfate, and concentrated under reduced pressure. The residue was dissolved in ethyl acetate (40 mL), methanol (4 mL), and a 2.0M trimethylsilyldiazomethanehexane solution (7 mL) were added, and the mixture was stirred at room temperature for 1 hour. After the reaction mixture was concentrated under reduced pressure, the residue was purified by silica gel column chromatography (hexane:ethyl acetate=97:3→80:20) to obtain an Example compound 53 (1) (1.26 g) and an Example compound 53 (2) (1.16 g) having the following physical property values.

TLC: Rf 0.42 (hexane:ethyl acetate=86:14) (compound of Example 53 (1));
TLC: Rf 0.36 (hexane:ethyl acetate=86:14) (compound of Example 53 (2)).

Example 54

Methyl(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-carboxylate The compound (1.26 g) produced in Example 53 (1) was dissolved in dichloromethane (30 mL), a Schrock's catalyst (0.44 g) was added, and the mixture was stirred at room temperature overnight. After the reaction mixture was concentrated under reduced pressure, the residue was purified by silica gel column chromatography (hexane:ethyl acetate=75:25) to obtain a titled compound (0.95 g) having the following physical property values.

TLC: Rf 0.48 (hexane:ethyl acetate=75:25).

Example 55

[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]methanol After lithium aluminum hydride (84 mg) was suspended in THF (2 mL), the suspension was cooled to 0° C., a THF (3 mL) solution of the compound (0.95 g) produced in Example 54 was added dropwise, and the mixture was stirred at 0° C. for 15 minutes. After water was added to the reaction mixture, the extract obtained by addition of 1N hydrochloric acid and extraction was washed with water, an aqueous saturated sodium bicarbonate solution and a saturated saline, dried with anhydrous magnesium sulfate, and concentrated under reduced pressure. The residue was purified by silica gel column chromatography (hexane:ethyl acetate=60:40→40:60) to obtain a titled compound (793 mg) having the following physical property values.

TLC: Rf 0.43 (hexane:ethyl acetate=50:50).

Example 56

2-propanyl(2E)-3-[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]acrylate The compound (165 mg) produced in Example 55 was dissolved in DMSO (2 mL), a Wittig reagent (carboisopropoxymethylenetriphenylphosphorane, 218 mg) and 1-hydroxy-1,2-benziodoxol-3(1H)-one 1-oxide (IBX, 168 mg) were added, and the mixture was stirred at 50° C. for 5 hours. To the reaction mixture were added ethyl acetate and water, and insolubles were filtered. The filtrate was extracted with ethyl acetate, and the extract was washed with an aqueous saturated sodium bicarbonate solution and a saline, dried with anhydrous magnesium sulfate, and concentrated under reduced pressure. The residue was purified by silica gel column chromatography (hexane:ethyl acetate=97:3→80:20) to obtain a titled compound (174 mg) having the following physical property values.

TLC: Rf 0.50 (hexane:ethyl acetate=80:20).

Example 57

2-propanyl 3-[(2R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-2-yl]propanoate The compound (174 mg) produced in Example 56 was dissolved in 2-propanol (2 mL), sodium bicarbonate (20 mg) and 10% palladium carbon (20 mg) were added, and the mixture was stirred at room temperature for 1 hour under the hydrogen atmosphere. The filtrate obtained by filtering the reaction mixture with Celite (trade name) was concentrated under reduced pressure, and the residue was purified by silica gel column chromatography (hexane:ethyl acetate=97:3→80:20) to obtain a titled compound (150 mg) having the following physical property values.

TLC: Rf 0.50 (hexane:ethyl acetate=80:20).

Example 58

2-propanyl 3-[(2R,5aR,6S,7R,8aS)-6-(hydroxymethyl)-7-(tetrahydro-2H-pyran-2-yloxy)octahydro-2H-cyclopenta[b]oxepin-2-yl]propanoate To the compound (143 mg) produced in Example 57 was added 1 mL of 1 mol/L tetrabutylammonium fluoride (THF solution), and the mixture was stirred at room temperature overnight. After the reaction mixture was concentrated under reduced pressure, the residue was purified by silica gel column chromatography (hexane:ethyl acetate=60:40→20:80) to obtain a titled compound (98 mg) having the following physical property values.

TLC: Rf 0.32 (hexane:ethyl acetate=50:50).

Example 59

2-propanyl 3-{(2R,5aR,6R,7R,8aS)-7-hydroxy-6-[(1E,3R)-3-hydroxy-4-phenoxy-1-buten-1-yl]octahydro-2H-cyclopenta[b]oxepin-2-yl}propanoate

[Chemical formula 55]

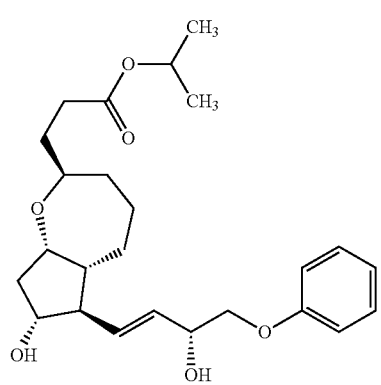

The compound produced in Example 58 was subjected to the same objective operations as those of Example 13→Example 14→Example 15→Example 16 (1) to obtain a titled compound having the following physical property values.

TLC: Rf 0.32 (hexane:ethyl acetate=1:3);
$^1$H-NMR (300 MHz, CDCl$_3$): δ 7.27-7.31, 6.89-6.99, 5.59-5.72, 4.93-5.05, 4.49-4.55, 4.21, 3.99, 3.88, 3.69-3.83, 2.55, 2.19-2.44, 1.45-1.88, 1.23.

Example 60

[(2S,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]methanol Using the compound produced in Example 53 (2), this compound was subjected to the same objective operations as those of Example 54→Example 55 to obtain a titled compound having the following physical property values.

TLC: Rf 0.58 (hexane:ethyl acetate=50:50).

Example 61

2-Propanyl 3-{(2S,5aR,6R,7R,8aS)-7-hydroxy-6-[(1E,3R)-3-hydroxy-4-phenoxy-1-buten-1-yl]octahydro-2H-cyclopenta[b]oxepin-2-yl}propanoate

[Chemical formula 56]

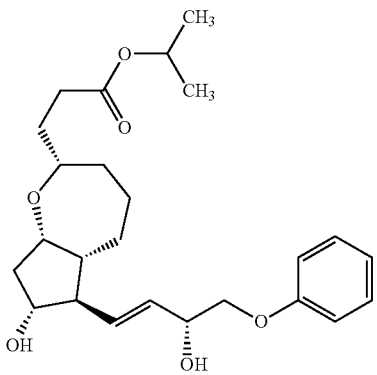

Using the compound produced in Example 60, this compound was subjected to the same objective operations as those of Example 56→Example 57→Example 58→Example 59 to obtain a titled compound having the following physical property values.

TLC: Rf 0.34 (hexane:ethyl acetate=1:3);
$^1$H-NMR (300 MHz, CDCl$_3$): δ 7.27-7.32, 6.90-7.00, 5.59-5.72, 4.94-5.06, 4.49-4.55, 3.93-4.01, 3.88, 3.69-3.79, 3.17-3.25, 2.52, 2.27-2.46, 2.06-2.19, 1.65-1.84, 1.26-1.49, 1.23.

Example 62

[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]methylmethanesulfonate Under the argon atmosphere, the compound (207 mg) produced in Example 55 was dissolved in dichloromethane (2 mL), and the solution was cooled to 0° C. Triethylamine (0.14 mL) and methanesulfonyl chloride (0.040 mL) were added, and the mixture was stirred at 0° C. for 15 minutes. To the reaction mixture was added water, and the extract obtained by extraction with ethyl acetate was washed with water and a saturated saline, dried with anhydrous magnesium sulfate, and concentrated under reduced pressure to obtain a titled compound (273 mg) having the following physical property values.

TLC: Rf 0.40 (hexane:ethyl acetate=67:33).

Example 63

[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]acetonitrile The compound (273 mg) produced in Example 62 was dissolved in DMSO (1 mL), sodium cyanide (55 mg) was added, and the mixture was stirred at 80° C. overnight. To the reaction mixture was added water, and the extract obtained by extraction with ethyl acetate was washed with water and a saturated saline, dried with anhydrous magnesium sulfate, and concentrated under reduced pressure. The residue was purified by silica gel column chromatography (hexane:ethyl acetate=90:10→70:30) to obtain a titled compound (205 mg) having the following physical property values.

TLC: Rf 0.55 (hexane:ethyl acetate=75:25).

Example 64

2-propanyl(2E)-3-[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]acrylate The compound (195 mg) produced in Example 63 was dissolved in toluene (4 mL), and the solution was cooled to −15° C. A 1M toluene solution (0.8 mL) of diisobutylaluminum hydride was added, and the mixture was stirred at the same temperature for 1 hour and 30 minutes. To the reaction mixture was added an aqueous saturated ammonium chloride solution, and the extract obtained by extraction with ethyl acetate was washed with 1N hydrochloric acid, an aqueous saturated sodium bicarbonate solution, water and a saturated saline, dried with anhydrous magnesium sulfate, and concentrated under reduced pressure. The residue was dissolved in dichloromethane (2 mL), phosphorane (250 mg) was added, and the mixture was stirred at room temperature overnight. After the reaction mixture was concentrated under reduced pressure, the residue was purified by silica gel column chromatography (hexane:ethyl acetate=95:5→75:25) to obtain a titled compound (39 mg) having the following physical property values.

TLC: Rf 0.46 (hexane:ethyl acetate=80:20).

Example 65

2-propanyl 4-{(2R,5aR,6R,7R,8aS)-7-hydroxy-6-[(1E,3R)-3-hydroxy-4-phenoxy-1-buten-1-yl]octahydro-2H-cyclopenta[b]oxepin-2-yl}butanoate

[Chemical formula 57]

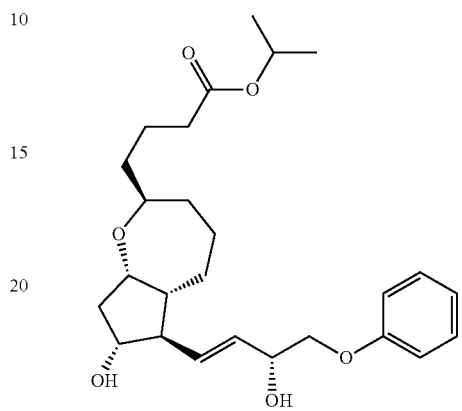

Using the compound produced in Example 64, this compound was subjected to the same objective operations as those of Example 56→Example 57→Example 58→Example 59 to obtain a titled compound having the following physical property values.

TLC: Rf 0.36 (hexane:ethyl acetate=1:3);
$^1$H-NMR (300 MHz, CDCl$_3$): δ 7.26-7.31, 6.89-6.99, 5.60-5.72, 4.93-5.06, 4.50-4.55, 4.17-4.24, 3.99, 3.88, 3.70-3.82, 2.56-2.61, 2.21-2.34, 1.51-1.78, 1.26-1.37, 1.23.

Example 66

2-propanyl 4-{(2S,5aR,6R,7R,8aS)-7-hydroxy-6-[(1E,3R)-3-hydroxy-4-phenoxy-1-buten-1-yl]octahydro-2H-cyclopenta[b]oxepin-2-yl}butanoate

[Chemical formula 58]

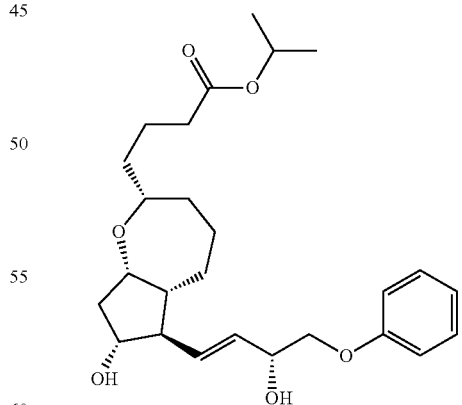

Using the compound produced in Example 60, this compound was subjected to the same objective operations as those of Example 62→Example 63→Example 64→Example 56→Example 57→Example 58→Example 59 to obtain a titled compound having the following physical property values.

TLC: Rf 0.42 (hexane:ethyl acetate=1:3);
$^1$H-NMR (300 MHz, CDCl$_3$): δ 7.26-7.31, 6.89-6.99, 5.58-5.72, 4.93-5.05, 4.48-4.55, 3.97-4.03, 3.87, 3.69-3.77, 3.13-3.22, 2.52-2.59, 2.38-2.47, 2.23-2.29, 2.11-2.19, 1.28-1.84, 1.22.

Example 67 (1) to Example 67 (4)

Using the compounds produced in Example 59, Example 61, Example 65 and Example 66, these compounds were subjected to the same objective operations as those of Example 17 (1) to obtain the following Example compounds.

Example 67 (1)

3-{(2R,5aR,6R,7R,8aS)-7-hydroxy-6[(1E,3R)-3-hydroxy-4-phenoxy-1-buten-1-yl]octahydro-2H-cyclopenta[b]oxepin-2-yl}propanoic acid

[Chemical formula 59]

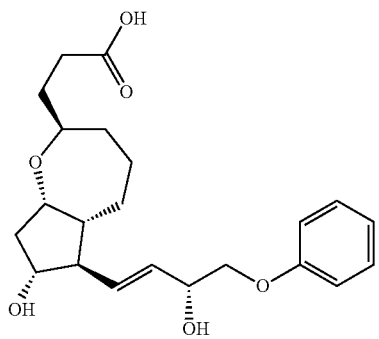

TLC: Rf 0.36 (chloroform:methanol=5:1);
$^1$H-NMR (300 MHz, CDCl$_3$): δ 7.24-7.30, 6.89-6.98, 5.54-5.70, 4.48, 4.19, 3.95, 3.69-3.85, 2.19-2.54, 1.47-1.93.

Example 67 (2)

3-{(2S,5aR,6R,7R,8aS)-7-hydroxy-6-[(1E,3R)-3-hydroxy-4-phenoxy-1-buten-1-yl]octahycro-2H-cyclopenta[b]oxepin-2-yl}propanoic acid TLC: Rf 0.39 (chloroform:methanol=5:1);
$^1$H-NMR (300 MHz, CDCl$_3$): δ 7.24-7.30, 6.88-6.98, 5.56-5.67, 4.45-4.52, 3.86-4.02, 3.67-3.76, 3.20-3.29, 2.33-2.52, 2.09-2.18, 1.63-1.86, 1.22-1.48.

Example 67 (3)

4-{(2R,5aR,6R,7R,8aS)-7-hydroxy-6-[(1E,3R)-3-hydroxy-4-phenoxy-1-buten-1-yl]octahydro-2H-cyclopenta[b]oxepin-2-yl}butanoic acid TLC: Rf 0.37 (chloroform:methanol=5:1);
$^1$H-NMR (300 MHz, CD$_3$OD): δ 7.21-7.26, 6.87-6.93, 5.56-5.69, 4.38-4.44, 4.21-4.29, 3.84-4.00, 3.65-3.77, 2.27-2.36, 2.07-2.17, 1.50-1.84, 1.28-1.40.

Example 67 (4)

4-{(2S,5aR,6R,7R,8aS)-7-hydroxy-6-[(1E,3R)-3-hydroxy-4-phenoxy-1-buten-1-yl]octahydro-2H-cyclopenta[b]oxepin-2-yl}butanoic acid TLC: Rf 0.42 (chloroform:methanol=5:1);
$^1$H-NMR (300 MHz, CDCl$_3$): δ 7.25-7.30, 6.88-6.98, 5.56-5.69, 4.46-4.53, 3.86-4.02, 3.67-3.75, 3.14-3.23, 2.40-2.49, 2.35, 2.09-2.18, 1.24-1.84.

Example 68

4-{(3S,5aR,6R,7R,8aS)-6-[(1E)-4-(3-chlorophenoxy)-3-oxo-1-buten-1-yl]-7-hydroxyoctahydro-2H-cyclopenta[b]oxepin-3-yl}butanoic acid

[Chemical formula 60]

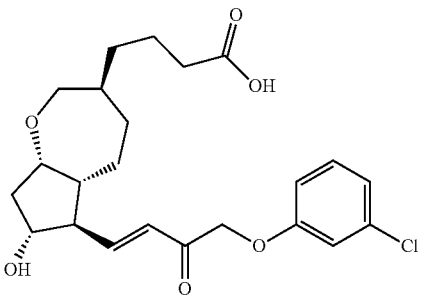

The compound (102 mg) produced in Example 17 (3) was dissolved in methylene chloride (2 mL) and acetone (1.5 mL), manganese dioxide (613 mg) was added, and the mixture was stirred at 50° C. for 4 hours. Manganese dioxide was removed with Celite (trade name), followed by washing with chloroform-acetone. After the solvent was concentrated under reduced pressure, the resulting residue was purified with a PLC glass plate (20×20 cm, silica gel 60 F$_{254}$, 0.5 mm, chloroform:methanol=19:1) to obtain a titled compound (7.8 mg) having the following physical property values.
TLC: Rf 0.24 (chloroform:methanol=19:1);
$^1$H-NMR (300 MHz, CD$_3$OD): δ 0.96-1.22, 1.36-1.51, 1.51-1.72, 1.84-2.00, 2.15-2.31, 2.43-2.55, 2.99, 3.81, 3.96-4.10, 4.93, 6.37, 6.81-7.00, 7.19-7.29.

Example 68 (1)

4-{(3S,5aR,6R,7R,8aS)-6-[(1E)-4-(2,5-difluorophenoxy)-3-oxo-1-buten-1-yl]-7-hydroxyoctahydro-2H-cyclopenta[b]oxepin-3-yl}butanoic acid Using the compound produced in Example 17 (25), this compound was subjected to the same objective operations as those of Example 68 to obtain the following Example compound.
TLC: Rf 0.42 (dichloromethane:methanol=10:1);
$^1$H-NMR (CD$_3$OD): δ 0.96-1.25, 1.36-1.75, 1.84-2.03, 2.15-2.33, 2.50, 2.99, 3.81, 3.96-4.11, 5.00, 6.37, 6.67, 6.79, 6.91, 7.11.

Example 69

(5aR,6S,7R,8aS)-6-({[(dimethyl(2-methyl-2-propanyl)silyl]oxy}methyl)-3-[4-oxo-4-(2-propanyloxy)butyl]octahydro-2H-cyclopenta[b]oxepin-7-yl 4-biphenylcarboxylate To a methylene chloride (2.3 mL) solution of the compound (500 mg) produced in Example 10 were added triethylamine (0.246 mL), 4-phenylbenzoyl chloride (303 mg) and dimethylaminopyridine (2 mg) under ice-cooling and the argon atmosphere, and the mixture was stirred at room temperature for 6 hours. Further, triethylamine (0.123 mL) and 4-phenylbenzoyl chloride (151 mg) were added, and the mixture was stirred at room temperature overnight. After completion of the reaction, the reaction mixture was diluted with ethyl acetate, water was added, and this was extracted with ethyl acetate. The organic layer was washed with an aqueous saturated sodium bicarbonate solution, water and a saturated saline. After drying with anhydrous sodium sulfate, the solvent was distilled off under reduced pressure, the precipitated crystal was removed with MTBE, and the filtrate was concentrated under reduced pressure. The resulting residue was purified by preparative chromatograph (Hiflash-SI, size L, hexane:ethyl acetate=100:0→9:1-4:1→3:2) manufactured by Yamazen Corporation to obtain a titled compound (641 mg) having the following physical property values.

TLC: Rf 0.64 (hexane:ethyl acetate=3:1).

Example 70

(3S,5aR,6S,7R,8aS)-6-(hydroxymethyl)-3-[4-oxo-4-(2-propanyloxy)butyl]octahydro-2H-cyclopenta[b]oxepin-7-yl 4-biphenylcarboxylate To a THF (0.5 mL) solution of the compound (640 mg) produced in Example 69 was added a 1M THF solution (2.1 mL) of tetrabutylammonium fluoride at room temperature, and the mixture was stirred for 2 hours. After completion of the reaction, the reaction mixture was diluted with ethyl acetate, and the reaction was stopped with an ice-cooled aqueous saturated ammonium chloride solution. This was extracted with ethyl acetate, the organic layer was washed with water and a saturated saline, and dried with anhydrous sodium sulfate, and the solvent was concentrated under reduced pressure. The resulting residue was purified by preparative chromatograph (Hiflash-SI, Size L, hexane:ethyl acetate=85:15→7:3→1:1→3:7) manufactured by Yamazen Corporation to obtain a titled compound (214 mg) having the following physical property values.

TLC: Rf 0.30 (hexane:ethyl acetate=2:1).

Example 71

(3S,5aR,6R,7R,8aS)-6-[(1E,3R)-4-(2,5-difluorophenoxy)-3-(tetrahydro-2H-pyran-2-yloxy)-1-buten-1-yl]-3-[4-oxo-4-(2-propanyloxy)butyl]octahydro-2H-cyclopenta[b]oxepin-7-yl 4-biphenylcarboxylate Using the compound produced in Example 70, this compound was subjected to the same objective operations as those of Example 13→Example 14→Example 15→Example 11 to obtain a titled compound having the following physical property values.

TLC: Rf 0.58 (hexane:ethyl acetate=2:1).

Example 72

2-propanyl 4-{(3S,5aR,6R,7R,8aS)-6-[(1E,3R)-4-(2,5-difluorophenoxy)-3-(tetrahydro-2H-pyran-2-yloxy)-1-buten-1-yl]-7-hydroxyoctahydro-2H-cyclopenta[b]oxepin-3-yl}butanoate To a 2-propanol (5 mL) solution of the compound (950 mg) produced in Example 71 was added lithium isopropoxide (2.0M THF solution, 2.3 mL), and the reaction mixture was stirred at 50° C. for 5 hours. The reaction mixture was cooled to 0° C., and poured into a water-ethyl acetate mixed solution which had been similarly cooled to 0° C., and the organic layer was washed with water and a saturated saline, dried with magnesium sulfate, and concentrated under reduced pressure. The resulting residue was purified by silica gel column chromatography (hexane:ethyl acetate=1:1→only ethyl acetate) to obtain a titled compound (530 mg) having the following physical property values.

TLC: Rf 0.26 (hexane:ethyl acetate=1:1).

Example 73

2-propanyl 4-[(3S,5aR,6R,7S,8aS)-6-[(1E,3R)-4-(2,5-difluorophenoxy)-3-(tetrahydro-2H-pyran-2-yloxy)-1-buten-1-yl]-7-(formyloxy)octahydro-2H-cyclopenta[b]oxepin-3-yl]butanoate To a THF (0.3 mL) solution of the compound (29 mg) produced in Example 72 were added triphenylphosphine (27 mg), formic acid (4 µL) and a toluene solution of diethyl azodicarboxylate (47 µL, 2.2 mol/L) at −15° C., and the reaction mixture was stirred at 0° C. for 1.5 hours. Further, triphenylphosphine (27 mg), formic acid (4 µL) and a toluene solution of diethyl azodicarboxylate (47 µL, 2.2 mol/L) were added at 0° C., and the reaction mixture was stirred at room temperature for 2 hours. To the reaction mixture was added an aqueous saturated baking soda solution, and this was extracted with ethyl acetate. The organic layer was washed with water and an aqueous saturated sodium chloride solution, dried with anhydrous sodium sulfate, and concentrated under reduced pressure, and the residue was purified by silica gel column chromatography (hexane:ethyl acetate=8:2→5:5) to obtain a titled compound (10 mg) having the following physical property values.

TLC: Rf 0.32 (hexane:ethyl acetate=2:3).

Example 74

2-propanyl 4-[(3S,5aR,6R,7S,8aS)-6-[(1E,3R)-4-(2,5-difluorophenoxy)-3-(tetrahydro-2H-pyran-2-yloxy)-1-buten-1-yl]-7-hydroxyoctahydro-2H-cyclopenta[b]oxepin-3-yl]butanoate To a 2-propanol (0.35 mL) solution of the compound (10 mg) produced in Example 73 was added potassium carbonate (3 mg) at 0° C., and the reaction mixture was stirred at 40° C. for 1 hour. To the reaction mixture was added an aqueous saturated ammonium chloride solution, and this was extracted with ethyl acetate. The organic layer was washed with a saturated saline, dried with anhydrous magnesium sulfate, and concentrated under reduced pressure to obtain a titled compound (8 mg) having the following physical property values.

TLC: Rf 0.39 (hexane:ethyl acetate=1:1).

Example 75

2-propanyl 4-{(3S,5aR,6R,7S,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate Using the compound produced in Example 74, this compound was subjected to the same objective operations as those of Example 16 (1) to obtain a titled compound having the following physical property values.

TLC: Rf 0.47 (hexane:ethyl acetate=1:4);
$^1$H-NMR (300 MHz, CDCl$_3$): δ 7.00, 6.71, 6.60, 5.90, 5.63, 4.99, 4.56, 4.28, 4.18, 4.08-3.88, 2.97, 2.78, 2.15-2.00, 1.95-0.95.

Example 76

4-{(3S,5aR,6R,7S,8aS)-6-[(1E,3R)-4-(2,5-difluorophenoxy)-3-hydroxy-buten-1-yl]-7-hydroxyoctahydro-2H-cyclopenta[b]oxepin-3-yl}butanoic acid Using the compound produced in Example 75, this compound was subjected to the same objective operations as those of Example 17 (1) to obtain a titled compound having the following physical property values.

TLC: Rf 0.28 (dichloromethane:methanol=9:1);
$^1$H-NMR (300 MHz, CDCl$_3$): δ 7.08-6.90, 6.78-6.52, 5.90, 5.63, 4.57, 4.29, 4.22-3.85, 2.97, 2.40-2.20, 2.13, 1.98-1.80, 1.80-1.50, 1.45-0.95.

Example 77

(1R,2R,3S,4R)-2-allyl-3-({[dimethyl(2-methyl-2-propanyl)silyl]oxy}methyl)-4-(tetrahydro-2H-pyran-2-yloxy)cyclopentanol Using the compound produced in Example 3, this compound was subjected to the same objective operations as those of Example 73 to obtain a titled compound having the following physical properties.

TLC: Rf 0.59 (hexane:ethyl acetate=2:1).

Example 78

2-propanyl 4-[(5aR,6S,7R,8aR)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-yl]butanoate Using the compound produced in Example 77, this compound was subjected to the same objective operations as those of Example 4→Example 5→Example 6→Example 7→Example 8 to obtain a titled compound having the following physical property values.

TLC: Rf 0.39 (hexane:ethyl acetate=4:1).

Example 79

2-propanyl 4-{(5aR,6R,7R,8aR)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}butanoate Using the compound produced in Example 78, this compound was subjected to the same objective operations as those of Example 12→Example 13→Example 14→Example 15→Example 16 (1) to obtain a titled compound having the following physical property values.

TLC: Rf 0.52 (ethyl acetate);
$^1$H-NMR (300 MHz, CDCl$_3$): δ 1.19-1.33, 1.43-1.58, 1.65-1.79, 1.86-2.16, 2.16-2.34, 2.59, 3.77, 3.92, 3.97-4.19, 4.51-4.62, 5.01, 5.58-5.82, 6.89-7.04, 7.25-7.36.

Example 80

4-{(5aR,6R,7R,8aR)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}butanoic acid Using the compound produced in Example 79, this compound was subjected to the same objective operations as those of Example 17 (1) to obtain a titled compound having the following physical property values.

TLC: Rf 0.64 (dichloromethane:methanol=7:1);
$^1$H-NMR (300 MHz, CD$_3$OD): δ 1.25-1.49, 1.57-1.76, 1.87-2.12, 2.18-2.34, 3.77, 3.89-4.19, 4.44, 5.57-5.77, 6.84-7.01, 7.21-7.33.

Example 81

2-propanyl 4-{(5aR,6R,7R,8aR)-7-hydroxy-6-[(1E,3R)-3-hydroxy-4-phenoxy-1-buten-1-yl]octahydro-2H-cyclopenta[b]oxepin-3-yl}butanoate Using the compound produced in Example 78, this compound was subjected to the same objective operations as those of Example 9→Example 10→Example 11→Example 12→Example 13→Example 14→Example 15→Example 16 (1) to obtain a titled compound having the following physical property values.

TLC: Rf 0.46 (ethyl acetate);
$^1$H-NMR (300 MHz, CDCl$_3$): δ 0.97-2.14, 2.18-2.34, 2.53-2.63, 3.23, 3.44, 3.71-4.18, 4.49-4.61, 4.93-5.09, 5.58-5.82, 6.88-7.04, 7.24-7.36.

Example 81 (1)

2-propanyl 4-{(5aR,6R,7R,8aR)-6-[(1E,3R)-4-(2,5-difluorophenoxy)-3-hydroxy-1-buten-1-yl]-7-hydroxyoctahydro-2H-cyclopenta[b]oxepin-3-yl}butanoate Using the compound produced in Example 78, and using dimethyl-(3-phenoxy-2-oxopropyl)-phosphonate or a corresponding phosphonic acid salt in place of it, these substances were subjected to the same objective operations as those of Example 81 to obtain a titled compound having the following physical properties.

TLC: Rf 0.52 (ethyl acetate);
$^1$H-NMR (300 MHz, CDCl$_3$): δ 1.00-1.91, 1.91-2.13, 2.22-2.33, 2.59-2.68, 3.23, 3.44, 3.73-4.19, 4.52-4.63, 4.95-5.07, 5.56-5.83, 6.57-6.68, 6.68-6.78, 6.97-7.10.

Example 82 to Example 82 (1)

Using the compounds produced in Example 81 or Example 81 (1), this compound was subjected to the same objective operations as those of Example 17 (1) to obtain the following Example compounds.

Example 82

4-{(5aR,6R,7R,8aR)-7-hydroxy-6-[(1E,3R)-3-hydroxy-4-phenoxy-1-buten-1-yl]octahydro-2H-cyclopenta[b]oxepin-3-yl}butanoic acid TLC: Rf 0.53 (dichloromethane:methanol=7:1);
$^1$H-NMR (300 MHz, CD$_3$OD): δ 0.99-2.04, 2.21-2.33, 3.20-3.46, 3.73-4.03, 4.43, 5.56-5.77, 6.86-5.77, 6.86-6.95, 7.20-7.30.

Example 82 (1)

4-{(5aR,6R,7R,8aR)-6-[(1E,3R)-4-(2,5-difluorophenoxy)-3-hydroxy-1-buten-1-yl]-7-hydroxyoctahydro-2H-cyclopenta[b]oxepin-3-yl}butanoic acid TLC: Rf 0.47 (dichloromethane:methanol=7:1);
$^1$H-NMR (300 MHz, CD$_3$OD): δ 1.00-2.06, 2.22-2.33, 3.20-3.47, 3.74-3.86, 3.88-4.02, 4.45, 5.54-5.79, 6.57-6.68, 6.68-6.96, 7.01-7.13.

Example 83

4-[(3S,5aR,6R,7R,8aS)-6-(3,3-difluoro-4-phenoxybutyl)-7-hydroxyoctahydro-2H-cyclopenta[b]oxepin-3-yl]butanoic acid Using the compound produced in Example 30, this compound was subjected to the same objective operations as those of Example 18→Example 19 to obtain a titled compound having the following physical property values.
TLC: Rf 0.51 (ethyl acetate);
$^1$H-NMR (300 MHz, CDCl$_3$): δ 7.35-7.29, 7.02, 6.95-6.91, 4.13, 4.04, 3.97, 3.74, 2.93, 2.34, 2.28-2.03, 1.95-1.51, 1.22-1.00.

Example 84

[(3S,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl] methyl methanesulfonate To a methylene chloride (300 mL) solution of the compound (40.7 g) produced in Example 23 were sequentially added triethylamine (27.36 mL) and mesyl chloride (7.98 mL) under ice-cooling, and the mixture was stirred for 1 hour. The reaction solution was poured into ice-water (300 mL), and this was extracted with ethyl acetate. The extract was washed with water (100 mL) and a saturated saline (100 mL), and dried with anhydrous sodium sulfate. Concentration of the solvent under reduced pressure afforded a titled compound (50.2 g) having the following physical property values.
TLC: Rf 0.71, 0.63 (methylene chloride:ethyl acetate=2:1).

Example 85

[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl] acetonitrile To a DMSO (250 mL) solution of the compound (50.2 g) produced in Example 84 was added sodium cyanide (8.18 g) at room temperature, and the mixture was stirred at 70° C. overnight. The reaction solution was poured into ice water (750 mL), and this was extracted with ethyl acetate. The organic layer was washed with water (200 mL) and a saturated saline (200 mL), and dried with anhydrous sodium sulfate. The solvent was concentrated under reduced pressure, and the resulting residue was purified by preparative chromatograph (Hiflash-SI, Size 5 L×2, hexane:ethyl acetate=manufactured by Yamazen Corporation to obtain a titled compound (36.4 g) having the following physical property values.
TLC: Rf 0.42 (hexane:ethyl acetate=2:1).

Example 86

[(3R,5aR,6S,7R,8aS)-6-({[dimethyl(2-methyl-2-propany)silyl]oxy}methyl)-7-(tetrahydro-2H-pyran-2-yloxy)octahydro-2H-cyclopenta[b]oxepin-3-yl] acetaldehyde Under the argon atmosphere, a toluene (350 mL) solution of the compound (29.4 g) produced in Example 85 was cooled to −18° C., and a 1M toluene solution (103 mL) of DIBAL was added dropwise over 40 minutes. The reaction solution was diluted with MTBE (300 mL), an aqueous saturated sodium tartrate solution (50 mL) was added under ice-cooling, the mixture was stirred for a while, thereafter, ice-cooled hydrochloric acid (1N, 300 mL) was added, and this was extracted with ethyl acetate. The organic layer was washed with an aqueous saturated ammonium chloride solution, water and a saturated saline, and dried with anhydrous sodium sulfate. Concentration of the solvent under reduced pressure afforded a titled compound (31.3 g) having the following physical property values.
TLC: Rf 0.45 (hexane:ethyl acetate=3:1).

Example 87

2-propanyl(2E)-4-[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]-2-butenoate To a methylene chloride (422 mL) solution of the compound (38.0 g) produced in Example 86 was added isopropyl (triphenylphosphoranylidene) acetate (45.93 g) at room temperature, and the mixture was stirred at room temperature overnight. After completion of the reaction, the solution was concentrated under reduced pressure, and diethyl ether-hexane (1:1, 200 mL) were added. After removal of the analysis product with a glass filter, the filtrate was concentrated under reduced pressure. The resulting residue was purified by preparative chromatograph (Hiflash-SI, Size 5 L×2, hexane:ethyl acetate=100:0→4:1→7:3) manufactured by Yamazen Corporation to obtain a titled compound (36.0 g) having the following physical property values.
TLC: Rf 0.56, 0.49 (hexane:ethyl acetate=4:1).

Example 88

Ethyl(2E)-4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}-2-butenoate Using the compound produced in Example 87, this compound was subjected to the same objective operations as those of Example 12→Example 13→Example 14→Example 15→Example 16 (1) to obtain a titled compound having the following physical property values.
TLC; Rf 0.46 (ethyl acetate);
$^1$H-NMR (300 MHz, CDCl$_3$): δ 0.96-1.12, 1.25-1.33, 1.41-1.54, 1.63-2.18, 2.45-2.54, 2.69, 2.92-2.30, 3.69-3.78, 3.87-4.23, 4.52-4.55, 5.61-5.74, 5.77-5.83, 6.84-7.01, 7.24-7.33.

Example 89

(2E)-4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}-2-butenoic acid Using the compound produced in Example 88, this compound was subjected to the same objective operations as those of Example 17 (1) to obtain a titled compound having the following physical property values.
TLC: Rf 0.31 (dichloromethane:methanol=9:1);
$^1$H-NMR (300 MHz, CDCl$_3$): δ 1.00-1.51, 1.68-2.14, 2.45-2.54, 2.93-3.00, 3.69-3.77, 3.87-4.07, 4.52-4.54, 5.65-5.67, 5.79-5.84, 6.91-7.04, 7.27-7.32.

Example 90

4-{(3S,5aR,6R,7S,8aS)-6-[(1E,3R)-4-(2,5-difluorophenoxy)-3-hydroxy-1-buten-1-yl]-7-fluorooctahydro-2H-cyclopenta[b]oxepin-3-yl}butanoic acid Using the compound (100 mg) produced in Example 72, this compound was subjected to the same objective operations as those of Example 30→Example 31→Example 32 to obtain a titled compound (4 mg) having the following physical property values.

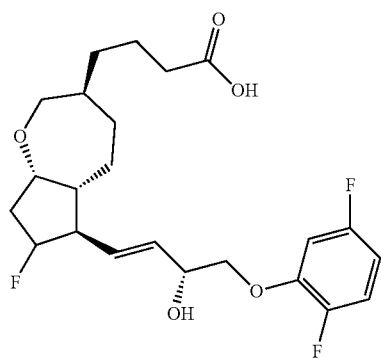

[Chemical formula 61]

TLC: Rf 0.52 (dichloromethane:methanol=9:1);
$^1$H-NMR (300 MHz, CDCl$_3$): δ 0.85-2.62, 2.96-3.04, 3.92-4.09, 4.24-4.31, 4.55-4.61, 4.84-4.86, 5.02-5.04, 5.60-5.67, 5.85-5.93, 6.58-6.66, 6.70-6.76, 6.99-7.08.

Example 91

Ethyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate To a DMF (0.3 mL) solution of the compound (50 mg) produced in Example 17 (25) were added ethyl iodide (21 mg) and potassium carbonate (19 mg), and the reaction mixture was stirred at 50° C. for 30 minutes. The reaction mixture was poured into water, and this was extracted with MTBE. Herein, the aqueous layer was made acidic (pH=4) with 1N hydrochloric acid, and extracted with ethyl acetate, and the organic layer was washed with water and a saturated saline, dried with magnesium sulfate, and concentrated under reduced pressure to recover an unreacted raw material (15 mg). The reaction was tried on the recovered raw material with the aforementioned reagents (ethyl iodide 12 mg, potassium carbonate 6 mg), the mixture was stirred at 50° C. for 1 hour, the reaction mixture was poured into water, and this was extracted with MTBE. The organic layer was washed with water and an aqueous saturated sodium chloride solution, dried with sodium sulfate, and concentrated under reduced pressure, and the resulting residue was purified by silica gel column chromatography (hexane:ethyl acetate=1:1→0:100) to obtain a titled compound (21 mg) having the following physical property values.

TLC: Rf 0.53 (dichloromethane:methanol=9:1);
$^1$H-NMR (300 MHz, CDCl$_3$): δ 0.94-1.30, 1.40-1.95, 2.09-2.31, 2.45-2.54, 2.71-2.73, 2.89-2.97, 3.70-3.79, 3.90-4.17, 4.53-4.60, 5.59-5.74, 6.58-6.66, 6.69-6.76, 6.99-7.08.

Example 91 (1)

3-hydroxypropyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate Using the compound produced in Example 17 (25), and using 3-bromo-1-propanol in place of ethyl iodide, these substances were subjected to the same objective operations as those of Example 91 to obtain a titled compound having the following physical property values.

TLC: Rf 0.38 (dichloromethane: acetone=1:1);
$^1$H-NMR (300 MHz, CDCl$_3$): δ 0.90-1.20, 1.40-1.94, 2.08-2.17, 2.28-2.33, 2.45-2.54, 2.89-2.96, 3.67-3.80, 3.91-4.07, 4.22-4.26, 4.52-4.58, 5.59-5.74, 6.58-6.66, 6.69-6.75, 6.99-7.07.

Example 92

(3S,5aR,6R,7R,8aS)-6-[(1E,3R)-4-(2,5-difluorophenoxy)-3-hydroxy-1-buten-1-yl]-3-(4-hydroxybutyl)octahydro-2H-cyclopenta[b]oxepine-7-ol To a THF (1.4 mL) solution of the compound (25 mg) produced in Example 91 was added lithium aluminum hydride (6 mg) at 0° C., and the reaction mixture was stirred as it was for 1 hour. To the reaction mixture was added an aqueous saturated sodium sulfate solution, and the mixture was filtered with Celite (trade name), and concentrated under reduced pressure. The resulting residue was purified by silica gel column chromatography (ethyl acetate→dichloromethane: methanol=9:1) to obtain a titled compound (22 mg) having the following physical property values:

TLC: Rf 0.24 (ethyl acetate);
$^1$H-NMR (300 MHz, CDCl$_3$): δ 0.95-1.95, 2.01-2.18, 2.45-2.54, 2.62-2.64, 2.89-2.97, 3.62-3.80, 3.90-4.09, 4.54-4.61, 5.60-5.75, 6.58-6.66, 6.69-6.76, 6.99-7.08.

Example 93

4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}-N-ethylbutaneamide To a THF (0.2 mL) solution of the compound (10 mg) produced in Example 17 (25) were added 4-(4,6-dimethoxy-1,3,5-triazin-2-yl)-4-methylmorpholinium chloride (7 mg) and an aqueous ethylamine solution (12M, 19 μL), and the reaction mixture was stirred at room temperature for 6 hours. The reaction mixture was poured into water, this was extracted with ethyl acetate, and the organic layer was washed with 1N hydrochloric acid, an aqueous saturated sodium bicarbonate solution, and a saturated saline, dried with magnesium sulfate, and concentrated under reduced pressure to obtain the residue. The resulting residue was purified by silica gel column chromatography (dichloromethane:methanol=9:1) to obtain a titled compound (10 mg) having the following physical property values.

TLC: Rf 0.44 (dichloromethane:methanol=9:1);
$^1$H-NMR (300 MHz, CD$_3$OD): δ 0.85-1.20, 1.30-1.92, 1.97-2.06, 2.11-2.16, 2.39-2.48, 2.92-3.01, 3.14-3.23, 3.62-3.71, 3.96-4.03, 4.41-4.47, 5.58-5.71, 6.59-6.67, 6.88-6.95, 7.03-7.12, 7.94.

Example 94

3-(3-pyridinyl)propanal

To an ethyl acetate (30 mL) solution of 3-(3-pyridyl)propanol (1.5 g) were added dimethyl sulfoxide (15 mL) and triethylamine (9 mL), a pyridine sulfur trioxide complex (5.2 g) was added while the mixture was stirred at 0° C., and the mixture was stirred as it was for 2 hours. The reaction mixture was concentrated under reduced pressure, and purified by silica gel column chromatography (hexane:ethyl acetate=30: 70→0:100) to obtain a titled compound (1:1 g) having the following physical property values.

TLC: Rf 0.23 (hexane:ethyl acetate=1:2).

Example 95

(3S,5aR,6S,7R,8aS)-6-[(E)-2-iodovinyl]-3-[4-oxo-4-(2-propanyloxy)butyl]octahydro-2H-cyclopenta[b]oxepin-7-yl 4-biphenylcarboxylate To a THF (10 mL) solution of the compound (0.85 g) produced in Example 70 was added chromium chloride (1.7 g), a THF (7 mL) solution of iodoform (1.4 g) was added while the mixture was stirred at 0° C., and the mixture was stirred as it was for 4 hours. The reaction mixture was poured into water, this was extracted with ethyl acetate, and the organic layer was washed with water and a saturated saline, dried with magnesium sulfate, and concentrated under reduced pressure. The resulting residue was purified by silica gel column chromatography (hexane:ethyl acetate=95: 5→75:25) to obtain a titled compound (600 mg) having the following physical property values.

TLC: Rf 0.47 (hexane:ethyl acetate=3:1).

Example 96

(3S,5aR,6R,7R,8aS)-6-[(1E)-3-hydroxy-5-(3-pyridinyl)-1-penten-1-yl]-3-[4-oxo-4-(2-propanyloxy)butyl]octahydro-2H-cyclopenta[b]oxepin-7-yl 4-biphenylcarboxylate To a THF (10 mL) solution of the compound (590 mg) produced in Example 95 and the compound (258 mg) produced in Example 94 were added chromium chloride (470 mg) and nickel chloride (2.5 mg), and the mixture was stirred at room temperature overnight. The reaction mixture was poured into water, and this was extracted with ethyl acetate. An aqueous saturated sodium bicarbonate solution was added to both of the aqueous layer and the organic layer, respectively, both were stirred, and combined, filtered with Celite (trade name), and separated into the aqueous layer and the organic layer again, and the resulting organic layer was dried with magnesium sulfate, and concentrated under reduced pressure. The resulting residue was purified by silica gel column chromatography (hexane:ethyl acetate=30:70→0: 100) to obtain a titled compound (210 mg) having the following physical property values.

TLC: Rf 0.38 (ethyl acetate).

Example 97

2-propanyl 4-{(3S,5aR,6R,7R,8aS)-7-hydroxy-6-[(1E)-3-hydroxy-5-(3-pyridinyl)-1-penten-1-yl]octahydro-2H-cyclopenta[b]oxepin-3-yl}butanoate To a 2-propanol (0.4 mL) solution of the compound (210 mg) produced in Example 96 was added lithium isopropoxide (2.0M THF solution, 0.33 mL), and the reaction mixture was stirred at 50° C. for 4 hours. The reaction mixture was cooled to 0° C., and poured into a water-ethyl acetate mixed solution which had been similarly cooled to 0° C., and the organic layer was washed with water and a saturated saline, dried with magnesium sulfate, and concentrated under reduced pressure. The resulting residue was purified by silica gel column chromatography (dichloromethane:methanol=100:0→90:10) to obtain a titled compound (108 mg) having the following physical property values.

TLC: Rf 0.53 (dichloromethane:methanol=9:1);
$^1$H-NMR (300 MHz, CDCl$_3$): δ 0.93-1.29, 1.39-1.93, 2.04-2.14, 2.22-2.27, 2.42-2.52, 2.63-2.82, 2.88-2.96, 3.65-3.75, 3.92-4.14, 4.94-5.06, 5.42-5.67, 7.20-7.24, 7.52-7.54, 8.44-8.46.

Example 98

4-{(3S,5aR,6R,7R,8aS)-7-hydroxy-6-[(1E)-3-hydroxy-5-(3-pyridinyl)-1-penten-1-yl]octahydro-2H-cyclopenta[b]oxepin-3-yl}butanoic acid Using the compound produced in Example 97, this compound was subjected to the same objective operations as those of Example 17 (1) to obtain a titled compound having the following physical property values.

TLC: Rf 0.64 (dichloromethane:methanol=4:1);
$^1$H-NMR (300 MHz, CD$_3$OD): δ 0.97-2.04, 2.24-2.29, 2.37-2.47, 2.70-2.77, 2.94-3.02, 3.58-3.68, 3.96-4.05, 5.54-5.60, 7.33-7.38, 7.71-7.74, 8.33-8.40.

Example 99

5-[(3-phenoxypropyl)thio]-1-phenyl-1H-tetrazole 3-phenoxypropyl bromide (1.53 g) was dissolved in acetone (9 mL), 1-phenyl-5-mercapto-1H-tetrazole (1.27 g) and potassium carbonate (985 mg) were added, and the mixture was stirred at room temperature for 3 hours. To the reaction solution was added water, and the extract obtained by extraction with ethyl acetate was washed with water and a saturated saline, dried with anhydrous magnesium sulfate, and concentrated under reduced pressure to obtain a titled compound (2.23 g) having the following physical property values.

TLC: Rf 0.62 (hexane:ethyl acetate=67:33).

Example 100

5-[(3-phenoxypropyl)sulfonyl]-1-phenyl-1H-tetrazole

The compound (2.23 g) produced in Example 99 was dissolved in dichloromethane (10 mL), m-chloroperbenzoic acid (4.5 g) was added, and the mixture was stirred at room temperature overnight. To the reaction solution was added a 5% aqueous sodium sulfide solution, and the extract obtained by extraction with ethyl acetate was washed with an aqueous saturated sodium bicarbonate solution, water and a saturated saline. The organic layer was dried with anhydrous magnesium sulfate, and concentrated under reduced pressure. The residue was purified by silica gel column chromatography (hexane:ethyl acetate=85:15→65:35) to obtain a titled compound (1.78 g) having the following physical property values.

TLC: Rf 0.59 (hexane:ethyl acetate=67:33).

Example 101

2-propanyl 4-[(3S,5aR,6R,7R,8aS)-6-[(1E)-4-phenoxy-1-buten-1-yl)-7-(tetrahydro-2H-pyran-2-yloxy)octahydro-2H-cyclopenta[b]oxepin-3-yl]butanoate Under the argon atmosphere, the compound (165 mg) produced in Example 100 was dissolved in DME (2 mL), the solution was cooled to −78° C., and a 0.5M potassium hexamethyldisilazane/toluene solution (0.90 mL) was added. After the mixture was stirred at −78° C. for 20 minutes, a DME (1.5 mL) solution of the compound produced in Example 13 was added dropwise, and the mixture was stirred at the same temperature for 10 minutes. After a temperature of the reaction solution was raised to 0° C., water was added, and the extract obtained by extraction with ethyl acetate was washed with water and a saturated saline, dried with anhydrous magnesium sulfate, and concentrated under reduced pressure. The residue was purified by silica gel column chromatography (hexane:ethyl acetate=90:10→65:35) to obtain a titled compound (177 mg) having the following physical property values.

TLC: Rf 0.58 (hexane:ethyl acetate=67:33).

Example 102

2-propanyl 4-{(3S,5aR,6R,7R,8aS)-7-hydroxy-6-[(1E)-4-phenoxy-1-buten-1-yl]octahydro-2H-cyclopenta[b]oxepin-3-yl}butanoate Using the compound produced in Example 101, this was subjected to the same objective operations as those of Example 16 (1) to obtain a titled compound having the following physical property values.

TLC: Rf 0.52 (hexane:ethyl acetate=33:67);
$^1$H-NMR (300 MHz, CDCl$_3$): δ 7.32-7.25, 6.97-6.88, 5.62, 5.37, 5.01, 4.08-3.93, 3.68, 2.92, 2.57-2.43, 2.25, 2.06, 1.91, 1.82-1.40, 1.24, 1.18-0.93.

Example 103

4-{(3S,5aR,6R,7R,8aS)-7-hydroxy-6-[(1E)-4-phenoxy-buten-1-yl]octahydro-2H-cyclopenta[b]oxepin-3-yl}butanoic acid Using the compound produced in Example 102, this compound was subjected to the same objective operations as those of Example 17 (1) to obtain a titled compound having the following physical property values.

TLC: Rf 0.69 (ethyl acetate:methanol=9:1);
$^1$H-NMR (300 MHz, DMSO-d$_6$): δ 11.98, 7.27, 6.93-6.88, 5.51-5.32, 4.61, 3.99-3.93, 3.90-3.81, 3.47, 2.84, 2.42, 2.26, 2.15, 1.87-1.74, 1.65-1.20, 1.10-0.86.

Example 104

4-(nitrooxy)butylamine nitrate

Fuming nitric acid (1.5 mL) was added dropwise to acetic acid (25 mL) which had been cooled to an inner temperature of −8° C. while an inner temperature of 0° C. or lower was maintained. After the mixed solution was stirred for 10 minutes, 4-amino-1-butanol (3.1 mL) was added dropwise while an inner temperature of 0° C. or lower was maintained. After the mixture was stirred for 10 minutes, a temperature was raised to room temperature with a water bath. After the mixture was stirred for 10 minutes, diethyl ether (100 mL) was added, and this was concentrated under reduced pressure. To the resulting concentrated material was added diethyl ether (100 mL), the mixture was stirred, and the supernatant was removed. The resulting residue was concentrated under reduced pressure to obtain a titled compound (6.31 g) having the following physical property values.

$^1$H-NMR (300 MHz, DMSO-d$_6$): δ 1.44-1.82, 2.68-2.93, 4.53, 7.20-8.15.

Example 105

4-[(4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoyl)amino]butyl nitrate To a DMF solution (1 mL) of the compound (68 mg) produced in Example 104 were added sequentially 1-ethyl-3-(3-dimethylaminopropyl)carbodiimide hydrochloride (87 mg) and triethylamine (95 µL) at room temperature. After the mixture was stirred overnight, the solution was diluted with ethyl acetate, and washed with 1N hydrochloric acid two times, with water once, and with a saturated saline once. This was dried with anhydrous sodium sulfate, and concentrated under reduced pressure. The resulting crude purified product was purified with a column apparatus (Hi-Flash M, ethyl acetate→ethyl acetate:methanol=7:3). Further purification with preparative TLC (toluene:acetone=1:1) and preparative TLC (ethyl acetate:methanol=5:1) afforded a titled compound (7.5 mg) having the following physical property values.

TLC: Rf 0.72 (ethyl acetate:methanol=7:1);
$^1$H-NMR (300 MHz, CDCl$_3$): δ 0.83-1.54, 1.54-1.97, 1.97-2.43, 2.49, 2.71-3.01, 3.30, 3.74, 3.89-4.10, 4.48, 4.52-4.60, 5.42-5.55, 5.58-5.75, 6.62, 6.72, 7.03.

[Process for Producing Crystal of the Present Invention Compound]

In the present invention, each crystal form of the Example compounds can be produced by the methods described in Examples, or methods according to them.

Physical property data of each crystal described in Examples were obtained under the following measurement conditions.

[1] Powder X-Ray Diffraction Spectra
<Measurement Condition>
Apparatus: BRUKER D8 DISCOVER with GADDS manufactured by BRUKER axs
Target: Cu,
Filter: None
Voltage: 40 kV,
Current: 40 mA,
Light exposure: 3 min.
[2] Differential scanning calorimetry (DSC)
<Measuring Condition>
Apparatus: DSC 822e manufactured by METTLER TOLEDO,
Sample amount: 1 to 2 mg,
Sample cell: Aluminum pan 40 µL,
Nitrogen gas flow rate: 40 mL/min,
Temperature raising rate: 0.5, 1, 3, 5 and 10° C./min (25 to 300° C.).

Example A

Crystal of 2-propanyl 4-{(3S,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoate (A-type crystal)

Figure 3:
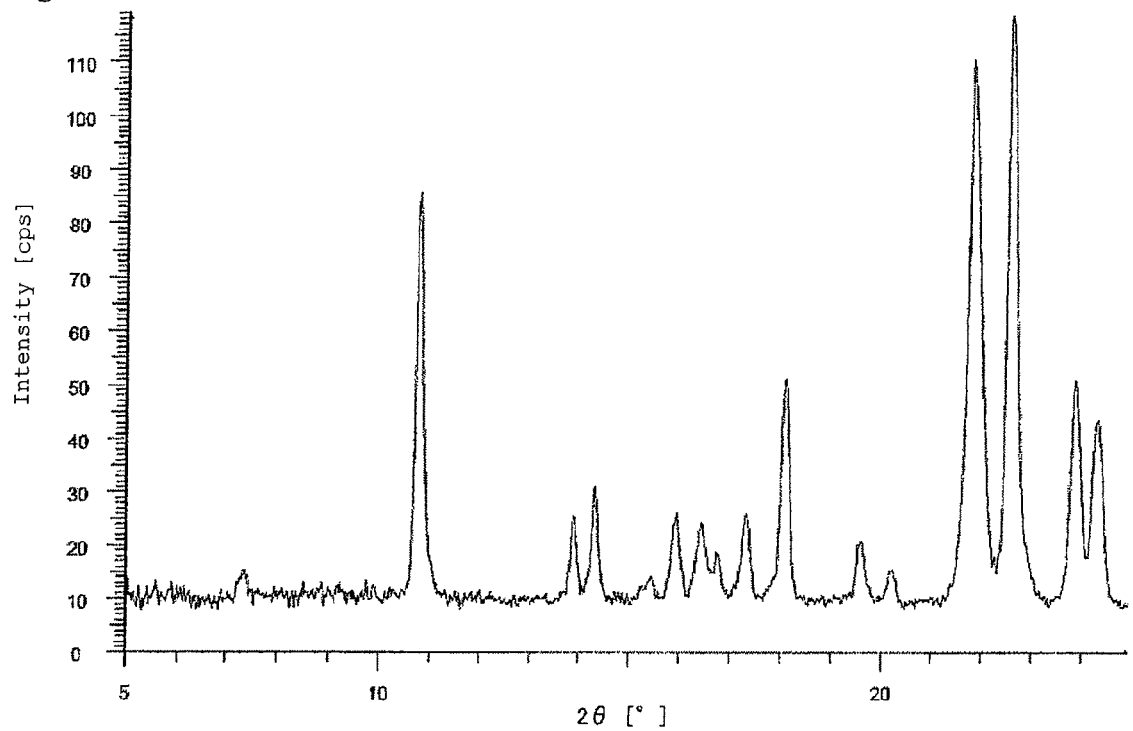
FIG. 3 Shows a powder X-ray diffraction spectral chart of a crystal of the present invention compound (Example A).
Figure 4:
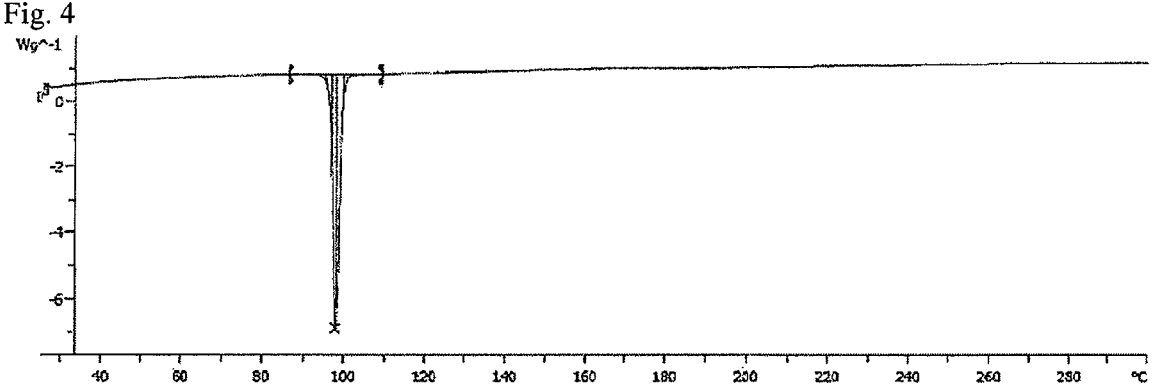
FIG. 4 Shows a differential scanning calorimetry (DSC) of a crystal of the present invention compound (Example A).

To the compound (1.25 g) produced in Example 16 (3) was added 18.75 mL (15 v/w) of a mixed solvent of 2-propanol-heptane (1:7), and this was heated with an oil bath at 70° C. to dissolve the compound. A temperature was lowered to 38° C., and the solution was stirred for about 6.5 hours. After a temperature was returned to room temperature, the solution was stirred for 13.5 hours, and allowed to stand at room temperature for 4.5 hours. The resulting crystal was filtered, washed using 2-propanol-heptane (1:7), and dried under reduced pressure at 50° C. to obtain a titled A-type crystal (1.12 g). Powder X-ray diffraction spectrum of the A-type crystal is shown in FIG. 3, and a differential scanning calorimetry (DSC) chart is shown in FIG. 4, respectively. In addition, a diffraction angle 2θ and a relative intensity in the powder X-ray diffraction spectrum are shown in the following Table.

TABLE 1

| Diffraction angle 2θ (degree) | Relative intensity (%) |
|---|---|
| 7.306 | 12.8 |
| 10.794 | 72 |
| 13.892 | 21.3 |
| 14.325 | 26 |
| 15.431 | 11.8 |
| 15.927 | 21.4 |
| 16.435 | 20.3 |
| 16.743 | 15.7 |
| 17.327 | 21.7 |
| 18.09 | 42.9 |
| 19.59 | 17.3 |
| 20.204 | 12.6 |
| 21.854 | 93 |
| 22.604 | 100 |
| 23.886 | 42.8 |
| 24.341 | 36.5 |

The present crystal showed an endothermic peak corresponding to melting at about 96° C.

Example B

Crystal of 2-propanyl 4-{(3S,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoate (B-type crystal)

Figure 5:
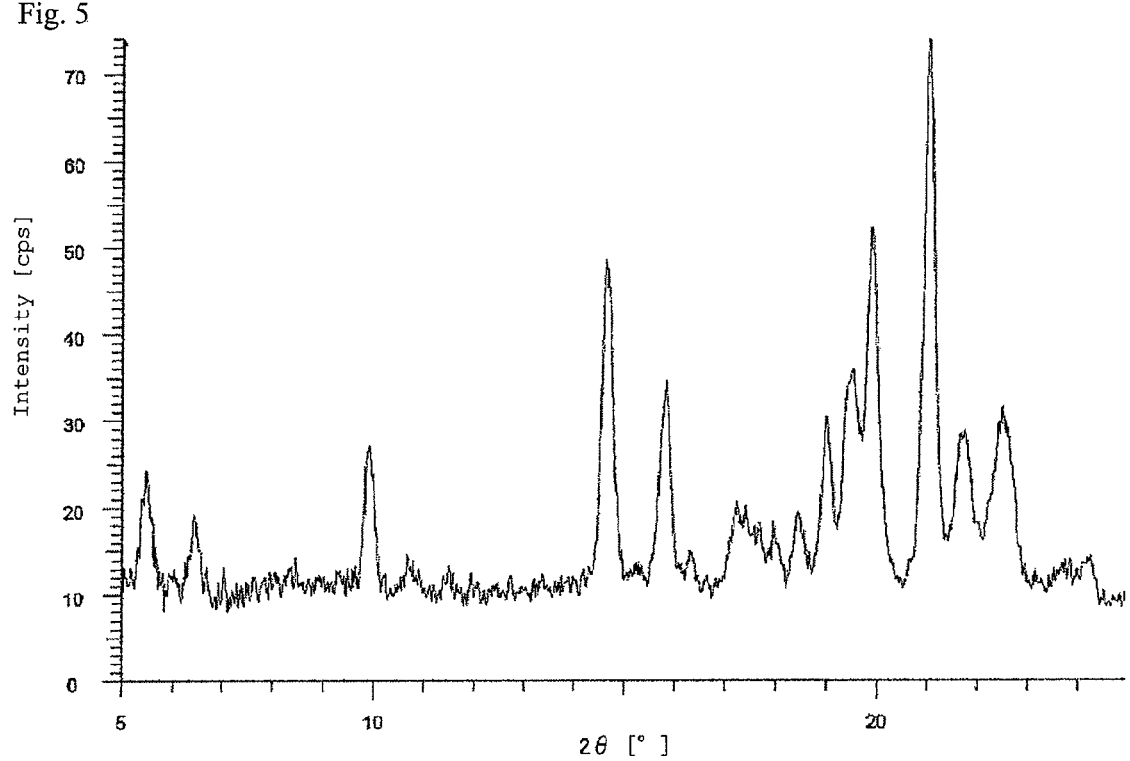
FIG. 5 Shows a powder X-ray diffraction spectral chart of a crystal of the present invention compound (Example B).
Figure 6:
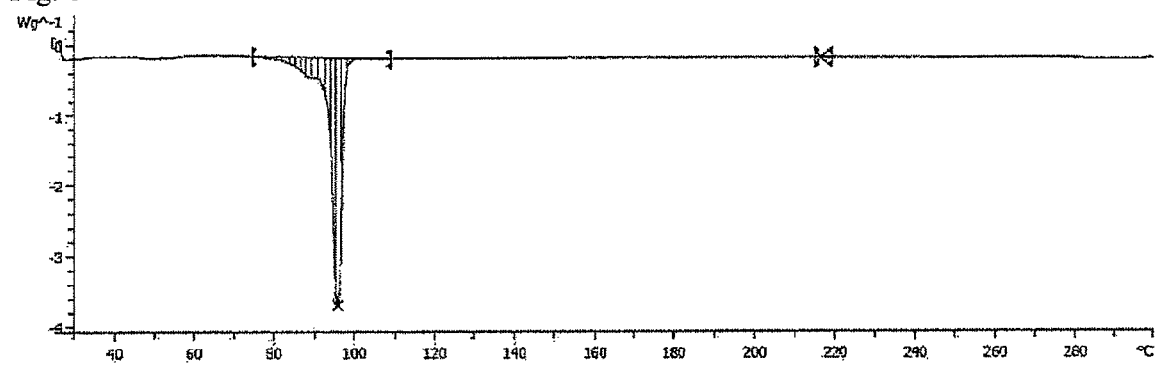
FIG. 6 Shows a differential scanning calorimetry (DSC) chart of a crystal of the present invention compound (Example B).

Solidification by concentration afforded the compound (23.6 mg) produced in Example 16 (3). It was seen that, in the resulting crystal, the A-type crystal produced in Example A and its different crystal (B-type crystal) are present in admixture thereof. The resulting crystal was analyzed, its powder X-ray diffraction spectrum is shown in FIG. 5, and a differential scanning calorimetry (DSC) chart is shown in FIG. 6, respectively. In addition, a diffraction angle 2θ and a relative intensity in the powder X-ray diffraction spectrum are shown in the following Table.
Powder X-Ray Diffraction Spectrum:

TABLE 2

| Diffraction angle 2θ (degree) | Relative intensity (%) |
|---|---|
| 5.453 | 32.7 |
| 6.427 | 25.9 |
| 9.896 | 36.8 |
| 10.69 | 18.1 |
| 11.472 | 17.9 |

TABLE 2-continued

| Diffraction angle 2θ (degree) | Relative intensity (%) |
|---|---|
| 14.645 | 66 |
| 15.81 | 46.8 |
| 16.337 | 19.8 |
| 17.277 | 27 |
| 17.975 | 24.6 |
| 18.45 | 26.4 |
| 19.009 | 41.1 |
| 19.493 | 48.1 |
| 19.906 | 70.8 |
| 21.046 | 100 |
| 21.734 | 38.9 |
| 22.521 | 42.7 |
| 23.765 | 18.8 |
| 24.231 | 19.1 |

The present crystal showed an endothermic peak corresponding to melting at about 93° C.

Example C

Figure 7:
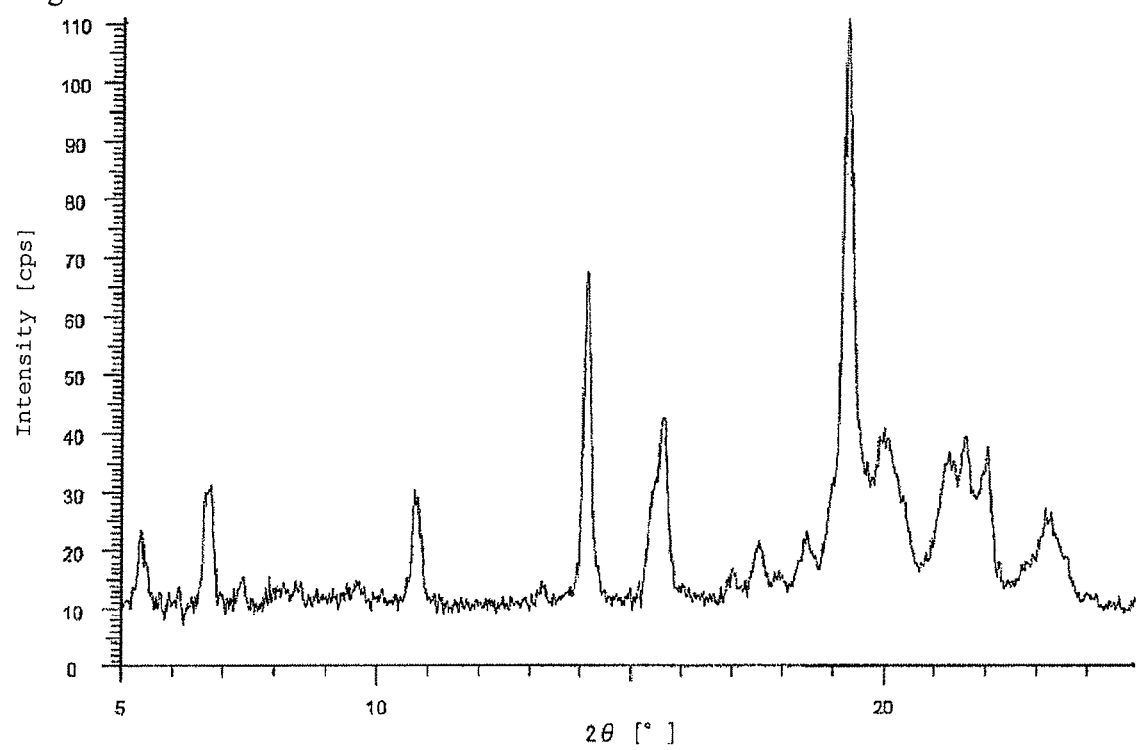
FIG. 7 Shows a powder X-ray diffraction spectral chart of a crystal of the present invention compound (Example C).

Crystal of 2-propanyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate The compound (20.6 mg) produced in Example 16 (1) was dried under reduced pressure at 50° C. for about 1 day to obtain a titled crystal having the following physicochemical data. A power X-ray diffraction spectrum of the present crystal is shown in FIG. 7. In addition, a diffraction angle 2θ and a relative intensity in the powder X-ray diffraction spectrum are shown in the following Table.
Powder X-ray diffraction spectrum:

TABLE 3

| Diffraction angle 2θ (degree) | Relative intensity (%) |
|---|---|
| 5.397 | 21 |
| 6.689 | 27.3 |
| 7.348 | 13.5 |
| 10.772 | 26.2 |
| 13.237 | 13 |
| 14.11 | 61.1 |
| 15.624 | 38.6 |
| 17.002 | 15 |
| 17.541 | 19.3 |
| 18.492 | 20.8 |
| 19.292 | 100 |
| 20.009 | 36.8 |
| 21.285 | 33.2 |
| 21.598 | 35.5 |
| 22.009 | 33.7 |
| 23.222 | 22.4 |

Example D

Crystal of 2-propanyl 4-{(3S,5aR,6R,7R,8aS)-6-[(1E,3R)-4-(2,5-difluorophenxy)-3-hydroxy-1-buten-1-yl]-7-hydroxyoctahydro-2H-cyclopenta[b]oxepin-3-yl}butanoate (A-type crystal)

Figure 8:
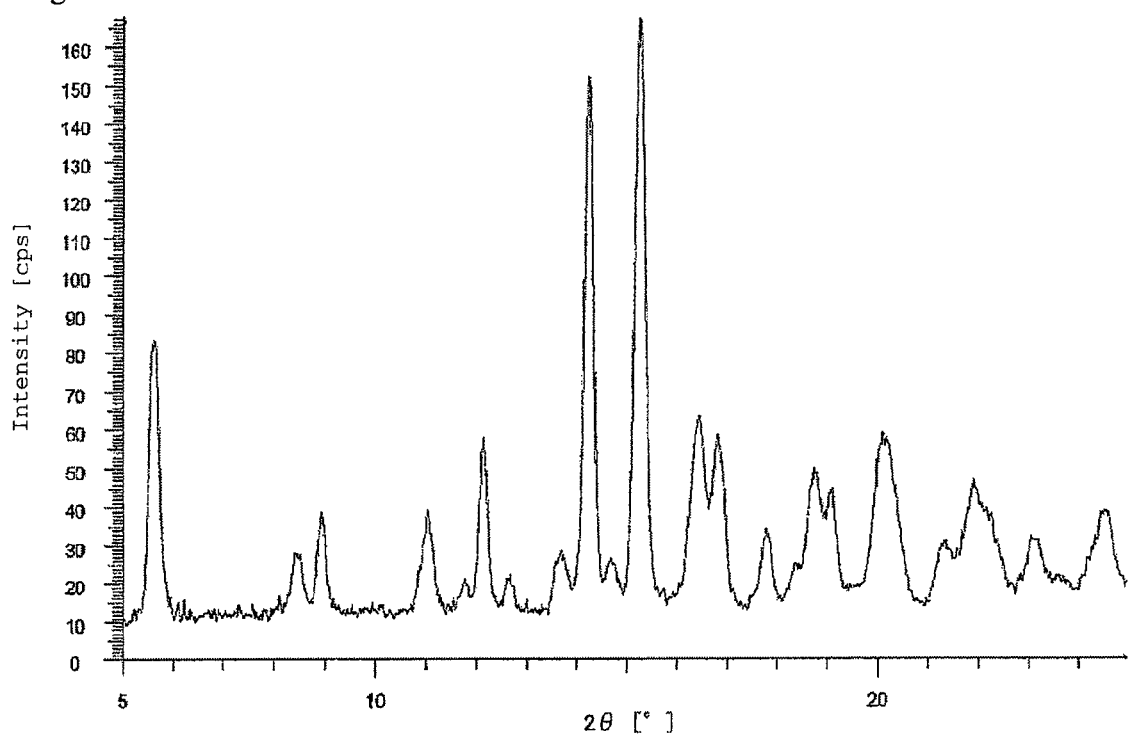
FIG. 8 Shows a powder X-ray diffraction spectral chart of a crystal of the present invention compound (Example D).
Figure 9:
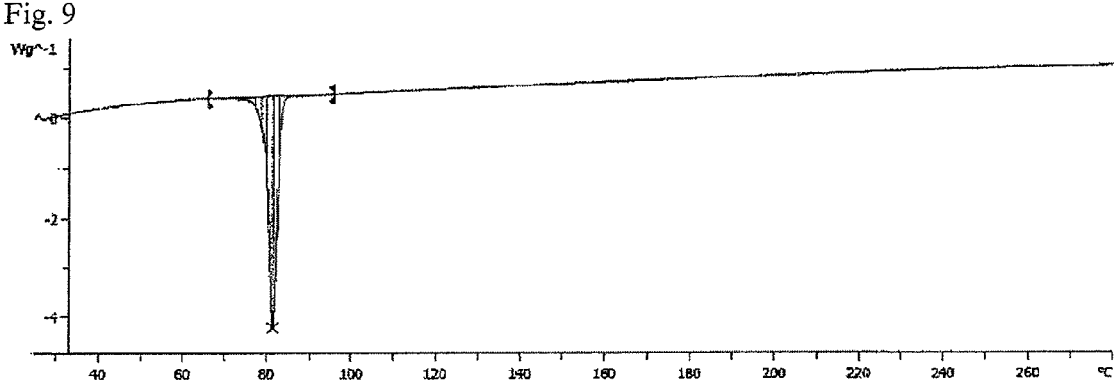
FIG. 9 Shows a differential scanning calorimetry (DSC) chart of a crystal of the present invention compound (Example D).

The compound (1.13 g) produced in Example 16 (25) was placed into an eggplant flask, and 22.6 mL (15 v/w) of a mixed solvent of isopropyl acetate-heptane (1:4) was added. The materials were heated with an oil bath at 60° C. to dissolve the compound. The solution was allowed to cool to 45° C., and stirred for 2 hours. The solution was further allowed to cool to room temperature, and stirred overnight, and the resulting crystal was filtered, and dried under reduced pressure at 50° C. to obtain a titled A-type crystal. A powder X-ray diffraction spectrum of the A-type crystal is shown in FIG. 8, and a differential scanning calorimetry (DSC) chart is shown in FIG. 9, respectively. In addition, a diffraction angle 2θ and a relative intensity in the powder X-ray diffraction spectrum are shown in the following Table.

Powder X-Ray Diffraction Spectrum:

TABLE 4

| Diffraction angle 2θ (degree) | Relative intensity (%) |
|---|---|
| 5.597 | 49.7 |
| 8.421 | 16.6 |
| 8.901 | 23 |
| 11.017 | 23.4 |
| 11.74 | 12.1 |
| 12.127 | 34.8 |
| 12.654 | 13.1 |
| 13.672 | 16.9 |
| 14.22 | 91.1 |
| 14.683 | 16 |
| 15.247 | 100 |
| 16.431 | 38 |
| 16.828 | 35.1 |
| 17.805 | 20.4 |
| 18.767 | 29.7 |
| 19.074 | 26.5 |
| 20.144 | 35.4 |
| 21.344 | 18.6 |
| 21.925 | 28 |
| 23.131 | 18.8 |
| 24.538 | 23.3 |

The present crystal showed an endothermic peak corresponding to melting at about 80° C.

Example E

Crystal of 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate (B-type crystal)

Figure 10:
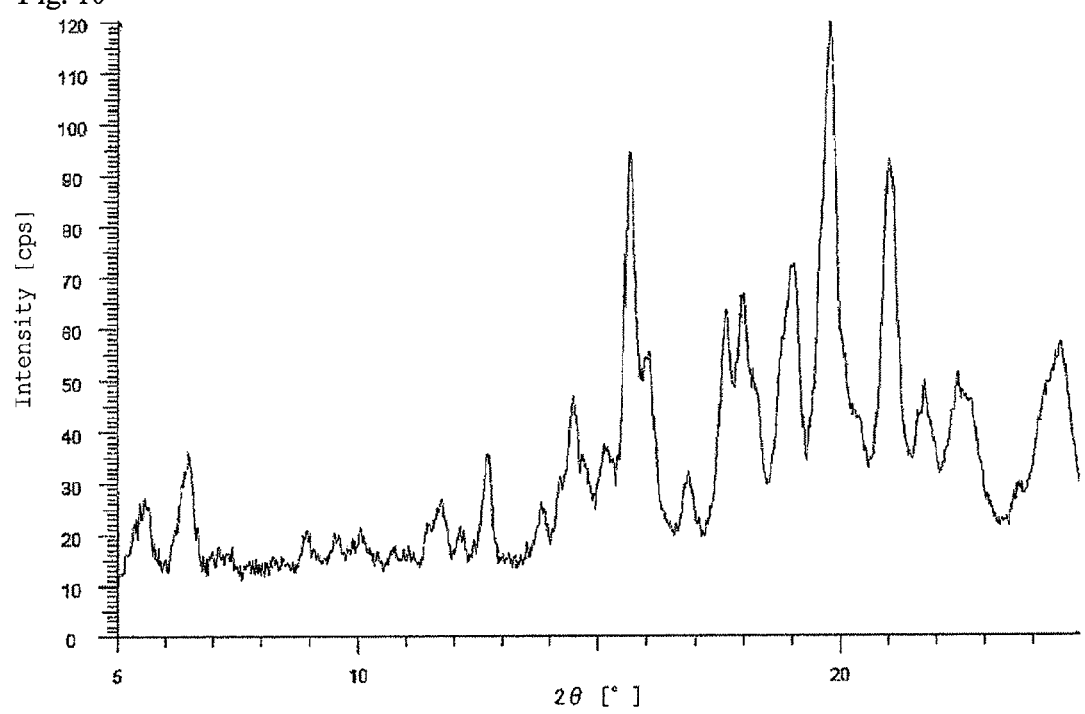
FIG. 10 Shows a powder X-ray diffraction spectral chart of a crystal of the present invention compound (Example E).
Figure 11:
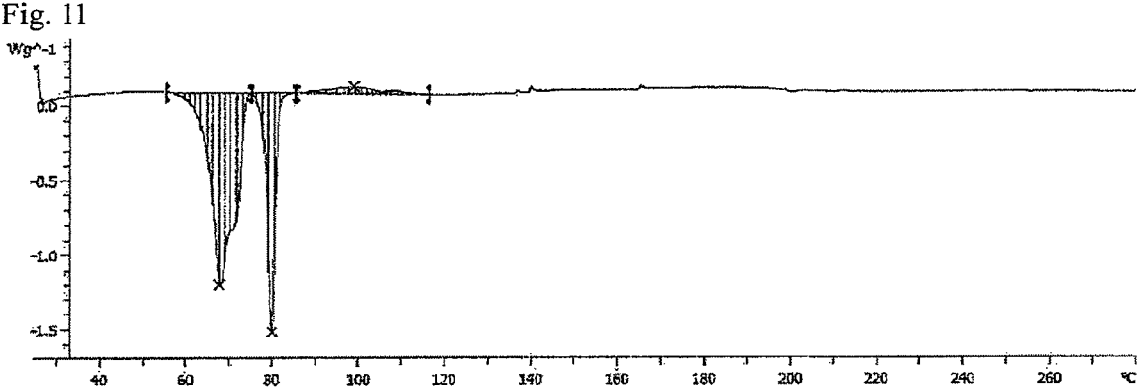
FIG. 11 Shows a differential scanning calorimetry (DSC) chart of a crystal of the present invention compound (Example E).

To the compound (20 mg) produced in Example 16 (25) was added 0.20 mL (10 v/w) of a mixed solvent of isopropyl acetate-heptane (1:4). The materials were heated with an oil bath at 80° C. to dissolve the compound. After allowing to cool from 80° C. to 25° C. at a rate of 3° C./min, the resulting crystal was filtered, and dried under reduced pressure. It was seen that the A-type crystal produced in Example D and its different crystal (B-type crystal) are present in admixture thereof. The resulting crystal was analyzed, its powder X-ray diffraction spectrum is shown in FIG. 10, and a differential scanning calorimetry (DSC) chart is shown in FIG. 11, respectively. In addition, a diffraction angle 2θ and a relative intensity in the powder X-ray diffraction spectrum are shown in the following Table.

Powder X-Ray Diffraction Spectrum:

TABLE 5

| Diffraction angle 2θ (degree) | Relative intensity (%) |
|---|---|
| 5.531 | 22.5 |
| 6.442 | 30.1 |
| 8.927 | 17.1 |

TABLE 5-continued

| Diffraction angle 2θ (degree) | Relative intensity (%) |
|---|---|
| 9.554 | 16 |
| 10.049 | 17.7 |
| 11.708 | 21.5 |
| 12.124 | 17.8 |
| 12.682 | 29.6 |
| 13.822 | 21.7 |
| 14.496 | 38.8 |
| 15.166 | 30.8 |
| 15.651 | 78.8 |
| 16.015 | 46.1 |
| 16.858 | 26.8 |
| 17.638 | 52.8 |
| 17.979 | 55.5 |
| 19.006 | 60.1 |
| 19.786 | 100 |
| 21.034 | 77.6 |
| 21.748 | 41.5 |
| 22.482 | 42.9 |
| 23.744 | 25 |
| 24.571 | 47.7 |

The present crystal showed an endothermic peak corresponding to melting at about 64° C.

Example F

Crystal of 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate (C-type crystal)

Figure 12:
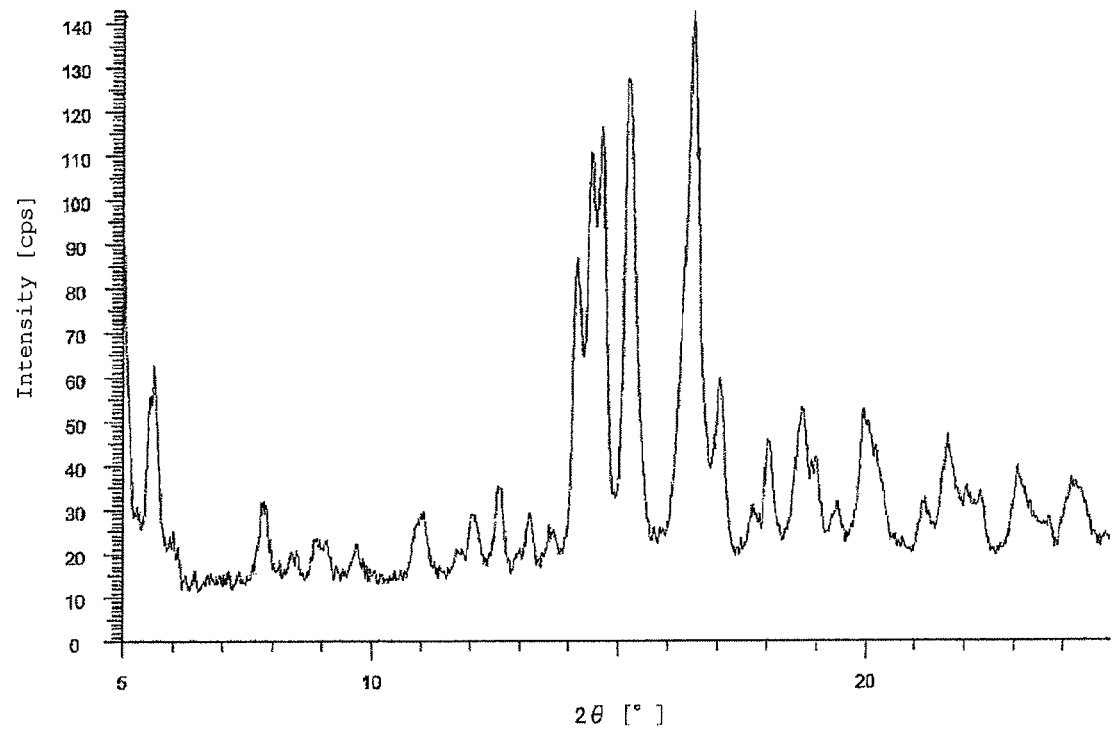
FIG. 12 Shows a powder X-ray diffraction spectral chart of a crystal of the present invention compound (Example F).
Figure 13:
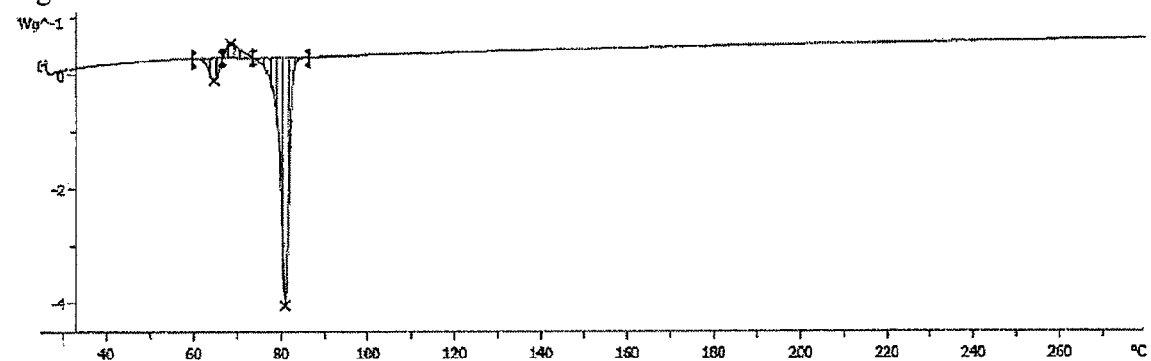
FIG. 13 Shows a differential scanning calorimetry (DSC) chart of a crystal of the present invention compound (Example F).

To the compound (20 mg) produced in Example 16 (25) was added 0.20 mL (10 v/w) of a mixed solvent of isopropyl acetate-heptane (1:4). The materials were heated with an oil bath at 80° C. to dissolve the compound. After allowing to cool from 70° C. to 25° C. at a rate of 3° C./min, the resulting crystal was filtered, and dried under reduced pressure. As a result, it was seen that the A-type crystal produced in Example D and its different crystal (C-type crystal) are present in admixture thereof. The resulting crystal was analyzed, its powder X-ray diffraction spectrum is shown in FIG. 12, and a differential scanning calorimetry (DSC) chart is shown in FIG. 13, respectively. In addition, a diffraction angle 2θ and a relative intensity in the powder X-ray diffraction spectrum are shown in the following Table.

Powder X-Ray Diffraction Spectrum:

TABLE 6

| Diffraction angle 2θ (degree) | Relative intensity (%) |
|---|---|
| 5.588 | 43.7 |
| 7.811 | 22.1 |
| 8.415 | 13.5 |
| 9.038 | 15.8 |
| 9.666 | 15.4 |
| 10.99 | 20.3 |
| 11.76 | 14.3 |
| 12.065 | 20.1 |
| 12.597 | 24.3 |
| 13.206 | 20.3 |
| 13.656 | 17.6 |
| 14.179 | 60.8 |
| 14.482 | 77.6 |
| 14.669 | 81.6 |
| 15.234 | 89.2 |
| 16.531 | 100 |
| 17.068 | 41.7 |
| 17.76 | 21.5 |
| 18.041 | 32 |

TABLE 6-continued

| Diffraction angle 2θ (degree) | Relative intensity (%) |
| --- | --- |
| 18.735 | 37.3 |
| 19.001 | 29.3 |
| 19.413 | 22.1 |
| 20.015 | 35.5 |
| 21.19 | 22.1 |
| 21.685 | 32.9 |
| 22.332 | 23.9 |
| 22.124 | 27.7 |
| 23.708 | 18.8 |
| 24.245 | 25.9 |

The present crystal showed an endothermic peak corresponding to melting at about 60° C.

[Pharmacological Experimental Example]

(1) In Vitro Test (1-1) Measurement of Agonist Activity on Various Mouse Prostanoid Receptors Using CHO cells (FP-CHO, EP1-CHO and IP-CHO, respectively) in which various mouse prostanoid receptors were forcibly expressed, respectively, agonist activity of test compounds on various prostanoid receptors was studied employing an intracellular calcium concentration regarding FP and EP 1, and an intracellular cyclic AMP (hereinafter, abbreviated as cAMP) production amount regarding IP, as an index.

<Compound Treatment>

The test compound and a control substance ($PGE_2$ and iroprost) were dissolved with dimethyl sulfoxide (DMSO) to prepare a 10 mmol/L solution. Regarding the prepared 10 mmol/L solution, upon use, the 10 mmol/L solution was thawed, stepwisely-diluted using DMSO, and diluted with a buffer solution for measurement or a buffer solution for measurement 2, which was subjected to an experiment.

<Cell Culturing>

Cells forcibly expressing various mouse prostanoid receptors were standing-cultured at 37° C. in the presence of 5% $CO_2$ using an α-MEM medium (Sigma) (for culturing FP-CHO and EP1-CHO) containing inactivated (56° C., 30 minutes) 9.8 vol % dialysed-FBS (Invitrogen) and penicillin-streptomycin-glutamine (GIBCO-BRL), or nucleic acid-containing α-MEM (Sigma) (for culturing IP-CHO) containing inactivated (56° C., 30 minutes) 9.8 vol % dialysed-FBS (Invitrogen) and penicillin-streptomycin glutamine (Invitrogen). Subculturing was performed by the following method.

The medium was removed, and washed with a phosphate-buffered physiological saline not containing $Ca^{2+}$ and $Mg^{2+}$ two times. A suitable amount of trypsin-EDTA (Invitrogen) was added, this was incubated at 37° C. for about 3 minutes, cells were peeled, and a medium having a volume which is 10-fold a volume of trypsin-EDTA was added to stop an enzymatic reaction. After cells were recovered (120 g) into a centrifuging tube, and centrifuged at room temperature for 3 minutes, the supernatant was removed. Cells were suspended in a suitable amount of a medium, and seeded in a culturing flask.

(1-2) Measurement of FP and EP1 Agonist Activity (Measurement of Intracellular Calcium Concentration)

Regarding FP-CHO and EP1-CHO, by the same method as that of subculturing, cells were peeled and suspended and, before two days from measurement, the suspension was seeded on a 96-well UV plate so that the cell number per well became $1.0 \times 10^4$, and standing-cultured at 37° C. in the presence of 5% $CO_2$. On the measurement day, after the medium was removed from each well of the 96-well UV plate, each well was washed with a phosphate-buffered physiological saline not containing $Ca^{2+}$ and $Mg^{2+}$ once. To each well was added 100 µL of a medium containing 5 µmol/L fura 2-AM (DOJINDO), 2.5 mmol/L Probenecid (Sigma), 20 µmol/L indometacin (Sigma) and 10 mmol/L HEPES (Invitrogen), and this was incubated for about 60 minutes in a $CO_2$ incubator. After completion of the incubation, the medium was removed, and this was washed with a buffer solution for measurement (Hank's balanced salt solution (Nissui Pharmaceutical Co., Ltd., 9.8 g of the present product was dissolved in 1 L distilled water) containing 0.1 or 1 w/v % bovine serum albumin, 2 µmol/L indometacin, 2.5 mmol/L Probenecid and 10 mmol/L HEPES-NaOH (pH 7.4)) two times. To each well was added 1204 of a buffer solution for measurement, and this was allowed to stand in a $CO_2$ incubator for 30 minutes, and stabilized, which was subjected to an experiment.

The 96-well UV plate was set in a fluorescent spectral photometer (FDSS-3000, Hamamatsu Photonics K.K.), and an intracellular calcium concentration was measured. A buffered solution for measurement (30 µL) containing an agonist at a variety of concentrations was added to perform a reaction. Measurement of an intracellular calcium concentration was performed by irradiating cells with excited light of 340 nm and 380 nm alternately, measuring a fluorescent intensity at 500 nm, and obtaining a fluorescent intensity ratio of 2-wavelength excitation.

(1-3) Measurement of IP Agonist Activity (Measurement of cAMP Concentration)

On the measurement day, a medium was removed, and IP-CHO was washed with a phosphate-buffered physiological saline containing EDTA and not containing $Ca^{2+}$ and $Mg^{2+}$ once. A suitable amount of a phosphate-buffered physiological containing 2 mmol/L EDTA and not containing $Ca^{2+}$ and $Mg^{2+}$ was added, this was incubated at 37° C. for about 10 minutes, cells were peeled, cells were recovered (500 g) into a centrifuging tube, and centrifuged at room temperature for 3 minutes, and the supernatant was removed. Cells were suspended in a suitable amount of a buffer solution for measurement 1 (MEM medium (Invitrogen) containing 0.1 w/v % bovine serum albumin (Sigma) and 2 µmol/L diclofenac (Sigma)), and centrifuged at room temperature for 3 minutes at 500 g, and the supernatant was removed. Cells were suspended in a buffer solution for measurement 2 (MEM medium (Invitrogen) containing 0.1 w/v % bovine serum albumin (Sigma), 2 µmol/L diclofenac (Sigma) and 1 mmol/L 3-isobutyl-1-methylxanthine), and each 25 µL of the suspension was dispensed into a 96-well ½ area plate so that the cell number per well became $5.0 \times 10^4$. A buffer solution for measurement 2 (254) containing an agonist at a variety of concentrations was added to perform a reaction at room temperature for 30 minutes. Measurement of a cAMP concentration was performed using the cAMP HTRF HiRange kit (CIS bio International). According to the two step protocol of the kit manual, each 25 µL of cAMP-D2 and cryptase diluted with a lysis buffer were added, and this was incubated at room temperature for 1 hour. After incubation for 1 hour, time resolution fluorescence at 620 nm and 660 nm when excited at 340 nm was measured using Analyst GF (Molecular Device), and a ratio (TRF ratio) was obtained, thereby, a cAMP concentration was calculated from a calibration line.

<Result>

Using measured values obtained from the above method, an $EC_{50}$ value as an index of agonist activity of the present invention compound on mouse FP, mouse EP1 and mouse IP receptors was calculated.

For example, results of the compound described in Example 17 (23), the compound described in Example 17 (3), the compound described in Example 17 (4), the compound described in Example 17 (25), the compound described in Example 29 (12), the compound described in Example 32 and, as a comparative compound, the compound of Example 12 described in Patent Literature 2 shown by the following structural formula (hereinafter, abbreviated as Comparative Example A in some cases) are shown in Table 7.

[Chemical formula 62]

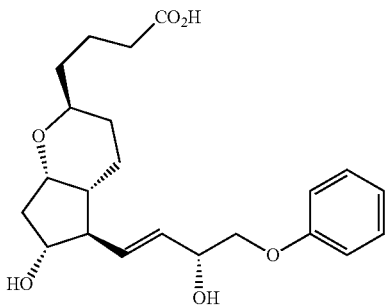

TABLE 7

|  | Agonist activity on various prostanoid receptors: $EC_{50}$ value (nmol/L) | | |
| --- | --- | --- | --- |
|  | FP | EP1 | IP |
| Example 17 (23) | 8.3 | 100 | >10000 |
| Example 17 (3) | 3.0 | 3200 | >10000 |
| Example 17 (4) | 8.8 | >10000 | >10000 |
| Example 17 (25) | 2.4 | 857 | >10000 |
| Example 29 (12) | 7.1 | >10000 | >10000 |
| Example 32 | 1.6 | >10000 | >10000 |
| Comparative Compound A | 1.1 | 3 | 710 |

From the above results, it was seen that the Comparative Compound A has agonist activity not only on a FP receptor, but also on an EP1 receptor and an IP receptor, while all of the present invention compounds have low agonist activity on an EP1 receptor and an IP receptor, and have selective agonist activity on a FP receptor.

(2) In Vivo Test

As can be easily understood by a person skilled in the art, in an in vivo test, since regarding all test compounds, carboxylic acid which is an active body has bad corneal permeability, pharmacological action was assessed by ocular instillation administration of a compound which had been converted into an ester such as an ethyl ester, an isopropyl ester etc. In addition, in a group of the present invention compounds, by ocular instillation-administering the ester body in an experimental animal (rabbit, dog etc.) by which pharmacological action is confirmed below and, thereafter, measuring a drug concentration of carboxylic acid in an aqueous humor, it was confirmed that the ester is rapidly converted into corresponding carboxylic acid.

(2-1) Intraocular Pressure Lowering Action

To one eye of a male dog (TOYO Beagle) which had been sufficiently acclimated in advance was ocular-instilled 30 μL of each test compound (compound of Example 16 (35) and compound of Example 16 (3)) which had been adjusted with a base (containing citrate buffer pH 6.5, 0.5% polysorbate 80, 1% propylene glycol, 0.01% benzalkonium chloride) to 0.01% (w/v) or 0.001% (w/v), respectively. The other eye was not treated. As a positive control compound, latanoprost which is the known compound was used.

Thereafter, an ocular surface anesthetic (Benoxil eye drops 0.4%, Santen Pharmaceutical Co., Ltd.) was subjected to ocular instillation to locally anesthetize eyes, and an intraocular pressure of each test compound before ocular instillation and after 2, 4, 6, 8, and 24 hours from ocular instillation was measured. An intraocular pressure was measured using a pneumatic applanation flat tonometer (Model 30 Classic, REICHERT). An intraocular pressure lowering rate (%) was calculated by the following equation.

Intraocular pressure lowering rate(%)=(intraocular pressure value before ocular instillation−intraocular pressure value at each point)/(intraocular pressure value before ocular instillation)×100 [Mathematic 1]

Among measured values at each point, the result showing the maximum action is shown in Table 8. An intraocular pressure of dogs to which each of the compound of Example 16 (35), the compound of Example 16 (3) and the compound of Example 16 (25) was ocular instillation-administered exhibited the stronger intraocular pressure lowering action as compared with latanoprost which is a positive control compound.

TABLE 8

| Compound | Administration dose (μg/mL) | Number of examples | Maximum of intraocular pressure lowering rate (%) |
| --- | --- | --- | --- |
| Example 16 (35) | 10 | 5 | 31 |
| Example 16 (3) | 10 | 5 | 35.7 |
| Example 16 (25) | 10 | 5 | 40.6 |
| Latanoprost | 50 | 10 | 25.4 |

(2-2) Assessment of Ocular Stimulating Property and Aqueous Humor Protein Concentration To one eye of a male rabbit (NewZealandWhite, 2.0 to 3.0 kg) was ocular-instilled 30 μL of the compound of Example 16 (35), the compound of Example 16 (3) and the compound of Example 16 (25) which had been adjusted to 0.1% (w/v) with a base (containing citrate buffer pH 6.5, 0.5% polysorbate 80, 1% propylene glycol, 0.01% benzalkonium chloride), respectively. Thereafter, an aqueous humor in anterior chamber after 0, 1, 2, 4, 6 and 8 hours from ocular instillation was collected, and a protein concentration in the humor was measured. As a comparative compound, the aforementioned methyl ester of the compound of Example 12 described in Patent Literature 2 (i.e. compound of Example 10 described in Patent Literature 2) (hereinafter, abbreviated as Comparative Compound B in some cases) was used.

Observation of the ocular general state was performed after 0, 1, 2, 4, 6 and 8 hours from ocular instillation, and visual remark of cornea, iris, and conjunctiva was observed according to determination criteria of the Draize method. A total of points of the resulting assessment points of each item $(=A_1 \times B_1 \times 5 + A_2 \times 5 + (A_3 + B_3 + C_3) \times 2)$ was assessed as a Draize score. Classification criteria of the Draize score was produced by referring to "Regarding Reference Material concerning Basic Idea of Biological Safety Test, Administrative Notice Medical Device Examination No. 36 dated Mar. 19, 2003, Pharmaceutical and Medical Devices Agency". Classification criteria was as follows: A Draize score of 0 or more and 5 or less was a non-stimulating substance, 5 or more and 15 or less was a slightly stimulating substance, 15 or more and 30 or less was a stimulating substance, 30 or more and 60 or less was an intermediate stimulating substance, 60 or more and 80 or less was an intermediate to strongly stimulating substance, and 80 or more and 110 or less was a strongly stimulating substance.

Regarding any test compound, a dose until a dissolution limit (150 to 1000 μg/mL) was administered and action of each active body was assessed.

Figure 2:
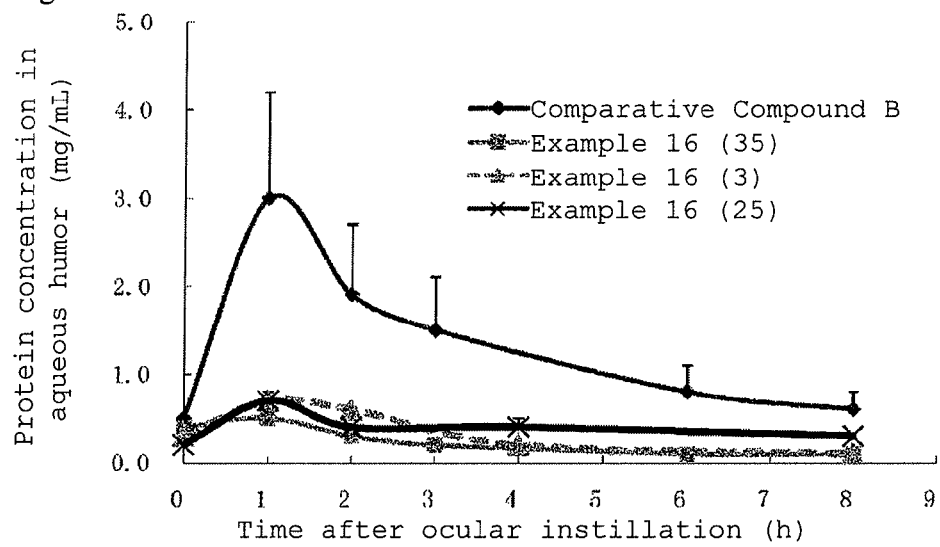
FIG. 2 A graph expressing transition of a concentration of a protein in a humor after ocular instillation of the present invention compound and a comparative compound.

Results are shown in the following FIG. 1 and FIG. 2. The Comparative Compound B was classified as a slightly stimulating substance from a maximum of the Draize score, based on its agonist activity on an IP receptor and, further, since it also raises a protein concentration in an aqueous humor, it was seen that it induces the side effect on eyes. To the contrary, it was seen that all of the compounds of Example 16 (35), Example 16 (3) and Example 16 (25) which are the present invention compounds were a non-stimulating substance by the Draize score, and had no action of raising a protein concentration in an aqueous humor.

From the foregoing, since the present invention compound has low agonist activity on an EP 1 receptor and an IP receptor, and has selective agonist activity on a FP receptor, it was suggested that not only it has strong intraocular pressure lowering action, but also side effects on eyes such as ocular itching action based on EP 1 receptor agonist activity, and ocular stimulating property such as hyperemia etc. and aqueous humor protein rise etc. based on IP receptor agonist activity can be avoided.

(2-3) Intraocular Pressure Lowering Action in Monkey Under Consciousness

To a left eye of a male monkey (crab-eating monkey) under consciousness was ocular instillation-administered 30 μL of a solution obtained by adjusting a test substance using the same base as that described above and, to a right eye was ocular instillation-administered 30 μL of a solution of only a base as a control, respectively. An intraocular pressure after administration was measured with time from administration initiation to after 24 hours. Upon measurement of an intraocular pressure, a crab-eating monkey was fixed on a monkey chair, and the monkey was anesthetized by ocular instillation-administering an ocular surface anesthetic (Benoxil eye drops 0.4% Santen Pharmaceutical Co., Ltd.). After mounting of a blepharostat (Handaya Co., Ltd.), an intraocular pressure of both eyes was measured (5 to 8 examples per group) using a pneumatic applanation flat tonometer (Model 30 Classic, REICHERT). A difference in an intraocular pressure value between control eyes and eyes to which a test substance had been administered, was calculated as an intraocular pressure lowering rate using the following equation, and sustainability of intraocular eye lowering action was assessed using a maximum intraocular pressure lowering rate during measurement and an intraocular pressure lowering rate after 24 hours. As the test substance, the Comparative Compound B, and the compounds of Example 16 (3), Example 16 (25) and Example 16 (35) were used, and an administration dose was 10 μg/mL in all cases.

Intraocular pressure lowering rate(%)=(intraocular pressure value of control eyes−intraocular pressure value of test substance-administered eyes)/(intraocular pressure value of control eyes)×100 [Mathematic 2]

The results are shown in the following Table 9. It was seen that, in the Comparative Compound B, a maximum intraocular pressure lowering rate was insufficient and, additionally, the lowering rate was reduced to less than 10% after 24 hours, and intraocular pressure lowering action cannot be sufficiently maintained. To the contrary, it was seen that all of the present invention compounds are compounds which have a high maximum intraocular pressure lowering rate, and can maintain an intraocular pressure lowering rate of about 15% or more even after 24 hours, and have strong and sustaining intraocular pressure lowering action.

TABLE 9

| Compound | Number of examples | Maximum intraocular pressure lowering rate (%) | Intraocular pressure lowering rate after 24 hours (%) |
|---|---|---|---|
| Comparative Compound B | 5 | 13.2 ± 3.2 | 7.0 ± 0.9 |
| Example 16 (35) | 5 | 19.2 ± 2.6 | 14.9 ± 4.7 |
| Example 16 (3) | 8 | 28.8 ± 2.2 | 15.1 ± 2.0 |
| Example 16 (25) | 8 | 26.5 ± 1.7 | 17.5 ± 2.1 |

Preparation Examples

Representative preparation examples used in the present invention will be shown below.

Preparation Example 1

Eye Drops

Eye drops according to the following formulation was prepared using the general-use method.

After glycerin (2.5 g) and polysorbate 80 (500 mg) were added to sterile purified water, the compound (1 mg) of Example 16 (35) was added to dissolve, sterile purified water was added to a total amount of 100 mL, and this was sterile-filtered with a membrane filter, and filled into a predetermined container to obtain eye drops of the following formulation.

According to the same manner as that described above, eye drops etc. containing 0.1 mg and 0.5 mg of the compound of Example 16 (35) in 100 mL can be prepared. Alternatively, other present invention compound can be used in place of the compound of Example 16 (35).

Preparation Example 2

Ocular Ointment

An ocular ointment of the following formulation was prepared using the general-use method.

A liquid paraffin and white vaseline were heat-sterilized in advance. After the compound (1 mg) of Example 16 (35) was sufficiently kneaded with a liquid paraffin (10 g), white vaseline was added to a total amount of 100 g, and the materials were sufficiently kneaded to obtain an ocular ointment of the following formulation.

INDUSTRIAL APPLICABILITY

Since the present invention compound has strong sustaining intraocular pressure lowering action and, further, has no side effects of eyes such as ocular stimulating property (hyperemia, corneal clouding etc.), aqueous humor protein rise etc., it is useful as an excellent agent for preventing and/or treating glaucoma etc.

The invention claimed is:

1. A compound represented by the general formula (I):

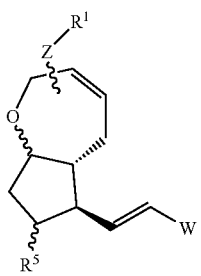
(I)

wherein $R^1$ represents (1) COOH, (2) COOR$^2$, (3) CH$_2$OH, or (4) CONR$^3$R$^4$, $R^2$ represents a C1-C6 alkyl group optionally substituted with a hydroxy group, ONO$_2$ or a C1-4 alkoxy group, $R^3$ and $R^4$ each represent independently a hydrogen atom, or a C1-4 alkyl group optionally substituted with ONO$_2$, $R^5$ represents a halogen atom, a hydroxy group, or a C1-4 alkoxy group, Z represents (1) —(CH$_2$)$_m$—, (2) —(CH$_2$)$_n$—CH=CH—, (3) —(CH$_2$)$_p$-A-CH$_2$—, or (4) ring 1, A represents an oxygen atom, or a sulfur atom, W represents a C1-6 alkyl group optionally substituted with 1 to 5 substituents selected from the group consisting of (1) a hydroxy group, (2) an oxo group, (3) a halogen atom, (4) a C1-4 alkyl group, (5) a C1-4 alkoxy group, (6) ring 2, (7) —O-ring 2, and (8) —S-ring 2, ring 1 and ring 2 each represent independently a C3-10 carbocycle or a 3- to 10-membered heterocycle, optionally substituted with 1 to 5 substituents selected from the group consisting of (1) a halogen atom, (2) CF$_3$, (3) OCF$_3$, (4) a C1-4 alkoxy group, (5) a C1-4 alkyl group, (6) a hydroxy group, and (7) a nitrile group, m represents an integer of 1 to 6, n represents an integer of 1 to 4, p represents an integer of 1 to 4,

⋯⋯ represents a single bond or a double bond, represents α configuration, represents β configuration, and represents α configuration, β configuration or an arbitrary mixture of them or a salt thereof.

2. The compound according to claim 1, which is represented by the general formula (I-1):

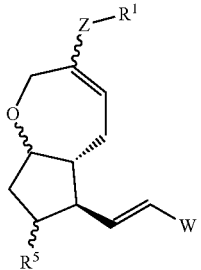
(I-1)

wherein all symbols represent the same meanings as those described in claim 1 or a salt thereof.

3. The compound according to claim 2, which is represented by the general formula (I-2):

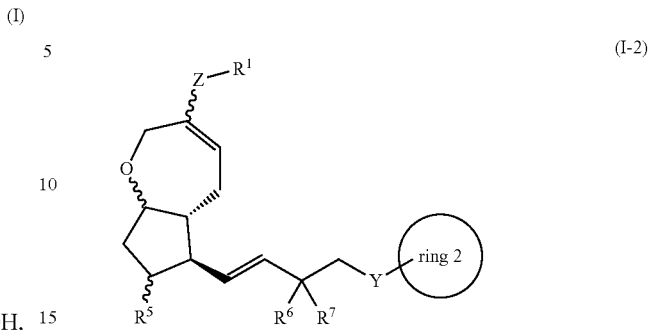
(I-2)

wherein $R^6$ and $R^7$ each represent independently a hydrogen atom, a hydroxy group, a halogen atom, a C1-4 alkyl group or a C1-4 alkoxy group, $R^6$ and $R^7$ may be taken together to form an oxo group, Y represents —CH$_2$—, —O— or —S—, and other symbols represent the same meanings as those described in claim 1 or a salt thereof.

4. The compound according to claim 3, wherein the ring 2 is a C3-7 carbocycle; or a salt thereof.

5. The compound according to claim 3, wherein Z is (1) —(CH$_2$)$_m$—, or (2) —(CH$_2$)$_p$-A-CH$_2$—, and other symbols represent the same meanings as those described claim 1; or a salt thereof.

6. The compound according to claim 3, wherein the compound represented by the general formula (I-2) is a compound selected from:
   (1) 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoic acid,
   (2) ethyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate,
   (3) 2-propanyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate,
   (4) 4-{(3S,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoic acid,
   (5) 2-propanyl 4-{(3S,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoate,
   (6) 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoic acid, and
   (7) 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate;
   or a salt thereof.

7. A pharmaceutical composition containing a compound represented by the general formula (I) according to claim 1, or a salt thereof.

8. The pharmaceutical composition according to claim 7, which is a FP agonist.

9. The pharmaceutical composition according to claim 7, which is an agent for treating an ocular disease.

10. The pharmaceutical composition according to claim 9, wherein the ocular disease is glaucoma, ocular hypertension, macular edema, macular degeneration, retina and optic nerve tensile force rise, myopia, hypermetropia, astigma, dry eye, amotio retinae, cataract, intraocular pressure rise due to trauma or inflammation, intraocular pressure rise due to a drug, or intraocular pressure rise after operation.

11. A method of treating an ocular disease, comprising administering an effective amount of a compound represented by the general formula (I) according to claim 1, or a salt thereof to a mammal.

* * * * *

UNITED STATES PATENT AND TRADEMARK OFFICE
CERTIFICATE OF CORRECTION

| | |
|---|---|
| PATENT NO. | : 8,962,868 B2 |
| APPLICATION NO. | : 14/081286 |
| DATED | : February 24, 2015 |
| INVENTOR(S) | : Tohru Kambe et al. |

It is certified that error appears in the above-identified patent and that said Letters Patent is hereby corrected as shown below:

In the claims,

In column 101, lines 5-14 (Claim 1),

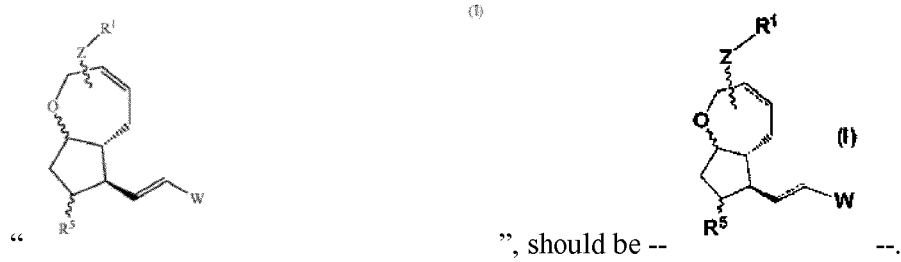

", should be -- --.

In column 101, lines 51-60 (Claim 2),

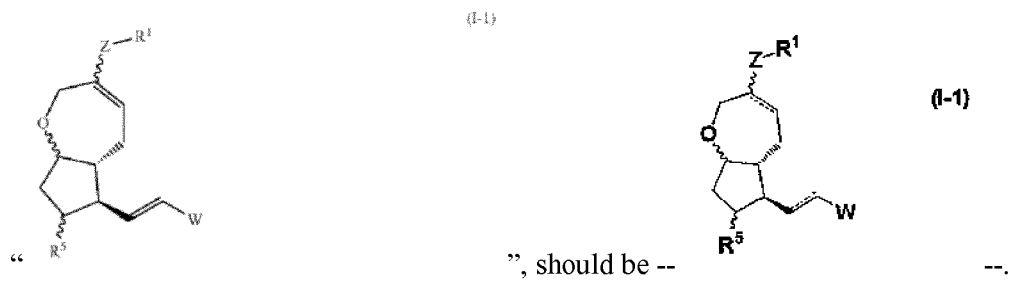

", should be -- --.

In column 102, lines 5-15 (Claim 3),

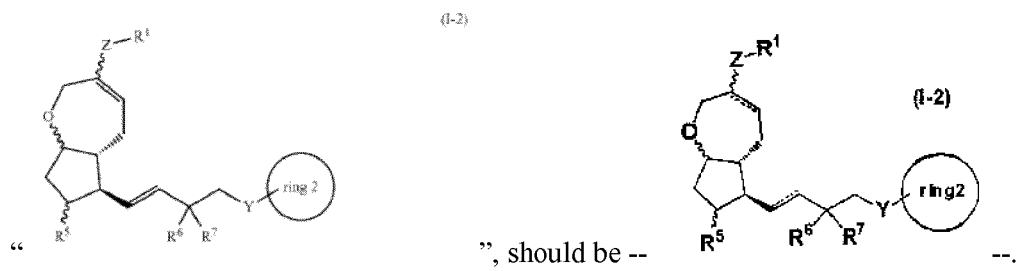

", should be -- --.

Signed and Sealed this
Twenty-third Day of February, 2016

Michelle K. Lee
*Director of the United States Patent and Trademark Office*